(12) United States Patent
Ede et al.

(10) Patent No.: US 7,956,219 B2
(45) Date of Patent: Jun. 7, 2011

(54) AMINO ACID ANALOGUES

(75) Inventors: Nicholas J. Ede, East Malvern (AU);
David M. Kaye, Beaumaris (AU);
Robert W. Trainor, Murrumbeena (AU);
Andrew N. Hunter, Beaumaris (AU)

(73) Assignee: Baker IDI Heart and Diabetes (AU)

( * ) Notice: Subject to any disclaimer, the term of this patent is extended or adjusted under 35 U.S.C. 154(b) by 76 days.

(21) Appl. No.: 10/513,768

(22) PCT Filed: May 8, 2003

(86) PCT No.: PCT/AU03/00551
§ 371 (c)(1),
(2), (4) Date: Aug. 31, 2005

(87) PCT Pub. No.: WO03/095421
PCT Pub. Date: Nov. 20, 2003

(65) Prior Publication Data
US 2006/0094902 A1     May 4, 2006

Related U.S. Application Data

(60) Provisional application No. 60/379,305, filed on May 9, 2002, provisional application No. 60/379,556, filed on May 9, 2002.

(51) Int. Cl.
*C07C 233/00* (2006.01)
*C07C 257/00* (2006.01)
(52) U.S. Cl. ........................ 564/248; 564/123
(58) Field of Classification Search ............. 549/441, 549/426; 564/123
See application file for complete search history.

(56) References Cited

U.S. PATENT DOCUMENTS
4,293,690 A * 10/1981 Sawa et al. ............... 536/27.61

FOREIGN PATENT DOCUMENTS
| | | | |
|---|---|---|---|
| CH | 280182 | * | 4/1952 |
| SU | 172307 | * | 6/1965 |
| WO | 9531194 | * | 11/1995 |
| WO | WO 9531194 | * | 11/1995 |
| WO | WO9531194 | * | 11/1995 |

OTHER PUBLICATIONS

Hcaplus 63:16263e-f.*
Hcaplus 72:132260.*
Hcaplus 1965:488647.*
Hcaplus 1953:37791.*
Hcaplus 124:185543.*
Protective Groups in Organic Synthesis, Third Edition. Theodora W. Greene et. al., 1999, Chapter 7, pp. 503-653.*
Hcaplus 107:23672.*
Hcaplus 88:170131.*
Adrian Marxer, "A New Bis-Guanylhydrazone with Antileukemic Properties", Experientia (1967), 23 (3), 173-4.*
Hcaplus 52:87901.*
Patani et. al. "Bioisosterism: A Rational Approach in Drug Design", Chem. Rev. 1996, 3147-3176.*
Hcaplus 107:23672 abstract, "A facile conversion of amino acides to guanidino acids", Miller et. al., 1986.*
Hcaplus 88:170131 abstract, "Preventing and treating rhinovirus infections with thiazolylphenylguanidines", 1977, American Cyanamid Co. as the Assignee.*
Marxer, Adrian. "A new bis-guanylhydrazone with antileukemic properties", Experientia, 1967, 23(3), 173-4.*
Hcaplus 52:87901, "Some phenylthiourea derivatives and their antituberculous activity", Doub et. al., (1958).*

* cited by examiner

*Primary Examiner* — Janet L Andres
*Assistant Examiner* — Heidi Reese
(74) *Attorney, Agent, or Firm* — Rader, Fishman & Grauer PLLC

(57) ABSTRACT

In the present specification we describe a new class of compounds, designed to modulate the ability of blood vessels to synthesize NO from L-arginine. In particular we have identified novel compounds which enhance the entry of L-arginine into cells. These compounds improve endothelial function, and thereby have the potential to retard the progression of vascular disease in conditions such as hypertension, heart failure and diabetes. This new class of drugs may also have other potentially, relevant pharmacological actions, including anti-hypertensive and anti-anginal actions.

29 Claims, 5 Drawing Sheets

Augmentation of vascular relaxation produced by increasing concentration of acetylcholine in the absence and presence of test compounds.

Arg uptake (% control)
Library M0006
Plate 1 of 3
$10^{-8}$ M

|   | 1 | 2 | 3 | 4 | 5 | 6 | 7 | 8 | 9 | 10 | 11 | 12 |
|---|---|---|---|---|---|---|---|---|---|----|----|----|
| A | x | x | x | 103% | 100% | 100% | 87% | 100% | 70% | 102% | 159% | 179% |
| B | x | x | x | 130% | 87% | 90% | 78% | 86% | 74% | 96% | 106% | 161% |
| C | x | x | x | 90% | 125% | 90% | 74% | 83% | 74% | 92% | 93% | 116% |
| D | x | x | x | 114% | 107% | 79% | 77% | 76% | 83% | 77% | 94% | 123% |
| E | x | x | x | 122% | 150% | 81% | 71% | 63% | 105% | 103% | 103% | 71% |
| F | x | x | x | 84% | 135% | 92% | 87% | 78% | 140% | 119% | 70% | 103% |
| G | x | x | x | 96% | 137% | 85% | 100% | 70% | 109% | 125% | 97% | 99% |
| H | x | x | x | 99% | 104% | 77% | 100% | 66% | 79% | 153% | 131% | 86% |

Arg uptake (% control)
Library M0006
Plate 1 of 3
$10^{-7}$ M

|   | 1 | 2 | 3 | 4 | 5 | 6 | 7 | 8 | 9 | 10 | 11 | 12 |
|---|---|---|---|---|---|---|---|---|---|----|----|----|
| A | x | x | x | 108% | 92% | 17% | 66% | 92% | 79% | 80% | 128% | 160% |
| B | x | x | x | 122% | 98% | 93% | 79% | 81% | 71% | 87% | 76% | 134% |
| C | x | x | x | 100% | 111% | 102% | 79% | 94% | 77% | 82% | 113% | 133% |
| D | x | x | x | 124% | 119% | 84% | 68% | 65% | 85% | 66% | 108% | 90% |
| E | x | x | x | 100% | 114% | 92% | 86% |  | 98% | 122% | 96% | 102% |
| F | x | x | x | 86% | 130% | 92% | 83% | 82% | 110% | 131% | 91% | 146% |
| G | x | x | x | 82% | 112% | 84% | 98% | 64% | 111% | 188% | 107% | 83% |
| H | x | x | x | 92% | 105% | 83% | 106% | 61% | 86% | 146% | 190% | 89% |

Arg uptake (% control)
Library M0006
Plate 2 of 3
$10^{-8}$ M

|   | 1 | 2 | 3 | 4 | 5 | 6 | 7 | 8 | 9 | 10 | 11 | 12 |
|---|---|---|---|---|---|---|---|---|---|----|----|----|
| A | x | x | x | 112% | 87% | 108% | 90% | 67% | 63% | 123% | 76% | 68% |
| B | x | x | x | 97% | 101% | 106% | 65% | 94% | 82% | 120% | 133% | 79% |
| C | x | x | x | 94% | 101% | 100% | 72% | 54% | 85% | 87% | 104% | 86% |
| D | x | x | x | 89% | 138% | 176% | 72% | 88% | 94% | 95% | 100% | 79% |
| E | x | x | x | 94% | 84% | 167% | 68% | 111% | 109% | 79% | 101% | 74% |
| F | x | x | x | 87% | 68% | 158% | 69% | 119% | 107% | 98% | 100% | 110% |
| G | x | x | x | 93% | 83% | 77% | 71% | 124% | 108% | 111% | 100% | 94% |
| H | x | x | x | 95% | 87% | 82% | 94% | 108% | 115% | 103% | 70% | 106% |

Arg uptake (% control)
Library M0006
Plate 2 of 3
$10^{-7}$ M

|   | 1 | 2 | 3 | 4 | 5 | 6 | 7 | 8 | 9 | 10 | 11 | 12 |
|---|---|---|---|---|---|---|---|---|---|----|----|----|
| A | x | x | x | 89% | 108% | 105% | 73% | 104% | 141% | 127% | 82% | 75% |
| B | x | x | x | 68% | 27% | 98% | 76% | 96% | 38% | 100% | 16% | 81% |
| C | x | x | x | 116% | 111% | 112% | 71% | 94% | 76% | 108% | 211% | 59% |
| D | x | x | x | 93% | 95% | 138% | 109% | 63% | 85% | 65% | 98% | 85% |
| E | x | x | x | 85% | 103% | 160% | 72% | 117% | 124% | 111% | 107% | 104% |
| F | x | x | x | 123% | 74% | 126% | 61% | 131% | 267% | 116% | 95% | 97% |
| G | x | x | x | 130% |  | 77% | 70% | 90% | 113% | 105% | 97% | 92% |
| H | x | x | x | 90% | 90% | 83% | 65% | 182% | 118% | 110% | 85% | 210% |

*Figure 4*

Arg uptake (% control)
Library M0006
Plate 3 of 3
$10^{-8}$ M

|   | 1 | 2 | 3 | 4 | 5 | 6 | 7 | 8 | 9 | 10 | 11 | 12 |
|---|---|---|---|---|---|---|---|---|---|----|----|----|
| A | x | x | x | 93% | 72% | 83% | 90% | 92% | 83% | 89% | 102% | 118% |
| B | x | x | x | 103% | 67% | 80% | 84% | 48% | 85% | 105% | 91% | 91% |
| C | x | x | x | 94% | 80% | 87% | 111% | 75% | 93% | 112% | 99% | 97% |
| D | x | x | x | 95% | 90% | 68% | 112% | 111% | 115% | 113% | 111% | 97% |
| E | x | x | x | x | x | x | x | x | x | x | x | x |
| F | x | x | x | x | x | x | x | x | x | x | x | x |
| G | x | x | x | x | x | x | x | x | x | x | x | x |
| H | x | x | x | x | x | x | x | x | x | x | x | x |

Arg uptake (% control)
Library M0006
Plate 3 of 3
$10^{-7}$ M

|   | 1 | 2 | 3 | 4 | 5 | 6 | 7 | 8 | 9 | 10 | 11 | 12 |
|---|---|---|---|---|---|---|---|---|---|----|----|----|
| A | x | x | x | 101% | 85% | 89% | 100% | 119% | 110% | 102% | 92% | 112% |
| B | x | x | x | 111% | 78% | 80% | 93% | 95% | 96% | 96% | 87% | 93% |
| C | x | x | x | 91% | 82% | 89% | 112% | 105% | 99% | 93% | 115% | 92% |
| D | x | x | x | 104% | 80% | 81% | 74% | 104% | 101% | 112% | 114% | 96% |
| E | x | x | x | x | x | x | x | x | x | x | x | x |
| F | x | x | x | x | x | x | x | x | x | x | x | x |
| G | x | x | x | x | x | x | x | x | x | x | x | x |
| H | x | x | x | x | x | x | x | x | x | x | x | x |

AMINO ACID ANALOGUES

This application claims priority from U.S. provisional application No. 60/379,305 filed on 9 May 2002 and from U.S. provisional application No. 60/379,556, filed on 9 May 2002, the contents of which are hereby incorporated by reference.

This invention relates to analogues of the amino acid L-arginine, and their use in therapy in the treatment of human disease, in particular their use for treatment of cardiovascular disease. The compounds of the invention have the ability to modulate, and preferably to enhance, the transport of the amino acid L-arginine into cells.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

Cardiovascular diseases are well-recognised as the leading cause of death in the western world. These conditions include atherosclerosis, diabetes, hypertension, peripheral vascular disease, coronary artery disease, myocardial infarction, congestive heart failure, and cerebrovascular disease. Some of these conditions, in particular atherosclerosis and Type II diabetes, have been associated with lifestyle factors such as diet and lack of physical exercise. Cardiovascular conditions are one of the most common sequelae of both Type I and Type II diabetes. However, while lifestyle changes can significantly reduce the risk of cardiovascular diseases or can slow their development, not all patients are able to comply with strict dietary and/or exercise regimens. Moreover, some patients have a genetic predisposition to development of cardiovascular conditions. Consequently there is a great need in the art for pharmaceutical agents which can influence the underlying pathological mechanisms of development of these conditions, and/or relieve their symptoms.

For example, a wide variety of drugs is available for treatment of hypertension, and many of these are also used in the treatment of congestive heart disease and heart failure. However, few agents have been specifically developed for the treatment of heart failure alone.

It is estimated that chronic or congestive heart failure affects approximately 5,000,000 people in the United States alone, ie. approximately 2% of the population, with approximately 400,000 new cases being diagnosed each year. Hospital and out-patient management costs are responsible for approximately 2.5% of the total health care costs, and congestive heart failure is one of the single most common causes of death in industrialised societies. Current treatments for congestive heart failure are very poor, and no satisfactory agents are available. Thus currently the primary aim of treatment is to prevent progression of the condition. However, in most cases patients have to utilise multiple pharmaceutical agents, and if the condition is not controlled the only treatments available are heart transplant or external cardiac assists. Although heart transplantation can be very successful, only very few patients can be treated because of the acute shortage of donors and the requirement for histocompatibility. External cardiac assists are suitable only for short-term use.

One of the major processes associated with the development of cardiovascular diseases is a disturbance of the functional properties of the endothelium, ie. the lining layer of blood vessels. The vascular endothelium plays a pivotal role in regulating blood flow by releasing, at the appropriate time, a chemical called nitric oxide. This process is illustrated schematically in FIG. 1. Nitric oxide (NO) is a small molecule which diffuses readily and plays a major role in vascular relaxation.

NO is generated by a family of cellular enzymes, nitric oxide synthases (NOS), which make use of the amino acid L-arginine. All isoforms of NOS catalyze a five-electron oxidation of one of two guanidino nitrogen atoms in L-arginine to yield nitric oxide and L-citrulline, as shown in FIG. 1.

The reaction involves two monooxygenation reactions, with N-γ-hydroxy-L-arginine as an intermediate product. The reaction requires several redox cofactors, including reduced nicotinamide adenine dinucleotide phosphate (NADPH), flavin adenine dinucleotide (FAD), flavin adenine mononucleotide (FMN) and tetrahydrobiopterin (THB4). It is known that the rate of production of NO is largely dependent upon the supply of L-arginine, and that supplementation with larger doses of L-arginine, per se, can improve endothelial function.

The clinical features of congestive heart failure (CHF) result from a complex interaction between reduced ventricular function, neurohormonal activation, and impaired endothelial function. While endothelial dysfunction has been well documented, the mechanisms which contribute to this dysfunction remained unclear until very recently. Possible such mechanisms included reduced expression of muscarinic cholinergic receptors (M) on endothelial cells, altered intracellular signalling, reduced NO production, increased NO degradation, or an attenuated response by the intracellular targets of NO or cyclic GMP (cGMP). Supplementation with oral or intravenous L-arginine has been shown to improve endothelial function in some conditions which are characterised by endothelial dysfunction, most notably atherosclerosis (Lerman et al 1998; Creager et al., 1992; Girerd et al., 1990). Such supplements have been shown to improve endothelial function in patients with heart failure (Hirooka et al., 1994; Rector et al, 1996), and we have shown that transport of L-arginine is impaired in patients with congestive heart failure; this could lead to a relative deficiency of intracellular arginine, thereby reducing NO synthesis (Kaye et al., 2000).

While in principle supplementation with L-arginine will have a beneficial effect, this approach suffers from the serious disadvantage that the doses required are extremely high, leading to toxic side effects as a result of the concomitant increase in urea levels. Thus there is a need in the art for alternative agents which are able to modulate L-arginine transport, without adversely affecting circulating urea levels. While supplementation with L-arginine does improve vasodilation, the doses of L-arginine which are required are very large, and result in potentially dangerous increases in blood urea levels. Thus an alternative method is needed.

Lowering intracellular L-arginine levels by inhibiting L-arginine transport has potential in the treatment of conditions in which the L-arginine-nitric oxide pathway is excessively active. These include sepsis resulting from infection, in which the NO pathway, particularly the pathway involving the inducible form of NOS (iNOS), or possibly L-arginine transport, is overactive; inflammation caused by non-infective disease states, including but not limited to arthritis, and chronic liver disease with its attendant toxaemia.

SUMMARY OF THE INVENTION

In the present specification we describe a new class of compounds, designed to modulate the ability of blood vessels to synthesize NO from L-arginine.

Without wishing to be bound by any proposed mechanism, we believe that the compounds of the invention modulate the synthesis of NO, presumably by up or down-regulating the transport of L-arginine, which is a substrate for NOS. In particular we have identified novel compounds which enhance the entry of L-arginine into cells. These compounds improve endothelial function, and thereby have the potential to retard the progression of vascular disease in conditions such as hypertension, heart failure and diabetes. This new class of drugs may also have other potentially, relevant pharmacological actions, including anti-hypertensive and anti-anginal actions.

The specification describes a compound which is able to modulate L-arginine transport into cells, in which the compound is of formula I

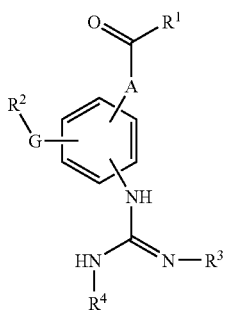

Formula I where
A is a methylene group or is absent;
G is O or is absent;
$R^1$ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl)alkyloxy, (cycloheteroalkyl)alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and $R^2$, $R^3$ and $R^4$ are selected from the group consisting of hydrogen, optionally substituted lower alkyl, aryl, aralkyl, heteroaryl, heteroaralkyl, cycloalkyl, and cycloheteroalkyl.

Preferably A is absent, $R^1$ is amino or hydroxyl, and G is O; $R^2$ is alkyl or cycloalkyl when G is O.

In a preferred embodiment, the compound is of formula II:

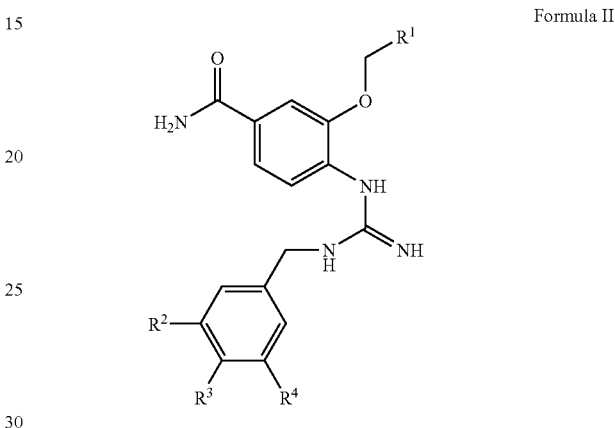

Formula II in which
-$R^5$- is cycloalkyl of 4-6 carbons;
-$R^6$- is trihaloalkyl of 1-3 carbon atoms, or halogen, or is absent;
-$R^7$- is a halogen or is absent; and
-$R^8$- is a halogen, or is trihaloalkyl of 1 to 3 carbon atoms.
Preferably -$R^5$- is cyclobutyl or cyclohexyl;
-$R^6$- is chlorine or absent; and
-$R^8$- is chlorine or trifluoromethyl.
More preferably both -$R^6$- and -$R^8$- are trifluoromethyl and -$R^7$- is absent, or both -$R^7$- and -$R^8$- are chlorine and $R^6$- is absent.

In a particularly preferred embodiment, the compound is one of the following compounds shown in Table 1:

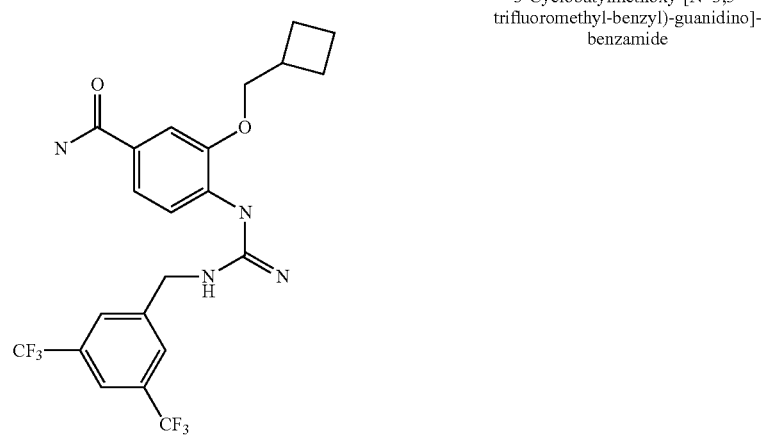

3-Cyclobutylmethoxy-[N'-3,5-trifluoromethyl-benzyl)-guanidino]-benzamide

-continued
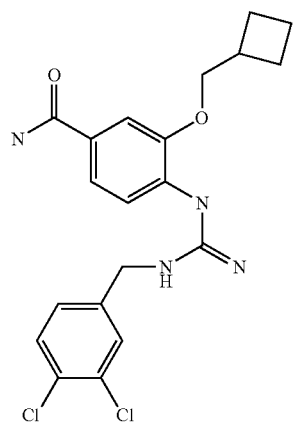
3-Cyclobutylmethoxy-4-[N'-(3,4-di-chloro-benzyl)-guanidino]-benzamide
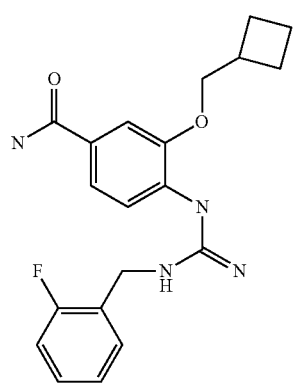
3-Cyclobutylmethoxy-4-[N'-(2-fluoro-benzyl)-guanidino)-benzamide
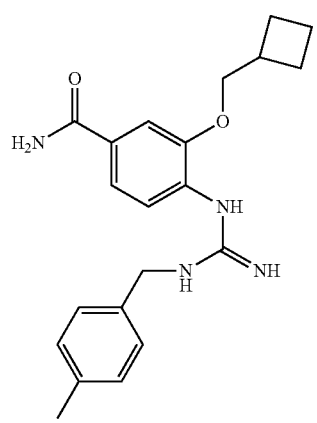
3-Cyclobutylmethoxy-4-[N',-(4-methyl-benzyl)-guanidino]-benzamide
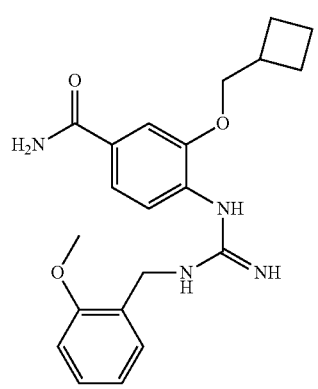
3-Cyclobutylmethoxy-4-[N'-(2-methoxy-benzyl)-guanidino]-benzamide

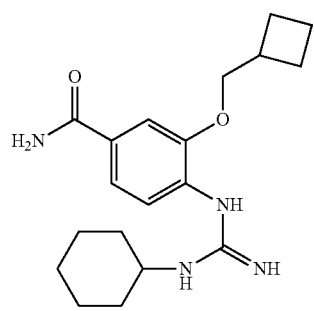
3-Cyclobutylmethoxy-4-(N',-cyclohexyl guanidino)-benzamide
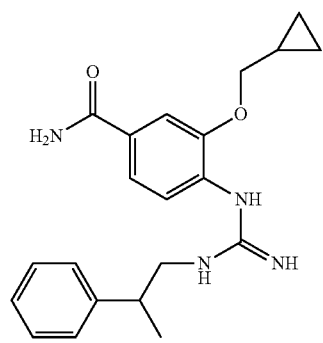
3-Cyclopropylmethoxy-4-[N'-{2-phenyl-propyl)-guanidino]-benzamide
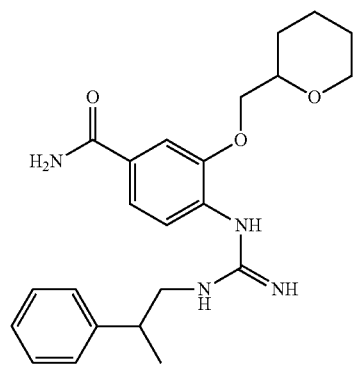
4-[N'-(2-Phenyl-propyl)-guanidino]-3-(tetrahydro-pyran-2-ylmethoxy)-benzamide
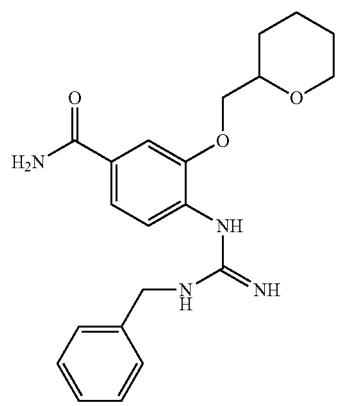
4-(N'-Benzyl-guanidino)-3-(tetrahydro-pyan-2-ylmethoxy)-benzamide 4-(N'-Benzo[1,3]dioxol-5-ylmethyl-
guanidino)-3-(tetrahydro-pyran-2-
ylmethoxy)-benzamide
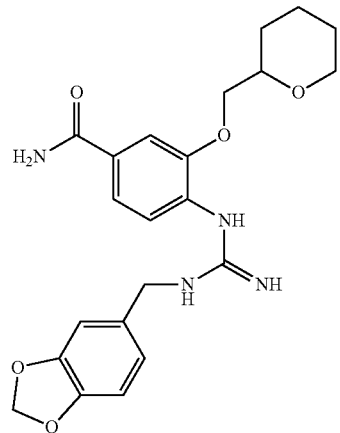
4-(N'-Isobutyl-guanidino)-3-
(tetrahydro-pyran-2-ylmethoxy)-benzamide
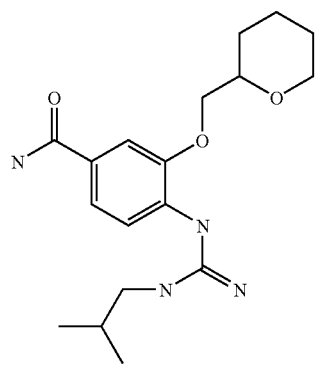
3-Cyclohexylmethoxy-4-[N'-(3,5- trifluoromethyl
-benzyl)-guanidino]-benzamide
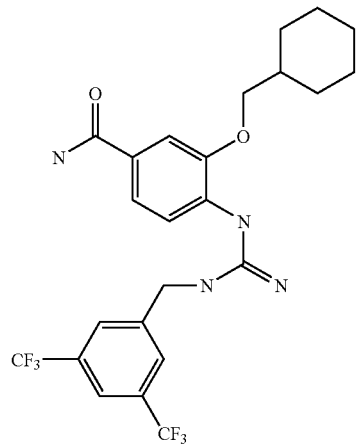

-continued
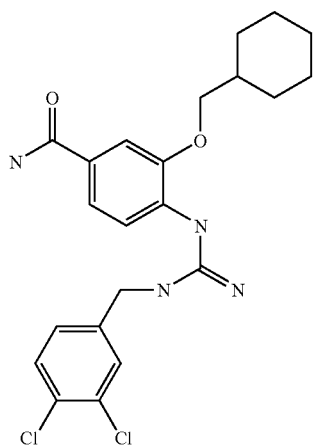
3-Cyclohexylmethoxy-4-[N'-(3,4-dichloro-benzyl)-guanidino]-benzamide
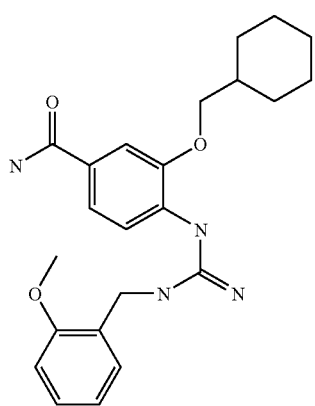
3-Cyclohexylmethoxy-4-[N'-(2-methoxy-benzyl)-guanidino]-benzamide
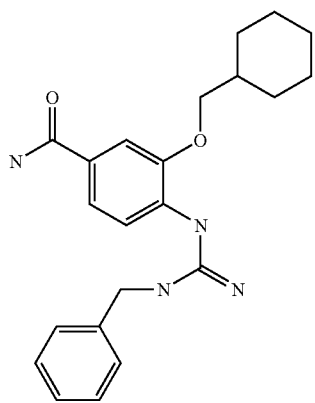
4-(N'-Benzyl-guanidino)-3-cyclohexyl-methoxy-benzamide
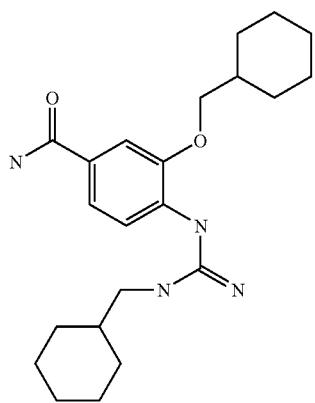
3-Cyclohexylmethoxy-4-(N'-cyclohexyl-methyl-guanidino)-benzamide

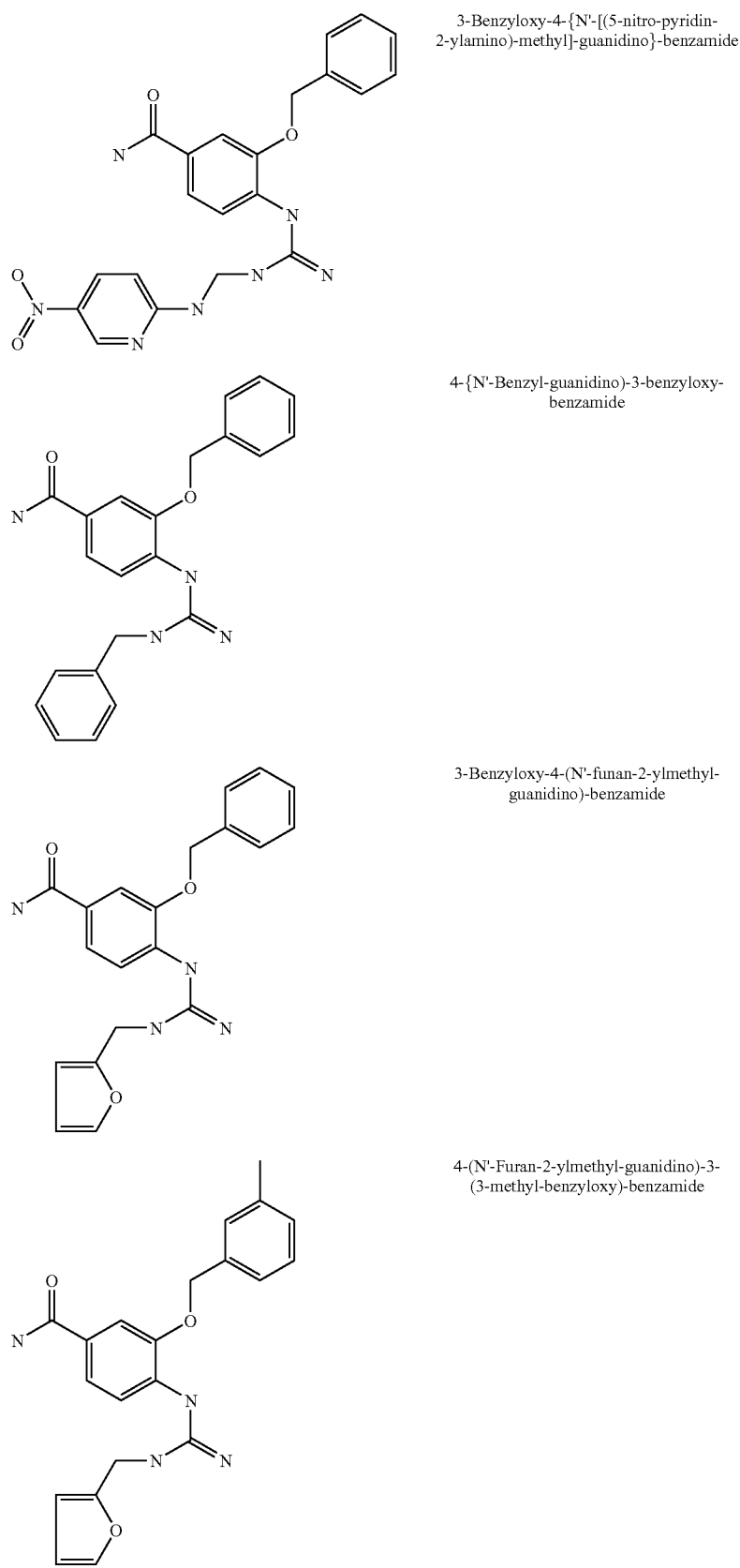
3-Benzyloxy-4-{N'-[(5-nitro-pyridin-2-ylamino)-methyl]-guanidino}-benzamide
4-{N'-Benzyl-guanidino)-3-benzyloxy-benzamide
3-Benzyloxy-4-(N'-funan-2-ylmethyl-guanidino)-benzamide
4-(N'-Furan-2-ylmethyl-guanidino)-3-(3-methyl-benzyloxy)-benzamide In a second aspect, the invention provides a library of compounds of formula I as defined above, or a sub-library thereof.

It will be clearly understood that the invention encompasses compounds which are able either to up-regulate or to down-regulate transport of L-arginine cross-cell membranes. Preferably the compounds are able to up-regulate such transport. More preferably the compounds of the invention enhance transport of L-arginine into cells, thereby stimulating NO production. Even more preferably the compounds up-regulate the activity of constitutive endothelial NOS (eNOS).

We have found that some compounds according to the invention, eg plate 1, G10 have a biphasic effect; they enhance L-arginine transport at low concentration, and inhibit such transport at high concentration. Thus a single compound may have both up-regulatory and down-regulatory activity.

The invention also encompasses methods of synthesis of the compounds.

According to a third aspect, the invention provides a composition comprising a compound of formula I, together with a pharmaceutically-acceptable carrier.

According to a fourth aspect, the invention provides a method of treatment of a condition associated with underactivity or hyperactivity of the NO synthetic pathway, comprising the step of administering an effective amount of a compound according to the invention to a subject in need of such treatment.

It is contemplated that in one preferred embodiment, the NO synthetic pathway is underactive; more preferably the condition is one in which vasodilatation is beneficial, for example, congestive heart failure, coronary artery disease, atherosclerosis, hypertension, diabetes-associated vascular disease, coronary vascular disease, or peripheral vascular disease.

In an alternative embodiment, the NO synthetic pathway is hyperactive; for example, the condition is sepsis, inflammation, including arthritis, or chronic liver disease. Preferably the condition is one associated with abnormal transport of L-arginine.

The subject may be a human, or may be a domestic or companion animal. While it is particularly contemplated that the compounds of the invention are suitable for use in medical treatment of humans, they are also applicable to veterinary treatment, including treatment of companion animals such as dogs and cats, and domestic animals such as horses, cattle and sheep, or zoo animals such as primates, felids, canids, bovids, and ungulates.

Methods and pharmaceutical carriers for preparation of pharmaceutical compositions are well known in the art, as set out in textbooks such as Remington's Pharmaceutical Sciences, 20th Edition, Williams & Wilkins, USA.

The compounds and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case.

In addition to treatment of cardiovascular conditions, it is contemplated that the compounds of the invention will be useful for modulation of the thrombin pathway, and consequently for treatment of abnormalities of blood clotting, and for treatment of sepsis.

While oral treatment is preferred, other routes may also be used, for example intravenous or intra-arterial injection or infusion, buccal, sub-lingual, or intranasal administration.

It will be clearly understood that the compounds of the invention may also be used in conjunction with one or more other agents which are useful in the treatment of heart failure. Ten agents in this class are in current clinical use; these include acetyl cholinesterase inhibitors such as captopril and enalapril; angiotensin receptor blockers ($AT_1$ antagonists); atrial natriuretic peptides; vasopeptidase inhibitors (ACE/neutral endopeptidase inhibitors); α- and β-blockers, including selective α- and β-adrenergic receptor antagonists, many of which are available; mineralocorticoid receptor antagonists; endothelin receptor antagonists; and endothelium converting enzyme antagonists. The person skilled in the art will be aware of a wide variety of suitable agents, and the topic has recently been reviewed (Macor & Kowala, 2000).

Preferably the compound of the invention is used in conjunction with an ACE inhibitor, a neutral endopeptidase inhibitor, or a β-blocker.

BRIEF DESCRIPTION OF THE FIGURES

FIG. 4 shows the results of experiments to test the stimulatory effects of compounds of the invention (as per Table 5) on arginine uptake by the endothelial cell line EA.hy.926.

DETAILED DESCRIPTION OF THE INVENTION

Figure 1:
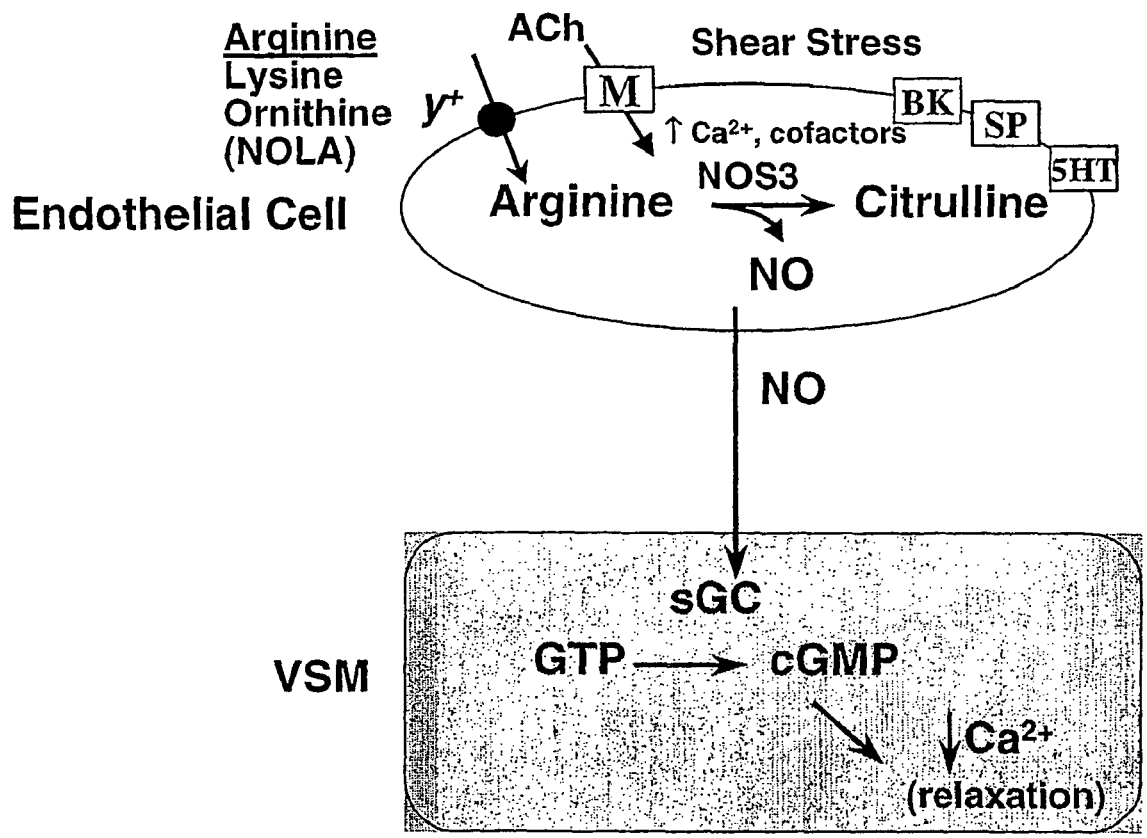
FIG. 1 is a schematic representation summarising the role of NO in vascular relaxation.

The invention will now be described in detail by way of reference only to the following non-limiting examples and drawings.

Abbreviations used herein are as follows:
amu atomic mass unit
$CH_2Cl_2$ dichloromethane
$Cs_2CO_3$ caesium carbonate (anhydrous)
DIC diisopropyl carbodiimide
DMAP dimethylaminopyridine
DMF N,N'-dimethylformamide
DMSO dimethyl sulfoxide
ESMS electrospray mass spectroscopy
$H_2O$ water
HPLC high performance liquid chromatography
LC/MS liquid chromatography/mass spectroscopy
MeCN acetonitrile
MS mass spectroscopy
MW molecular weight
${M+H}^+$ molecular ion
rt room temperature THF tetrahydrofuran
TFA trifluoroacetic acid
$t_R$ retention time

DEFINITIONS

Terms used in this specification have the following meanings:

Combinatorial Library

A "combinatorial library" or "array" is an intentionally created collection of differing molecules which can be prepared synthetically and screened for biological activity in a variety of different formats, such as libraries of soluble molecules, libraries of molecules bound to a solid support. Typically, combinatorial libraries contain between about 6 and two million compounds. In one embodiment, combinatorial libraries contain between about 48 and 1 million compounds. For example, combinatorial libraries may contain between about 96 and 250,000 compounds. In another embodiment, combinatorial libraries may contain about 40 to 100 compounds.

Most of the compounds synthesised and described in this application are synthesised using the techniques of combinatorial chemistry to produce combinatorial libraries. In contrast to traditional chemical synthesis, in which a unique compound is synthesised, combinatorial chemistry permits the reaction of a family of reagents $A_1$ to $A_n$ (the building-blocks) with a second family of reagents $B_1$ to $B_m$, generating nXm possible combinations (the combinatorial library).

A key feature of combinatorial techniques is that thousands of molecules can be screened in a small number of assays. To detect an active sequence generated via a combinatorial technique, the concentration of the active molecule is selected to be sufficiently great that the molecule can be detected within the sensitivity of the chosen assay. It will be appreciated that the number of unique molecules within a subset produced via a combinatorial technique depends on the number of positions of substitution and the number of different substituents employed.

Optionally Substituted

"Optionally substituted" refers to the replacement of hydrogen with a monovalent or divalent radical. Suitable substituent groups include hydroxyl, nitro, amino, imino, cyano, halo, thio, thioamido, amidino, oxo, oxamidino, methoxamidino, imidino, guanidino, sulfonamido, carboxyl, formyl, lower alkyl, halolower alkyl, lower alkoxy, halolower alkoxy, lower alkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like. The substituent group can itself be substituted.

The group substituted on to the substituent group can be, for example, carboxyl, halo, nitro, amino, cyano, hydroxyl, lower alkyl, lower alkoxy, aminocarbonyl, —SR, thioamido, —SO$_3$H, —SO$_2$R or cycloalkyl, where R is typically hydrogen, hydroxyl or lower alkyl. When the substituted substituent includes a straight chain group, the substitution can occur either within the chain (e.g., 2-hydroxypropyl, 2-aminobutyl, and the like) or at the chain terminus (e.g., 2-25 hydroxyethyl, 3-cyanopropyl, and the like). Substituted substituents can be straight chain, branched or cyclic arrangements of covalently bonded carbon or heteroatoms.

Lower Alkyl and Related Terms

"Lower alkyl" refers to branched or straight chain alkyl groups comprising 1 to 10 carbon atoms, preferably 1 to 6 carbon atoms which independently are unsubstituted or substituted, e.g., with one or more halogen, hydroxyl or other groups. Examples of lower alkyl groups include, but are not limited to, methyl, ethyl, propyl, isopropyl, n-butyl, t-butyl, n-hexyl, neopentyl, trifluoromethyl, pentafluoroethyl, and the like.

"Alkylenyl" refers to a divalent straight chain or branched chain saturated aliphatic radical having from 1 to 10 carbon atoms. Typical alkylenyl groups employed in compounds of the present invention are lower alkylenyl groups that have from 1 to about 6 carbon atoms in their backbone. "Alkenyl" refers to straight chain, branched, or cyclic radicals having one or more double bonds and from 2 to 20 carbon atoms, preferably 2 to 6 carbon atoms. "Alkynyl" refers to straight chain, branched, or cyclic radicals having one or more triple bonds and from 2 to 20 carbon atoms, preferably 2 to 10 carbon atoms.

The term "halolower alkyl" refers to a lower alkyl radical substituted with one or more halogen atoms. "Lower alkoxy" as used herein refers to RO—, where R is lower alkyl. Representative examples of lower alkoxy groups include methoxy, ethoxy, t-butoxy, trifluoromethoxy and the like.

"Lower alky-1-thio" refers to RS—, where R is lower alkyl.

"Cycloalkyl" refers to a mono- or polycyclic lower alkyl substituent. Typical cycloalkyl substituents have from 3 to 8 backbone (i.e., ring) atoms, in which each backbone atom is optionally substituted carbon. When used in context with cycloalkyl substituents, the term "polycyclic" refers to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

The term "cycloheteroalkyl" refers to cycloalkyl substituents that have from 1 to 5, and more typically from 1 to 4 heteroatoms (i.e., non-carbon atoms such as nitrogen, sulfur, and oxygen) in the ring structure, with the remaining atoms in the ring being optionally substituted carbon. Representative heterocycloalkyl moieties include morpholino, piperazinyl, piperidinyl, pyrrolidinyl, methylpryolidinyl, pyrrolidinone-yl, and the like.

The terms "(cycloalkyl)alkyl" and "(cycloheteroalkyl)alkyl" refer to alkyl chains substituted with cycloalkyl and cycloheteroalkyl groups respectively.

Halo

"Halo" refers to a halogen radical, such as fluorine, chlorine, bromine, or iodine.

Aryl and Related Terms

"Aryl" refers to monocyclic and polycyclic aromatic groups, or fused ring systems having at least one aromatic ring, having from 3 to 14 backbone carbon atoms. Examples of aryl groups include phenyl, naphthyl, dihydronaphthyl, tetrahydronaphthyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group.

Suitable aralkyl groups employed in compounds of the present invention include benzyl, picolyl, and the like.

Heteroaryl and Related Terms

The term "heteroaryl" refers to aryl groups having from one to four heteroatoms as ring atoms in an aromatic ring, with the remainder of the ring atoms being aromatic or non-aromatic carbon atoms. When used in connection with aryl substituents, the term "polycyclic" refers to fused and non-fused cyclic structures in which at least one cyclic structure is aromatic, such as benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

Amino and Related Terms

"Amino" refers to the group —NH$_2$. The term "lower alkylamino" refers to the group —NRR', where R and R' are each independently selected from hydrogen or loweralkyl. The term "arylamino" refers to the group —NRR' where R is aryl and R' is hydrogen, lower alkyl, aryl, or aralkyl. The term "aralkylamino" refers to the group —NRR' where R is aralkyl and R' is hydrogen, loweralkyl, aryl, or aralkyl. The terms "heteroarylamino" and heteroaralkylamino" are defined by analogy to arylamino and aralkylamino.

Thio and Related Terms

The term "thio" refers to —SH. The terms "lower alkylthio", "arylthio", "heteroarylthio", "cycloalkylthio", "cycloheteroalkylthio", "aralkylthio", "heteroaralkylthio", "(cycloalkyl)alkylthio", and "(cycloheteroalkyl)alkylthio" refer to —SR, where R is optionally substituted lower alkyl, aryl, heteroaryl; cycloalkyl, cycloheteroalkyl, aralkyl, heteroaralkyl, (cycloalkyl)alkyl, and (cycloheteroalkyl)alkyl respectively.

"Carboxyl" refers to —C(O)OH.

Imino and Oximino

The term "imino" refers to the group —C(=NR)—, where R can be hydrogen or optionally substituted lower alkyl, aryl, heteroaryl, or heteroaralkyl respectively. The terms "iminoloweralkyl", "iminocycloalkyl", "ininocycloheteroalkyl", "iminoaralkyl", "iminoheteroaralkyl", "(cycloalkyl)iminoalkyl", "(cycloiminoalkyl)alkyl", "(cycloiminoheteroalkyl)alkyl", and "(cycloheteroalkyl)iminoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an imino group, respectively.

The term "oximino" refers to the group —C(=NOR)—, where R can be hydrogen ("hydroximino") or optionally substituted lower alkyl, aryl, heteroaryl, or heteroaralkyl respectively. The terms "oximinoloweralkyl", "oximinocycloalkyl", "oximinocycloheteroalkyl", "oximinoaralkyl", "oximinoheteroaralkyl", "(cycloalkyl)oximinoalkyl", "(cyclooximinoalkyl)alkyl", "(cyclooximinoheteroalkyl)alkyl", and (cycloheteroalkyl)oximinoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an oximino group, respectively.

Methylene and Methine

The term "methylene" refers to an unsubstituted, monosubstituted, or disubstituted carbon atom having a formal sp$_3$ hybridization (i.e., —CRR'—, where R and R' are hydrogen or independent substituents).

The term "methine" as used herein refers to an unsubstituted or carbon atom having a formal sp2 hybridization (i.e., 10 —CR= or =CR—, where R is hydrogen a substituent).

It will be appreciated by those skilled in the art that the compounds of formula I may be modified to provide pharmaceutically acceptable derivatives thereof at any of the functional groups in the compounds of formula I. Of particular interest as such derivatives are compounds modified at the carboxyl function, hydroxyl functions or at the guanidino or amino groups. Thus compounds of interest include C$_{1-6}$ alkyl esters, such as methyl, ethyl, propyl or isopropyl esters, aryl esters, such as phenyl, benzoyl esters, and C$_{1-6}$ acetyl esters of the compounds of formula I.

The term "pharmaceutically acceptable derivative" means any pharmaceutically acceptable salt, ester or salt of such ester of a compound of formula I or any other compound which, upon administration to the recipient, is capable of providing a compound of formula I or a biologically active metabolite or residue thereof. Pharmaceutically acceptable salts of the compounds of formula I include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic acid, while not in themselves pharmaceutically acceptable, may be useful in the preparation of salts useful as intermediates in obtaining compounds of the invention and their pharmaceutically acceptable acid addition salts.

Salts derived from appropriate bases include alkali metal (eg. sodium), alkaline earth metal (eg. magnesium), ammonium, and NR$_4^+$ (where R is C$_{1-4}$alkyl) salts.

For the purposes of this specification it will be clearly understood that the word "comprising" means "including but not limited to", and that the word "comprises" has a corresponding meaning.

As used herein, the singular forms "a", "an", and "the" include the corresponding plural reference unless the context clearly dictates otherwise. Thus, for example, a reference to "an enzyme" includes a plurality of such enzymes, and a reference to "an amino acid" is a reference to one or more amino acids. Unless defined otherwise, all technical and scientific terms used herein have the same meaning as commonly understood by one of ordinary skill in the art to which this invention belongs. Although any materials and methods similar or equivalent to those described herein can be used to practice or test the present invention, the preferred materials and methods are now described.

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes preventing the disease from occurring in a subject who may be predisposed to the disease, but has not yet been diagnosed as having it; inhibiting the disease, ie., arresting its development; or relieving or ameliorating the effects of the disease, ie., cause regression of the effects of the disease.

The invention includes various pharmaceutical compositions useful for ameliorating disease. The pharmaceutical compositions according to one embodiment of the invention are prepared by bringing a compound of formula I, or an analogue, derivative or salt thereof, and one or more pharmaceutically-active agents or combinations of a compound of formula I and one or more other pharmaceutically-active agents, into a form suitable for administration to a subject, using carriers, excipients and additives or auxiliaries.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobials, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dosage units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, eg., in Langer, Science, 249: 1527, (1990). Formulations for oral use may be in the form of hard gelatin capsules, in which the active ingredient is mixed with an inert solid diluent, for example, calcium carbonate, calcium phosphate or kaolin. They may also be in the form of soft gelatin capsules, in which the active ingredient is mixed with water or an oil medium, such as peanut oil, liquid paraffin or olive oil.

Aqueous suspensions normally contain the active materials in admixture with excipients suitable for the manufacture of aqueous suspensions. Such excipients may be suspending agents such as sodium carboxymethyl cellulose, methyl cellulose, hydroxypropylmethylcellulose, sodium alginate, polyvinylpyrrolidone, gum tragacanth and gum acacia; dispersing or wetting agents, which may be (a) a naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleaginous suspension. This suspension may be formulated according to known methods using suitable dispersing or wetting agents and suspending agents such as those mentioned above. The sterile injectable preparation may also a sterile injectable solution or suspension in a non-toxic parenterally-acceptable diluent or solvent, for example, as a solution in 1,3-butanediol. Among the acceptable vehicles and solvents which may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compound of formula I of the present invention will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of active ingredient which may be combined with the carrier materials to produce a single dosage will vary, depending upon the host to be treated and the particular mode of administration. For example, a formulation intended for oral administration to humans may contain about 5 mg to 1 g of an active compound with an appropriate and convenient amount of carrier material, which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the invention may form solvates with water or common organic solvents. Such solvates are encompassed within the scope of the invention.

The compounds of the invention may additionally be combined with other compounds to provide an operative combination. It is intended to include any chemically compatible combination of pharmaceutically-active agents, as long as the combination does not eliminate the activity of the compound of formula I of this invention.

Synthesis of the Compounds of the Invention

The compounds of the present invention can be synthesized using techniques and materials known to those of skill in the art (Carey and Sundberg 1983; Carey and Sundberg 1983; Greene and Wuts 1991; March 1992). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.). The procedures described herein for synthesizing the compounds of the invention may include one or more steps of protection and deprotection, e.g., the formation and removal of acetal groups (Greene and Wuts 1991). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Various techniques well known in the chemical arts for the identification and quantification of chemical reaction products, such as proton and carbon-13 nuclear magnetic resonance ($^1$H and $^{13}$C NMR), infrared and ultraviolet spectroscopy ("IR" and "UV"), X-ray crystallography, elemental analysis ("EA").

HPLC and mass spectroscopy ("MS") can be used for identification, quantitation and purification as well.

Most of the compounds were synthesised using the technique of Solid Phase Chemistry (Ellman 1996). For many years we have used a multipin array system for solid-phase combinatorial peptide synthesis. This system is marketed by Mimotopes Pty Ltd, Clayton, Australia, and is used for synthesising libraries of organic compounds such as amino acid analogues, and for synthesising peptides and peptide libraries. The proprietary pin, Crown™ and SynPhase™ Lantern support systems utilise polyethylene or polypropylene copolymers grafted with 2-hydroxyethyl methacrylate polymer(HEMA), methacrylic acid/dimethylacrylamide polymer (MA/DMA) or polystyrene (PS) (Maeji et al. 1994).

In particular, suitable solid supports include resins, graft polymers such as Crown™ and SynPhase™ Lantern supports, and other derivatised surfaces suitable for solid phase synthesis. The solid support may be a resin of the type used for example in solid-phase peptide synthesis. Many suitable resins are known in the art, for example methylbenzhydrylamine (MBNA) resin, amino or carboxy tentagel resins, or 4-sulphamylbenzyl AM resin. One particularly preferred class of supports is aminomethylated polystyrene-grafted polyethylene or polypropylene, such as the Rink linker-derivatised aminomethylated polystyrene-grafted SynPhase™ lantern manufactured by Mimotopes Pty Ltd. (product code SPPSDRAM). Typical loadings are in the range of 34-36 micromole per unit. Another preferred support is the grafted resin described in International patent application No. PCT/AU01/00850.

Most of the compounds synthesised and described in the application are synthesised using the techniques of combinatorial chemistry to produce combinatorial libraries. As opposed to traditional chemical synthesis where a unique compound is synthesised, combinatorial chemistry permits the reaction of a family of reagents $A_1$ to $A_n$ (the building-blocks) with a second family of reagents $B_1$ to $B_m$ generating n×m possible combinations (the combinatorial library).

EXAMPLE 1

Synthesis of a Library of 180 Aryl Ether Guanidine Compounds (Library -M-0006) Library M0006 is a single compound library of 180 aryl ether guanidines in which there are two points of diversity. The scaffold for this library is a compound in which $R^2$ is derived from an alkyl halide and $R^4$ is derived from a primary amine.

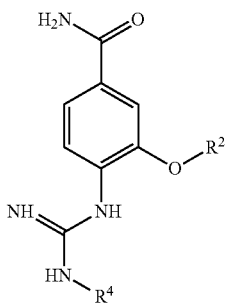

Scaffold for Library M0006

Thus the compounds present a subset of formula I in which A is absent, $R^1$ is amino, $R^2$ is derived from an alkyl halide, G is O, $R^3$ is H and $R^4$ is derived from a primary amine.

The library was synthesised using 9 alkyl halides for the $R^2$ substituents and 20 different amines for the $R^4$ substituents. This combination results in the generation of 180 compounds. The purity, as estimated by RP-HPLC at 214 nm, of compounds from Library M0006 averages 73.6%, and ranges from 56% to 88% (s.d.=7%) determined from an analytical set of 41 compounds (23% of the total number of compounds synthesised).

Synthesis 3-hydroxy-4-nitrobenzoic acid was coupled on to PS Rink Lanterns (Mimotopes Pty Ltd, Clayton, Victoria, Australia) loading capacity 35 μmol) using DIC/DMAP. The Lanterns were then treated with a solution of 10% ethanolamine in DMF to remove any concomitantly-formed esters. Deprotonation of the phenol with a potassium hydride/DMF solution followed by reaction with 9 alkyl halides generated 9 different aryl ethers. Using a solution of tin(II) chloride dihydrate in DMF, the nitro group in a 4-position was reduced to the corresponding aniline. The 180 Lanterns, derivatised with 9 different anilines were then treated with Fmoc-NCS. The in situ thioureas formed were then S-methylated with iodomethane. Subsequent reaction with 20 different amines resulted in the formation of the 20 different guanidines in the 4-position. Cleavage with 20% TFA/DCM afforded 180 aryl ether guanidines, which constitute Library M0006. This is summarised in Reaction Scheme 1.

Reaction Scheme 1

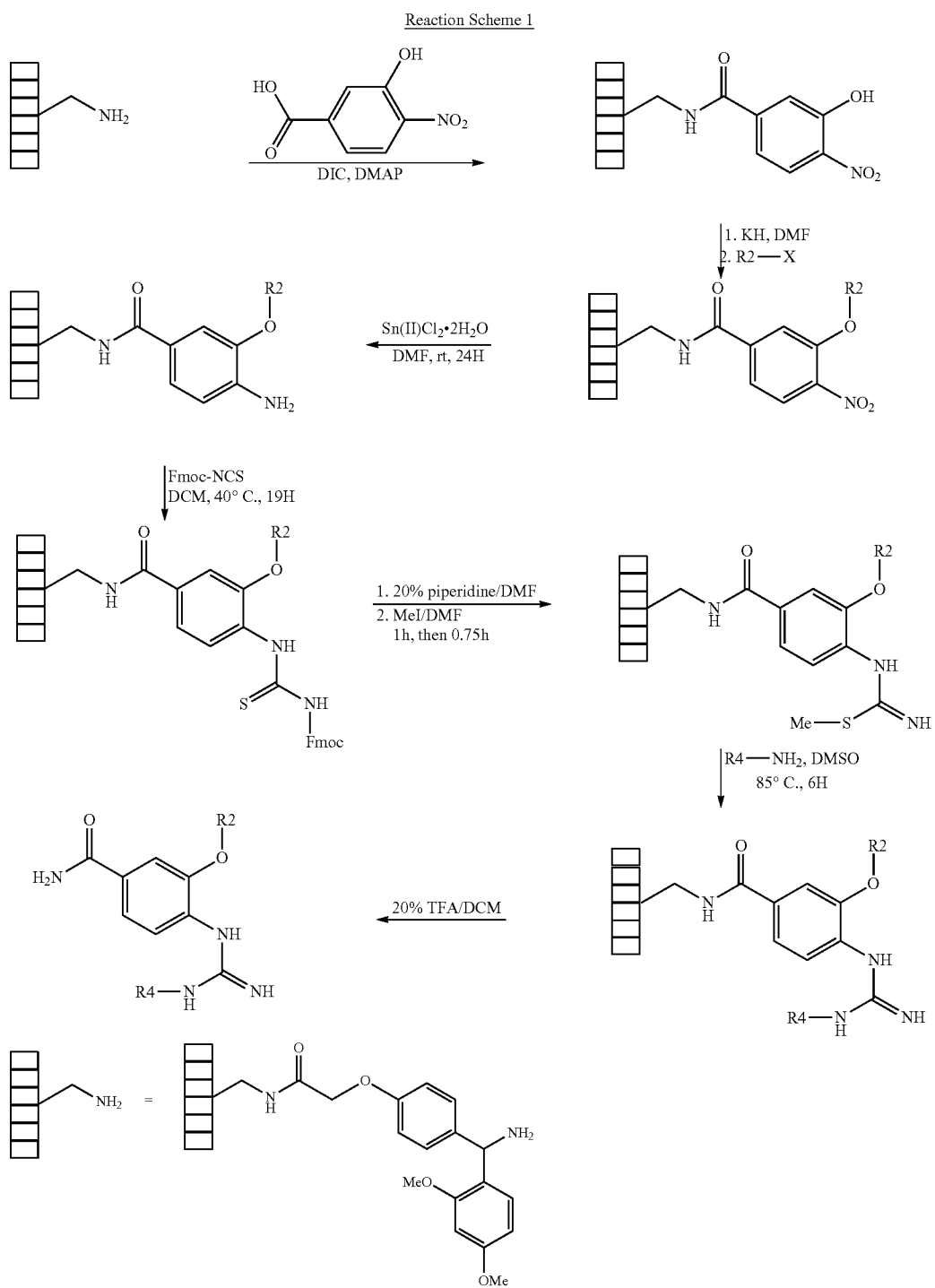

Reaction Scheme for Library M0006

(i) Coupling of 3-Hydroxy-4-nitrobenzoic Acid

Nine sets of 20 PS-D-RAM Lanterns (batch 1517, loading capacity 35 µmol) were reacted with a solution of 3-hydroxy-4-nitrobenzoic acid (0.2M), DIC (0.1M) and DMAP (0.05M) in DCM overnight at room temperature. The reaction solution was then drained and the Lanterns washed with DCM (4×20 min) and DMF (8×20 min). Concomitantly-formed esters were then cleaved using a solution of 10% ethanolamine/DMF: Lanterns were treated with 10% ethanolamine/DMF (1×15 min) followed by DMF (1 or 2×15 min); the Lanterns were given a sufficient number of treatments as to afford an entirely colourless eluent. When no further colour was observed, the Lanterns were washed with a solution of 50% AcOH (AR grade)/DCM (2×20 min) followed by DCM (4×15 min). A stain test of 0.2% bromophenol blue/DMF performed on a portion of one Lantern gave a negative result. The Lanterns were air-dried.

(ii) Alkylation

The Lanterns from step (i) were treated with a slurry of excess potassium hydride freshly extracted from mineral oil in anhydrous DMF for 30 min; then the Lanterns were rinsed twice with anhydrous DMF (1st cycle for 5 min; second cycle for about 30 min, or until the R1-X/Cs$_2$CO$_3$ solutions were prepared). Nine solutions containing the appropriate alkylating reagent and Cs$_2$CO$_3$ in distilled DMF were prepared. The order of addition was cesium carbonate, then DMF, then alkylating reagent. The different substituents used for R$^2$ and R$^4$, and the alkylating conditions used to generate R$^2$, are summarised in Tables 2 to 4 respectively.

TABLE 2

Summary of R$^2$-group structures and details for library M0006

| Fragment Tag | R$^2$-Group Structure | Reagent Name | Reagent Tag |
|---|---|---|---|
| R1m1 |  | (bromomethyl)cyclobutane | CCA004 |
| R1m2 |  | (bromomethyl)cyclopropane | CCA001 |
| R1m3 | 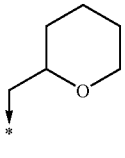 | 2-(bromomethyl)tetrahydro-2H-pyran | CCB001 |
| R1m4 | 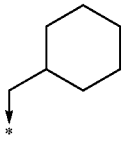 | (bromomethyl)cyclohexane | CCA002 |
| R1m8 | 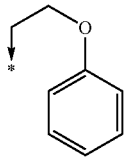 | 2-phenoxyethyl bromide | CCB004 |
| R1m9 | 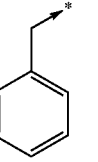 | benzyl bromide | CCC001 |
| R1m10 | 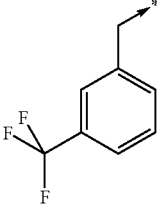 | 3-(trifluoromethyl)benzyl bromide a-bromo-a,a,a-m-trifluoroxylene | CCD018 |
| R1m11 | 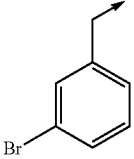 | 3-bromobenzyl bromide | CCD019 |
| R1m12 | 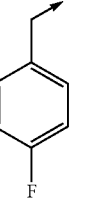 | 4-fluorobenzyl bromide | CCD020 |

TABLE 3

Summary of R$^4$-group structures and details for library M0006

| Fragment Tag | R$^4$-Group Structure | Reagent Name | Reagent Tag |
|---|---|---|---|
| r2m4 | 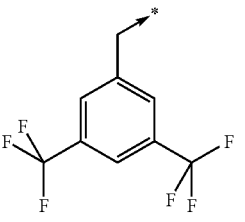 | 3,5-bis(trifluoromethyl)benzylamine | DAD005 |

TABLE 3-continued

Summary of R⁴-group structures and details for library M0006

| Fragment Tag | R⁴-Group Structure | Reagent Name | Reagent Tag |
|---|---|---|---|
| r2m5 | 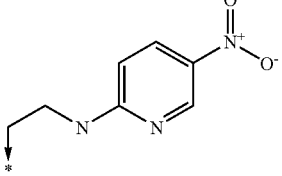 | 2-(2-aminoethylamino)-5-nitropyridine | DAG001 |
| r2m7 | 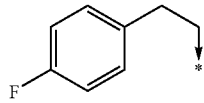 | 4-fluorophenethylamine | DAD023 |
| r2m8 | 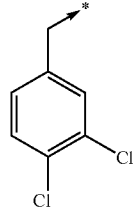 | 3,4-dichlorobenzylamine | DAD024 |
| r2m9 | 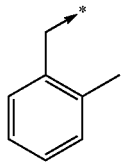 | 2-methylbenzylamine | DAC009 |
| r2m12 | 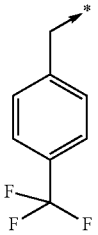 | 4-(trifluoromethyl)benzylamine | DAD006 |
| r2m13 | 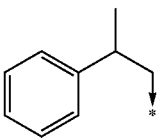 | 1-amino-2-phenylpropane β-phenethylamine | DAC008 |
| r2m16 | 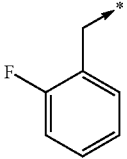 | 2-fluorobenzylamine | DAD004 |
| r2m17 | 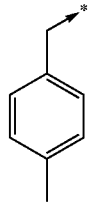 | 4-methylbenzylamine | DAC007 |

TABLE 3-continued

Summary of R⁴-group structures and details for library M0006

| Fragment Tag | R⁴-Group Structure | Reagent Name | Reagent Tag |
|---|---|---|---|
| r2m18 | 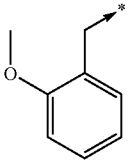 | 2-methoxybenzylamine | DAD009 |
| r2m20 | 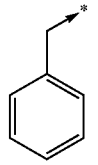 | benzylamine | DAC003 |
| r2m22 | 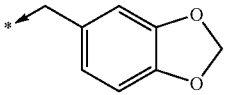 | piperonylamine | DAD002 |
| r2m24 | 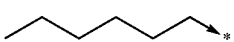 | hexylamine | DAA002 |
| r2m25 | 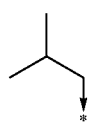 | isobutylamine | DAA010 |
| r2m40 | 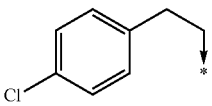 | 2-(4-chlorophenyl)ethylamine | DAD008 |
| r2m46 | 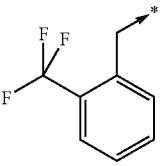 | 2-(trifluoromethyl)benzylamine | DAD029 |
| r2m53 | 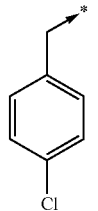 | 4-chlorobenzylamine | DAD034 |
| r2m58 | 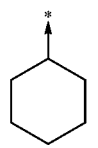 | cyclohexylamine | DAA001 |
| r2m60 | 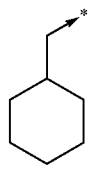 | cyclohexanemethylamine | DAA003 |

TABLE 3-continued

Summary of R⁴-group structures and details for library M0006

| Fragment Tag | R⁴-Group Structure | Reagent Name | Reagent Tag |
|---|---|---|---|
| r2m62 | 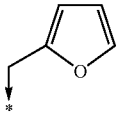 | furfurylamine | DAG005 |

TABLE 4

Conditions Employed for Alkylating Reagents

| Alkylating Reagent | Alkyl Halide Concentration | Cesium(I) Concentration | Reaction Time | Reaction Temperature |
|---|---|---|---|---|
| (Bromomethyl)cyclobutane | 1.0 M | 0.3 M | 24 h | 100° C. |
| (Bromomethyl)cyclopropane | 1.0 M | 0.3 M | 24 h | 100° C. |
| 2-(Bromomethyl)-tetrahydro-2H-pyran | 1.0 M | 0.3 M | 24 h | 100° C. |
| (Bromomethyl)cyclohexane | 1.0 M | 0.3 M | 24 h | 100° C. |
| 2-Phenoxyethyl bromide | 1.0 M | 0.06 M | 24 h | 100° C. |
| Benzyl bromide | 1.0 M | 0.06 M | 24 h | 40° C. |
| 3-(Trifluoromethyl)benzyl bromide | 1.0 M | 0.6 M | 48 h | 100° C. |
| 3-Bromobenzyl bromide | 1.0 M | 0.06 M | 24 h | 40° C. |
| 4-Fluorobenzyl bromide | 1.0 M | 0.06 M | 24 h | 40° C. |

The reaction solution from each flask was then drained, and the Lantern sets transferred to clean 100 mL vessels to facilitate $Cs_2CO_3$ removal. The Lanterns were then washed with DMF (distilled) (3×10 min), 50% DMF (distilled)/$H_2O$ (1×30 min, 1×10 min), DMF (distilled) (2×10 min) and DCM (1×30 min, 2×10 min, 1×2 min). The Lantern sets were then vacuum dried at 40° C.

The analysis by RP-HPLC of these 9 intermediates showed that full alkylation was not achieved in all cases. Only 3 of the ethers returned raw HPLC purities of >80%. These were (bromomethyl)cyclobutane (r1m1); 2-(bromomethyl)tetrahydro-2H-pyran (r1m3) and (bromomethyl)cyclohexane (r1m4). The remaining sets of Lanterns were therefore re-treated with KH/DMF followed by alkylating reagent at reduced concentration (0.5M). $Cs_2CO_3$ was omitted from all second pass reaction solutions. The sets of Lanterns derivatised with benzyl bromide, 3-bromobenzyl bromide and 4-fluorobenzyl bromide were heated to 40° C. for 44 h. Lanterns derivatised with 2-phenoxyethyl bromide and (bromomethyl)cyclopropane were heated to 80° C. for 44 h. The Lantern set derivatised with 3-(trifluoromethyl)benzyl bromide was heated initially to 80° C. for 1 h, then at 40° C. for the remaining 43 h. For reactions involving (bromomethyl) cyclopropane and 2-phenoxyethyl bromide, 2 different solutions of the alkylating reagent were used. After 18.5 h, the first alkyl halide solution was removed, the Lanterns were washed briefly with anhydrous DMF then re-treated with a second solution of the alkylating reagent (0.5M) for the remaining 25.5 h. The Lanterns were then washed with DMF (3×10 min) and DCM (2×10 min) and then vacuum dried at 40° C. overnight.

(iii) Aniline Formation Using Tin(II) Chloride

Nine solutions of tin(II) chloride dihydrate (1.0M) in distilled DMF were prepared. These were then added to the nine sets of Lanterns derivatised with the 9 different aryl ethers and allowed to stand overnight at 40° C. The reaction solutions were then drained and the Lanterns washed with DMF (2×30 min), 50% DMF/$H_2O$ (1×30 min), DMF (1×20 min), DCM (3×10 min). The Lanterns were then vacuum dried for 3 h.

(iv) Guanidine Formation

Transponders were inserted into the Lanterns and a TranSort program was created for the directed sort for the R2 group. The Lanterns were treated with Fmoc-NCS (0.2M) in DCM at room temperature for 14 h then at 40° C. for 1 h. The reaction solution was drained and the Lanterns washed with DCM (3×10 min), DMF (3×10 min) and DCM (3×10 min). The Lanterns were then vacuum dried at 40° C. for 1 h.

The Lanterns were Fmoc-deprotected with 20% piperidine/DMF for 1 h. The piperidine solution was drained and the Lanterns subjected to a second treatment with fresh 20% piperidine/DMF for 45 minutes. The Lanterns were drained and washed with DMF (3×10 min), 50% DMF/DCM (3×10 min) and DCM (3×10 min).

A solution of iodomethane (0.2M) in DMF (distilled) was prepared. To this solution was added the Fmoc-deprotected Lanterns. The Lanterns were then stood at room temperature for 1 h. The iodomethane solution was removed and the Lanterns re-treated with a second solution of iodomethane (0.2M) in DMF for 45 min. The Lanterns were drained then washed with DMF (3×10 min) and DCM (3×10 min) and vacuum dried overnight at 40° C.

Twenty solutions of the corresponding amine (2M) [refer Table 3] in DMSO (AR grade) were prepared. The sets of Lanterns, as sorted using TranSort, were then added to these amine solutions and allowed to stand at 85° C. for 6 h. At the completion of the reaction, the amine solutions were drained and the Lanterns washed with warm DMSO (2×10 min), DMF (3×10 min), 50% DMF/DCM (3×10 min) and DCM (3×10 min). The Lanterns were then vacuum dried overnight at 40° C.

(v) Cleavage from the Solid Phase

The Lanterns were prepared for cleavage using TranSort. The Lanterns were then cleaved using 1 mL per Lantern of 20% TFA (distilled)/DCM for 1 h using the 2 mL square deep-well format. The resulting cleavage solutions were evaporated in vacuo using a centrifugal evaporator (Gene-Vac). The resulting material was reconstituted in neat acetonitrile (0.9 mL) and re-evaporated. The samples were dissolved in 90% MeCN/$H_2O$ for plating purposes and re-evaporated to dryness.

Analysis

A selection of 43 compounds was analyzed by reverse phase HPLC and electrospray mass spectrometry, under the following conditions:

Reverse phase HPLC analysis was carried out using a Rainin Microsorb-MV C18 column, (5 µm 100 Å; 50×4.6 mm), under the following conditions: Eluent A: 0.1% $H_3PO_4$ (aq); Eluent B: 0.1% $H_3PO_4$ in 90% MeCN (aq); Gradient: 0-100% Buffer B over 11 min; Flow rate: 1.5 mL/min; Wavelength detection: 214 nm.

ESMS was performed on an API III LC/MS/MS instrument (Perkin Elmer/Sciex) using an electrospray inlet, and the following conditions: Solvent: 0.1% ACOH in 60% MeCN (aq); Flow rate: 25 µL/min; Ionspray: 5000V; Orifice plate: 55V; Acquisition time: 2.30 min; Scan range: 100-1000 amu/z; Scan step size: 0.2 amu/z.

The results are summarised in Table 5. All compounds sampled displayed the target molecular weight. The LC/MS results indicate that at least two ions are detected under each major peak. These are $MH^+$ and $(MH+122)^+$. Additionally, there are ions corresponding to $(MH+(n \times 122))^+$ where n is an integer. An ion of m/z 222 was also detected in the buffer solution of the instrument.

TABLE 5

Summary of Analytical Results

| | Compound Identification | | HPLC and LC-MS data (214 nm) | | | |
|---|---|---|---|---|---|---|
| Compound ID | R Groups | Monoisotopic FW | Retention Time (min) | Peak Area (%) | Target Found | (MH) + Observed |
| M000601A04 | r1m1-r2m4 | 488 | 8.33 | 67.7 | ✓ | 489.1 |
| M000601A05 | r1m1-r2m5 | 427 | 6.13 | 70.8 | ✓ | 428.3 |
| M12812044BP | R1m1-r2m8 | 420 | 7.41 | 95.6 | ✓ | 421.1 |
| M000601B04 | r1m1-r2m18 | 382 | 6.82 | 72.4 | ✓ | 383.3 |
| M000601B05 | r1m1-r2m20 | 352 | 6.42 | 75.6 | ✓ | 353.5 |
| M000601C04 | r1m1-r2m60 | 358 | 7.46 | 70.8 | ✓ | 359.3 |
| M000601C05 | r1m1-r2m62 | 342 | 5.78 | 62.2 | ✓ | 343.3 |
| M000601D04 | r1m2-r2m16 | 356 | 5.80 | 76.3 | ✓ | 357.0 |
| M000601D05 | r1m2-r2m17 | 352 | 6.34 | 76.7 | ✓ | 353.2 |
| M000601E04 | r1m2-r2m53 | 407 | 6.49 | 74.3 | ✓ | 372.9 |
| M000601E05 | r1m2-r2m58 | 330 | 6.15 | 60.1 | ✓ | 331.3 |
| M000601F04 | r1m3-r2m12 | 450 | 7.00 | 79.4 | ✓ | 451.1 |
| M000601F05 | r1m3-r2m13 | 410 | 6.68 | 80.1 | ✓ | 411.4 |
| M000601G04 | r1m3-r2m40 | 430 | 7.02 | 78.2 | ✓ | 431.4 |
| M000601G05 | r1m3-r2m46 | 450 | 6.75 | 72.6 | ✓ | 451.1 |
| M12812044CP | R1m4-r2m4 | 516 | 8.71 | 99.3 | ✓ | 517.1 |
| M000601H04 | r1m4-r2m8 | 448 | 8.47 | 73.7 | ✓ | 449.0 |
| M000601H05 | r1m4-r2m9 | 394 | 7.86 | 77.3 | ✓ | 395.1 |
| M000602A04 | r1m4-r2m24 | 374 | 8.52 | 69.9 | ✓ | 375.3 |
| M000602A05 | r1m4-r2m25 | 346 | 7.22 | 69.6 | ✓ | 347.2 |
| M000602D05 | r1m8-r2m4 | 540 | 8.51 | 73.2 | ✓ | 541.1 |
| M000602E04 | r1m8-r2m17 | 418 | 7.29 | 78.0 | ✓ | 419.1 |
| M000602E05 | r1m8-r2m18 | 434 | 7.10 | 79.6 | ✓ | 435.1 |
| M000602F04 | r1m8-r2m58 | 396 | 7.14 | 56.2 | ✓ | 397.1 |
| M000602F05 | r1m8-r2m60 | 410 | 7.71 | 74.3 | ✓ | 411.4 |
| M000602G04 | r1m9-r2m13 | 402 | 7.17 | 76.2 | ✓ | 403.2 |
| M000602G05 | r1m9-r2m16 | 392 | 6.48 | 73.8 | ✓ | 392.9 |
| M000602H04 | r1m9-r2m46 | 442 | 7.26 | 68.8 | ✓ | 443.0 |
| M000602H05 | r1m9-r2m53 | 408 | 7.15 | 77.1 | ✓ | 409.1 |
| M000603A04 | r1m10-r2m9 | 456 | 7.84 | 88.1 | ✓ | 457.1 |
| M000603A05 | r1m10-r2m12 | 510 | 8.25 | 85.8 | ✓ | 511.2 |
| M000603B04 | r1m10-r2m25 | 408 | 7.29 | 78.3 | ✓ | 409.3 |
| M000603B05 | r1m10-r2m40 | 490 | 8.33 | 86.2 | ✓ | 491.0 |
| M000603C04 | r1m11-r2m7 | 484 | 7.70 | 75.5 | ✓ | 485.3 |
| M000603C05 | r1m11-r2m8 | 520 | 8.17 | 77.0 | ✓ | 523.1 |
| M000603D04 | r1m11-r2m22 | 496 | 7.09 | 76.2 | ✓ | 497.1 |
| M000603D05 | r1m11-r2m24 | 446 | 8.32 | 69.3 | ✓ | 447.0 |
| M000603E04 | r1m12-r2m4 | 528 | 8.43 | 62.7 | ✓ | 529.1 |
| M000603E05 | r1m12-r2m5 | 467 | 6.32 | 70.1 | ✓ | 468.0 |
| M000603F04 | r1m12-r2m18 | 422 | 6.99 | 75.1 | ✓ | 423.3 |
| M000603F05 | r1m12-r2m20 | 392 | 6.64 | 76.6 | ✓ | 392.8 |
| M000603G04 | r1m12-r2m60 | 398 | 7.56 | 74.3 | ✓ | 399.3 |
| M000603G05 | r1m12-r2m62 | 382 | 6.10 | 58.3 | ✓ | 383.2 |

EXAMPLE 2
Detailed Synthesis of Lead Compound A4
This compound was also designated M12836152 (compound 7). The synthesis is summarised in Reaction Scheme 2.
Reaction Scheme 2
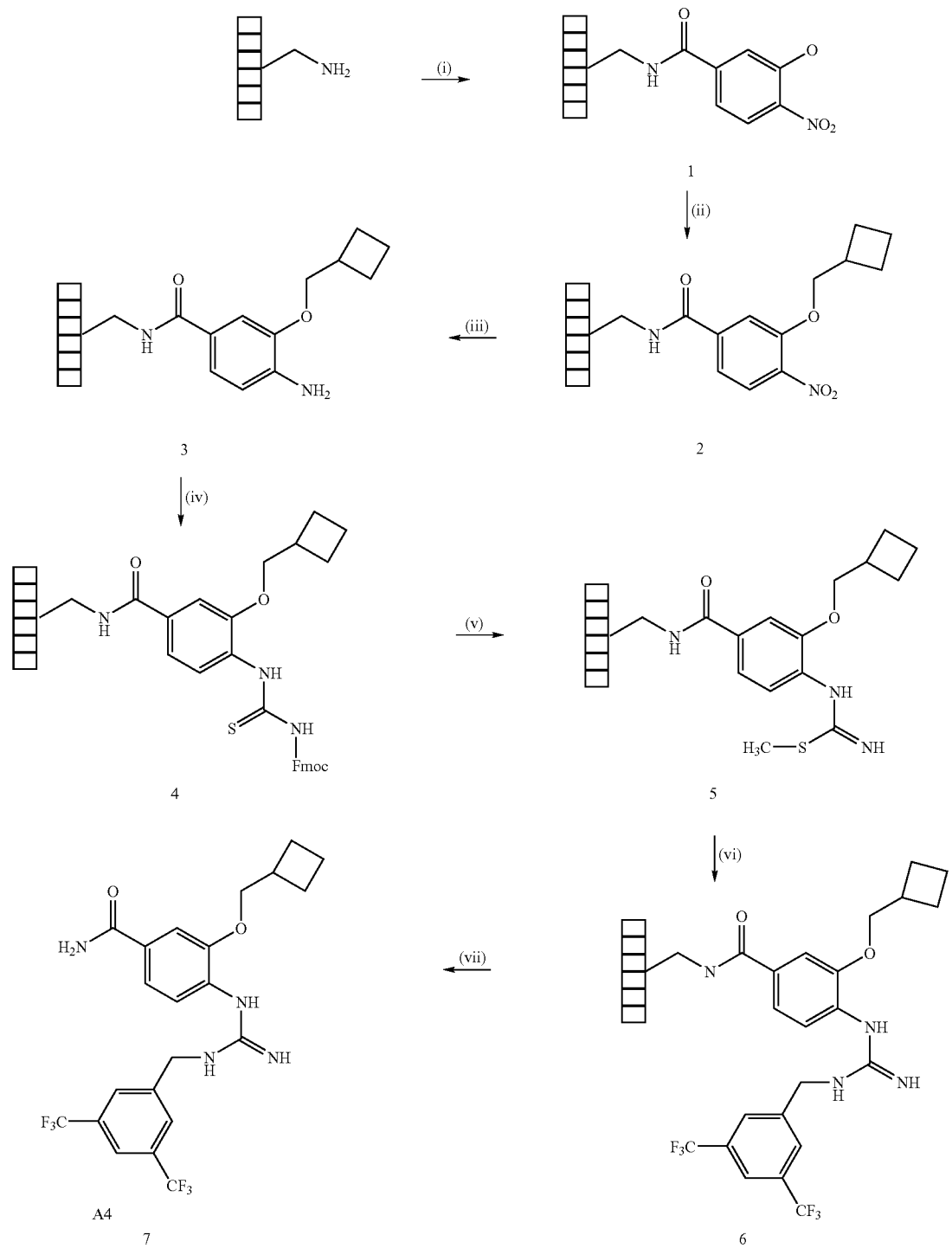

In Reaction Scheme 2: (i) DIC, DMAP, $CH_2Cl_2$, rt, 16 h; (ii) KH t DMF, 100° C., 24 h; (iii) $SnCl_2.2H_2O$, DMF, rt, 24 h; (iv) FmocNCS, $CH_2Cl_2$, rt, 7 h; (v) 20% piperidine/DMF, rt, 40 min, 1 h 20 min, then $CH_3I$, DMF, 40 min x2; (vi) DMSO, 75-85° C., 9 h; (vii) 20% TFA/$CH_2Cl_2$, rt, 1 h.

Synthesis of (1)

100 PS-D-RAM SynPhase™ Lanterns (batch 1703-13A, loading capacity 35 µmol) with Rink amide linker attached were Fmoc-deprotected using a solution of premixed 20% piperidine/DMF (v/v) (2×40 min). The piperidine solution was filtered off and the Lanterns washed with DMF (5×20 min) and $CH_2Cl_2$ (2×10 min).

80 mL of a solution of 3-hydroxy-4-nitrobenzoic acid (0.2M), DIC (0.1M) and DMAP (0.05M) in $CH_2Cl_2$ was prepared. The solution was allowed to stand at rt for 3 min then was added to the Fmoc-deprotected Lanterns. The Lanterns were stood at rt for 16 h. The reaction solution was then drained and the Lanterns washed with $CH_2Cl_2$ (4×20 min), DMF (8×20 min). Concomitantly-formed ester were then cleaved using alternate solutions of 10% ethanolamine/DMF (v/v) (15 min) and DMF (10 min) until clear spent washing solutions were obtained—approximately 6 cycles. The Lanterns were then washed with 50% $CH_3COOH$/$CH_2Cl_2$ (v/v) (2×10 min) then $CH_2Cl_2$ (3×10 min) and vacuum dried at 40° C. for 1 hour.

Synthesis of (2)

The Lanterns from step (i) were subjected to treatments with a slurry of excess potassium hydride (freshly extracted with petroleum ether from mineral oil) in anhydrous DMF for 30 min and 5 min respectively.

40 mL of a solution of (bromomethyl)cyclobutane (1.0M) and $Cs_2CO_3$ (0.3M) in anhydrous DMF was prepared. The KH-treated Lanterns were then added to this reaction solution and left to stand at 100° C. for 24 h. The reaction solution was drained and the Lanterns transferred to a clean vessel. The Lanterns were washed with DMF (3×10 min), 50% DMF/$H_2O$ (v/v) (2×30 min), DMF (2×10 min) and $CH_2Cl_2$ (4×10 min) then vacuum dried at 40° C. for 1 hour.

Synthesis of (3)

40 mL of a solution of tin(II)chloride dihydrate (1M) in DMF (distilled grade) was prepared. This solution was then added to the Lanterns from step (ii) and stood at rt for 24 h. The reaction solution was drained and the Lanterns washed with DMF (2×5 min), 20% $H_2O$/THF (2×30 min, 1×15 min), THF (1×15 min) and $CH_2Cl_2$ (4×15 min) then air dried overnight. HPLC (214 nm) $t_R$ 4.86 (89.9%) min; LC/MS $t_R$ 4.92 (220.9, $[M+H]^+$; 441.3, $[2M+H]^+$).

Synthesis of (4)

30 mL of a solution of FmocNCS (0.2M) in $CH_2Cl_2$ was prepared. The reaction solution was added to 50 Lanterns from step (iii) and the Lanterns stood at rt for 6.5 h, then heated to 40° C. for the final 0.5 h (total of 7 h reaction time). At the conclusion of the reaction, the FmocNCS solution was drained and the Lanterns washed with $CH_2Cl_2$; (4×10 min), DMF (2×10 min). These Lanterns were taken immediately to step (v).

Synthesis of (5)

The Lanterns were firstly treated with 20% piperidine/DMF (v/v) at rt (2 treatments of 40 min and 1 h 20 min respectively—there were no washes in between treatments). The second piperidine solution was drained and the Lanterns washed with DMF (4×10 min). The lanterns were further reacted immediately.

A solution of iodomethane (0.2M) in DMF was prepared and added to the Fmoc-deprotected Lanterns. The Lanterns were allowed to stand at rt for 40 min. The iodomethane solution was then removed and the Lanterns subjected to a second solution of iodomethane (0.2M) in DMF for 40 min—there were no washes in between treatments. After the 40 min was complete, the reaction solution was drained and the Lanterns washed with DMF (5×10 min) and DMSO (1×10 min). The Lanterns were taken immediately to step (vi).

Synthesis of (6)

The Lanterns from step (v) were added to a solution of 3,5-bis(trifluoromethyl) benzylamine (2.0M) in DMSO then placed in an oven set to 75° C. for 8.5 h. The temperature of the oven was then increased to 85° C. and the Lanterns reacted for a further 0.5 h. At the completion of the reaction, the amine solution was drained and the Lanterns washed with hot (85° C.) DMSO (2×10 min, 2×30 min), DMF (3×10 min) and $CH_2Cl_2$ (3×20 min). The Lanterns were then vacuum dried overnight.

Synthesis of (7)

The Lanterns were cleaved using a solution of 20% TFA/$CH_2Cl_2$ (v/v). The Lanterns were stood at rt for 1 h, then the cleavage solution was transferred to a 250 mL round bottom flask. The solution was evaporated under reduced pressure to give an orange oil. The oil was dissolved in 90% MeCN/$H_2O$ and evaporated a second time under reduced pressure, then dissolved again in neat acetonitrile and evaporated under reduced pressure to give an orange oil. The orange oil was then dissolved in neat acetonitrile and purified using preparative LC/MS techniques.

Reverse phase HPLC analysis was carried out using a Rainin Microsorb-MV C18 column (5 µm 100 Å; 50×4.6 mm), under the following conditions: Buffer A: 0.1% TFA in $H_2O$; Buffer B: 0.1% TFA in 90% MeCN/$H_2O$; Gradient: 0-100% Buffer B over 11 min; Flow rate: 1.5 mL/min; Wavelength detection: 214 and 254 nm. The target compound and potential by-products may have varying chromophores, so the HPLC results should not be taken as absolute, but they still give an indication of purity. Sample A4 was analyzed by HPLC using the manual integration method. The results are summarized in Table 6.

TABLE 6

Summary of HPLC results for compound A4

| Internal ID#: | Structure | MW* | Major peaks; $t_R$ at 214 nm (%) | Mass (mg) |
|---|---|---|---|---|
| A4 | 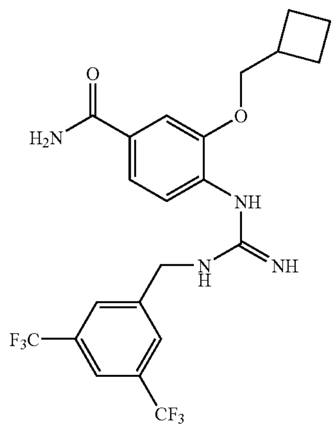 | 488.4 | 7.69, 96.6% | 10 MG |

*Molecular weight based on relative atomic mass Mass spectral analysis of A4 was carried out LC/MS on a Perkin-Elmer Sciex API-100 instrument, using the following conditions.

LC: Reverse Phase HPLC analysis
   Column: Monitor 5 μm C18 50×4.6 mm
   Solvent A: 0.1% TFA in water
   Solvent B: 0.1% TFA in 90% aqueous acetonitrile
   Gradient: 0-100% B over 11.0 min
   Flow rate: 1.5 mL/min
   Wavelength: 214 nm and 254 nm
MS: Ion Source: Ionspray
   Detection: Ion counting
   Flow rate to the mass spectrometer: 300 μL/min after split from column
(1.5 mL/min).
The results are summarised in Table 7.

TABLE 7

Summary of MS data from LC/MS analysis of compound A4

| Internal ID | Molecular Formula | Exact Mass (*EM) | Observed Ions |
|---|---|---|---|
| A4 | $C_{22}H_{22}F_6N_4O_2$ | 488.16 | 489.2 $[M + H]^+$ |

*Based on most abundant isotope

The local maxima were indicated on the main peaks. (M+H), the protonated molecular ion, was observed, together with other ions, some of which were considered to be artifacts of the MS.

Sample A4 was purified by preparative LC/MS on a Nebula instrument with a Waters XTerraMS column (19×50 mm, 5 μm, C18), using the following gradient: 5% B to 95% B over 4 min at 20 ml/min:
0 min 0% B
1 min 5% B
5 min 95% B
6 min 95% B System equilibration

EXAMPLE 3

Synthesis of a Library of Guanidine Amide Compounds (Library M0003)

Library M0003 is a single compound library of 50 guanidine amides, in which there is one point of diversity. The scaffold for this library is illustrated in formula III

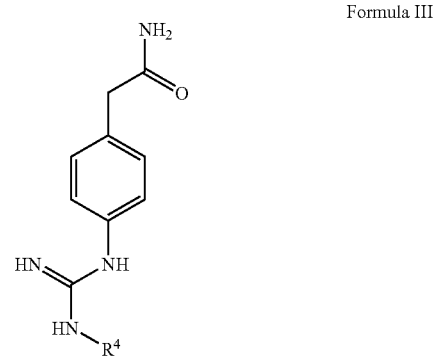

Formula III

Scaffold for Library M0003 in which $R^4$ is derived from a primary amine. This represents a subset of formula I in which A is methylene, $R^1$ is amino, $R^2$ is hydrogen, G is absent, $R^3$ is H and $R^4$ is derived from a primary amine. The library has been synthesised using 50 primary amines for the $R^4$ substituents. The purity, as estimated by RP-HPLC at 214 nm, of compounds from Library M0003 averages 78.3% and ranges from 0% to 91% (s.d.=12%), determined from analysis of all 50 compounds in the library.

Synthesis

The synthesis was based on a literature method, (Kearney et al., 1998) and is summarised in Reaction Scheme 3.

Reaction Scheme 3

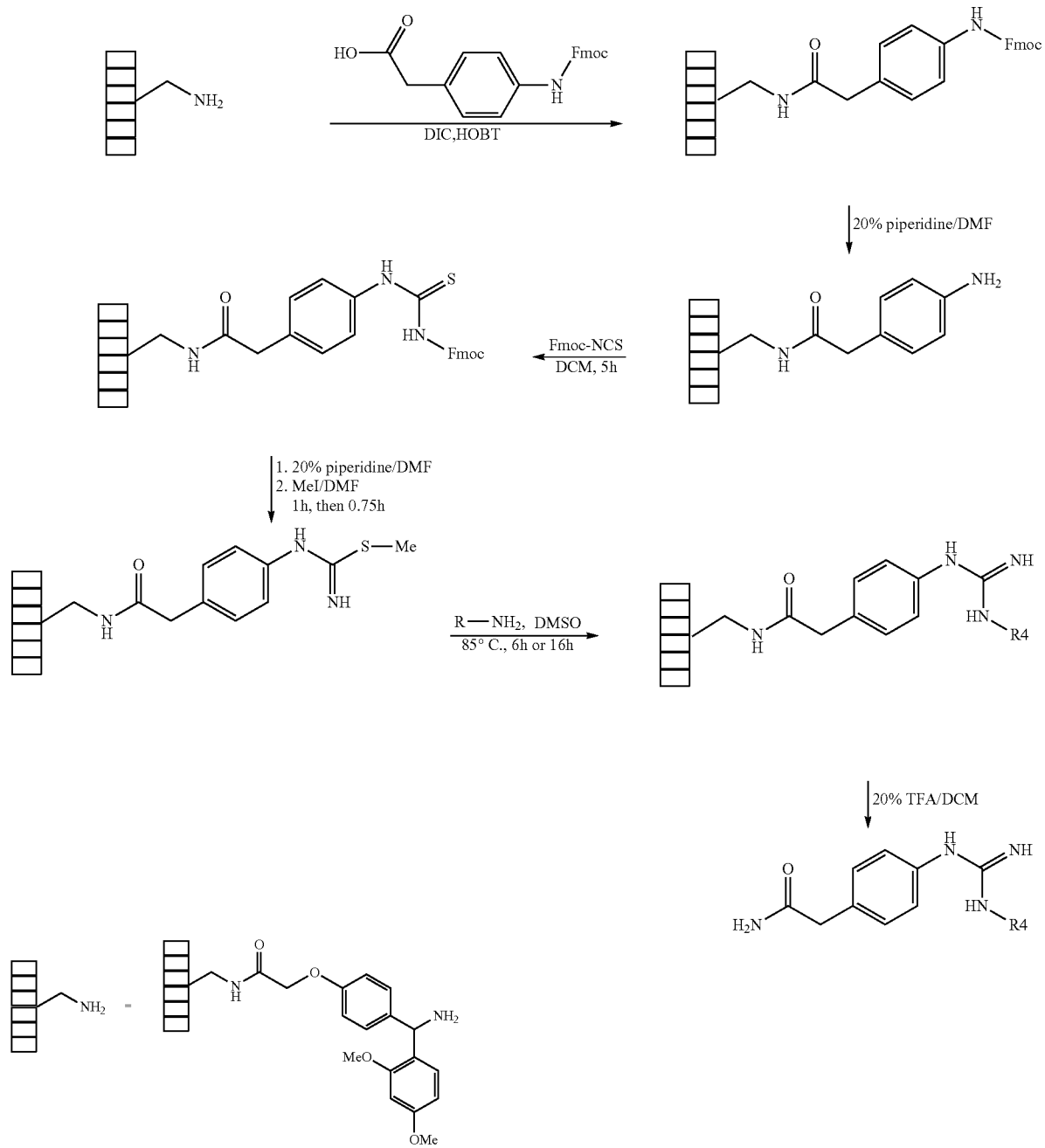

Reaction Scheme for Library M0003
R—NH₂ represents the primary amine coresponding to R⁴.

Fmoc-protected 4-aminophenylacetic acid was coupled on to PS Rink Lanterns (loading: 36 μmol) using DIC and HOBt. The Fmoc protecting group was then removed with piperidine/DMF. The resultant aniline was then treated with Fmoc-NCS, then Fmoc deprotected. The thiourea-functionalised Lanterns thus formed were then S-methylated with iodomethane. Subsequent reaction with 50 different primary amines followed by cleavage from the solid phase using 20% TFA/DCM afforded the 50 secondary guanidines comprising Library M0003.

(i) Preparation of the Fmoc-Protected 4-Aminophenylacetic Acid

A solution of 4-aminophenylacetic acid (5.0 g, 33.1 mmol) in warm DMF (35 mL) was prepared under nitrogen. The solution was then heated to 75° C., then FmocCl (4.24 g, 16.4 mmol) was added in 4 portions over 5 minutes. The resultant mixture was then stirred at 75° C. for 45 minutes. The solution was cooled to room temperature, then a solution of 1M HCl (100 mL) was added. The precipitate which formed was collected via vacuum filtration and washed with 3 portions of deionised water (2×50 mL, 1×100 mL). The solid collected was then vacuum dried overnight at 30° C., then for 2 h at 50° C. to yield Fmoc-4-aminophenylacetic acid (5.39 g; 44%) as a beige solid.

(ii) Coupling of the Fmoc-Protected 4-Aminophenylacetic Acid to Fmoc-Protected Rink PS Lanterns 75 PS Rink D-series Lanterns (batch 1531, loading: 36 μmol) were Fmoc deprotected by double treatment with 20% piperidine/DMF for 40 min and 30 min respectively. The second piperidine solution was removed and the Lanterns washed with DMF (3×10 min), 50% DMF/DCM (3×10 min) and DCM (3×10 min).

A solution of Fmoc-4-aminophenylacetic acid (0.098M), HOBt.H$_2$O (0.12M) and DIC (0.2M) in 20% DMF/DCM was prepared. To this solution was added the Fmoc-deprotected Lanterns. The mixture was then gently agitated at room temperature for 21 h. At the completion of the reaction, the coupling solution was removed and the Lanterns washed with DMF (3×10 min), 50% DMF/DCM (3×10 min) and DCM (3×10 min). The Lanterns were air-dried overnight.

The Fmoc group was then removed by treating the Lanterns with a solution of 20% piperidine/DMF at room temperature for 5 hours. Two Lanterns were subjected to a loading determination, the result for which was determined to be 33.9 μmol. The piperidine solution was removed and the Lanterns were washed with DMF (3×10 min), 50% DMF/DCM (3×10 min) and DCM (3×10 min).

(iii) Reaction with Fmoc-NCS and Iodomethane

A solution of Fmoc-NCS (0.2M) in DCM was prepared (50 mL). The 75 Lanterns from step (ii) were added and allowed to stand at room temperature for 5 h. The reaction solution was then drained and the Lanterns were washed with DCM (3×10 min), DMF (3×10 min) and DCM (3×10 min). The Lanterns were vacuum dried overnight at 40° C.

The Lanterns were again Fmoc-deprotected with 20% piperidine/DMF for 2.5 h. The piperidine solution was drained and the Lanterns washed with DMF (3×10 min) and DCM (3×10 min). The Lanterns were vacuum dried overnight at 45° C.

A solution of iodomethane (0.2M) in DMF (distilled) was prepared (50 mL). The Fmoc-deprotected Lanterns were added and then the contents were gently agitated at room temperature for 1 hour. A second solution of iodomethane (0.2M) in DMF was prepared. The first iodomethane solution was drained and the second iodomethane solution added immediately to the Lanterns. The Lanterns were then gently agitated at room temperature for a further 45 min. The iodomethane solution was drained and the Lanterns washed with DMF (3×10 min) and DCM (3×10 min). The Lanterns were then vacuum dried overnight at 35° C.

(iv) Guanidine Formation

Fifty solutions of the corresponding primary amines in DMSO (AR Grade) were prepared (50×1.25 mL). The primary amines used are summarized in Table 8. All amines were made up to 2M except amine #61, 3,5-dichlorobenzylamine (1M). Amine #45 (2-bromobenzylamine.HCl) was used with 1 equivalent of NaOH (for neutralisation). One Lantern from step (iii) was then added to each amine solution. The reaction solutions containing amines 31, 32, 33, 34 and 64 were heated to 85° C. for 16 h, whilst the remaining 45 solutions were heated to 85° C. for 6 h. At the completion of the reactions, the amine solutions were removed and the Lanterns washed with DMSO (2×10 min), DMF (3×10 min), 50% DMF/DCM (3×10 min) and DCM (3×10 min). The Lanterns were air-dried overnight at room temperature.

(v) Cleavage from the Solid Phase

Stems were attached to each Lantern and each Stem/Lantern assembly mounted onto a backing plate for cleavage. The Lanterns were then cleaved using 0.75 mL per Lantern of 10% TFA (distilled)/DCM for 1 h using a 96 well Bio-Rad® tray format. The resulting cleavage solutions were evaporated in vacuo using a centrifugal evaporator (GeneVac). The samples were then dissolved in 90% MeCN/H$_2$O (0.9 mL) for analysis.

Owing to the low yield of material obtained, the Lanterns were then re-cleaved using 0.75 mL of 20% TFA/DCM for 1 hour. The resulting cleavage solutions were evaporated in vacuo using a centrifugal evaporator. The dried samples were then dissolved in 90% MeCN/H$_2$O for analysis. After it was determined that the sets of compounds cleaved from the Lanterns in the two cleavages were identical, the stocks were combined into a single plate. The solutions were then evaporated in vacuo. The samples were then re-dissolved in 90% MeCN/H$_2$O and dispensed into a microtitre plate.

Analysis

All 50 compounds were analysed by reverse phase HPLC and electrospray mass spectrometry as described in Example 1. The results are summarised in Table 9. Compound M41698-32Y (r1m42) did not display the target molecular weight. However, this compound when subjected to amide hydrolysis conditions, as described in Example 4 below for Library M0004, afforded the corresponding acid in good purity.

TABLE 8

Summary of R$^4$-group structures and details for library M0003

| Fragment Tag | R$^4$ Group Structure | Reagent Name | Reagent Tag |
|---|---|---|---|
| r1m01 | 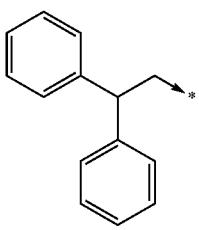 | 2,2-diphenylethylamine | DAC005 |

TABLE 8-continued

Summary of R⁴-group structures and details for library M0003

| Fragment Tag | R⁴ Group Structure | Reagent Name | Reagent Tag |
|---|---|---|---|
| r1m04 | 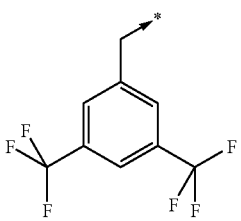 | 3,5-bis(trifluoromethyl)benzylamine | DAD005 |
| r1m05 | 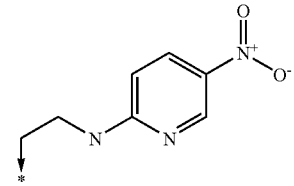 | 2-(2-aminoethylamino)-5-nitropyridine | DAG001 |
| r1m07 | 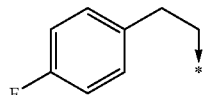 | 4-fluorophenethylamine | DAD023 |
| r1m08 | 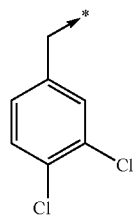 | 3,4-dichlorobenzylamine | DAD024 |
| r1m09 | 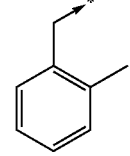 | 2-methylbenzylamine | DAC009 |
| r1m10 | 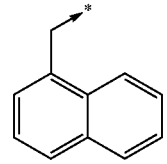 | 1-naphthalenemethylamine | DAC004 |
| r1m11 | 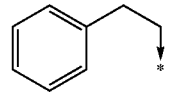 | 2-phenethylamine | DAC006 |
| r1m12 | 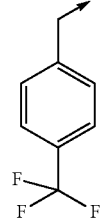 | 4-(trifluoromethyl)benzylamine | DAD006 |

TABLE 8-continued

Summary of R⁴-group structures and details for library M0003

| Fragment Tag | R⁴ Group Structure | Reagent Name | Reagent Tag |
|---|---|---|---|
| r1m13 | 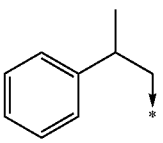 | 1-amino-2-phenylpropane b-phenethylamine | DAC008 |
| r1m14 | 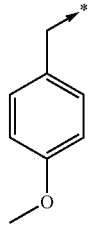 | 4-methoxybenzylamine | DAD003 |
| r1m16 | 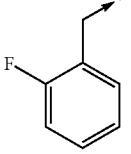 | 2-fluorobenzylamine | DAD004 |
| r1m17 | 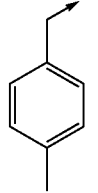 | 4-methylbenzylamine | DAC007 |
| r1m18 | 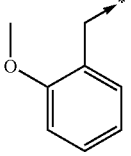 | 2-methoxybenzylamine | DAD009 |
| r1m20 | 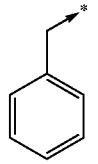 | benzylamine | DAC003 |
| r1m22 | 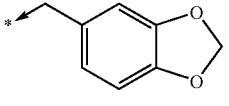 | piperonylamine | DAD002 |
| r1m24 | 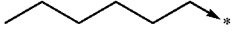 | hexylamine | DAA002 |
| r1m25 | 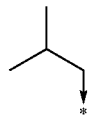 | isobutylamine | DAA010 |

TABLE 8-continued

Summary of R⁴-group structures and details for library M0003

| Fragment Tag | R⁴ Group Structure | Reagent Name | Reagent Tag |
|---|---|---|---|
| r1m26 | 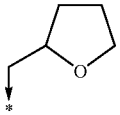 | (+/−)-tetrahydrofurfurylamine | DAB010 |
| r1m27 |  | allylamine | DAA005 |
| r1m30 | 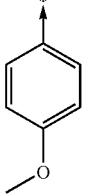 | 4-methoxyaniline | DAF002 |
| r1m31 | 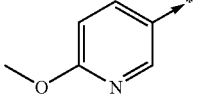 | 5-amino-2-methoxypyridine | DAG009 |
| r1m32 | 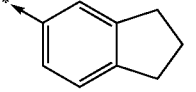 | 5-aminoindan | DAE003 |
| r1m33 | 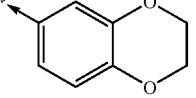 | 1,4-benzodioxan-6-amine | DAE001 |
| r1m34 | 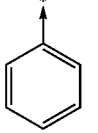 | aniline | DAE004 |
| r1m35 | 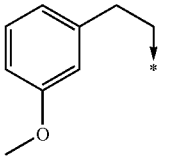 | 3-methoxyphenethylamine | DAD001 |
| r1m36 | 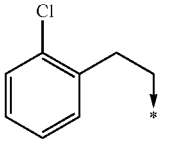 | 2-(2-chlorophenyl)ethylamine | DAD013 |
| r1m37 | 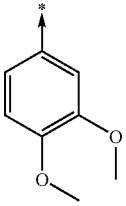 | 3,4-dimethoxyaniline | DAF007 |

TABLE 8-continued

Summary of R⁴-group structures and details for library M0003

| Fragment Tag | R⁴ Group Structure | Reagent Name | Reagent Tag |
|---|---|---|---|
| r1m38 | | 2-methoxyethylamine | DAB001 |
| r1m39 | | 2-methoxyphenethylamine | DAD017 |
| r1m40 | | 2-(4-chlorophenyl)ethylamine | DAD008 |
| r1m42 | | 1-(3-aminopropyl)imidazole | DAG006 |
| r1m43 | | ethylamine | DAA012 |
| r1m44 | | 2,5-difluorobenzylamine | DAD027 |
| r1m45 | | 2-bromobenzylamine | DAD028 |
| r1m46 | | 2-(trifluoromethyl)benzylamine | DAD029 |
| r1m48 | | 3,3-diphenylpropylamine | DAC011 |
| r1m51 | | 3-ethoxypropylamine | DAB021 |
| r1m52 | | 3-fluorophenethylamine | DAD033 |

TABLE 8-continued

Summary of R⁴-group structures and details for library M0003

| Fragment Tag | R⁴ Group Structure | Reagent Name | Reagent Tag |
|---|---|---|---|
| r1m53 | 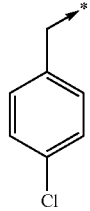 | 4-chlorobenzylamine | DAD034 |
| r1m56 | 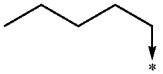 | 1-aminopentane | DAA005 |
| r1m57 | 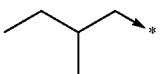 | 3-aminopentane | DAA019 |
| r1m58 | 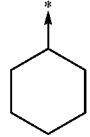 | cyclohexylamine | DAA001 |
| r1m59 | 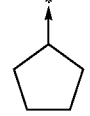 | cyclopentylamine | DAA006 |
| r1m60 | 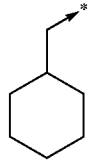 | cyclohexanemethylamine | |
| r1m61 | 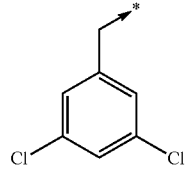 | 3,5-dichlorobenzylamine | DAD036 |
| r1m62 | 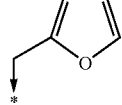 | furfurylamine | DAG005 |
| r1m63 | 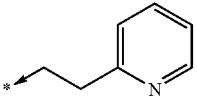 | 2-(aminoethyl)pyridine | DAG002 |
| r1m64 | 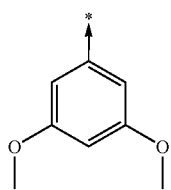 | 3,5-dimethoxyaniline | DAF009 |

TABLE 8-continued

Summary of R⁴-group structures and details for library M0003

| Fragment Tag | R⁴ Group Structure | Reagent Name | Reagent Tag |
|---|---|---|---|
| r1m65 | (CH₃)₂N-CH₂CH₂CH₂-* | 3-(dimethylamino)propylamine | DAA016 |

TABLE 9

Summary of Analytical Results

| Compound Identification | | | HPLC and LC-MS Data (214 nm) | | | |
|---|---|---|---|---|---|---|
| Compound ID | R Group | Monoisotopic FW | Retention Time (min) | Peak Area (%) | Target Found | (MH)+ Observed |
| M41698-1Y | r1m01 | 372 | 6.43 | 83.8 | ✓ | 373.4 |
| M41698-2Y | r1m04 | 418 | 6.94 | 84.5 | ✓ | 419.1 |
| M41698-3Y | r1m05 | 357 | 4.92 | 84.3 | ✓ | 357.9 |
| M41698-4Y | r1m07 | 314 | 5.27 | 84.3 | ✓ | 315.1 |
| M41698-5Y | r1m08 | 350 | 6.18 | 87.9 | ✓ | 350.9 |
| M41698-6Y | r1m09 | 296 | 5.10 | 86.8 | ✓ | 297.3 |
| M41698-7Y | r1m10 | 332 | 5.94 | 87.0 | ✓ | 333.1 |
| M41698-8Y | r1m11 | 296 | 5.08 | 43.4 | ✓ | 297.0 |
| M41698-9Y | r1m12 | 350 | 5.92 | 87.7 | ✓ | 351.2 |
| M41698-10Y | r1m13 | 310 | 5.48 | 86.3 | ✓ | 311.0 |
| M41698-11Y | r1m14 | 312 | 4.79 | 80.6 | ✓ | 313.1 |
| M41698-12Y | r1m16 | 300 | 4.61 | 88.1 | ✓ | 301.2 |
| M41698-13Y | r1m17 | 296 | 5.21 | 85.3 | ✓ | 297.1 |
| M41698-14Y | r1m18 | 312 | 5.08 | 86.0 | ✓ | 313.1 |
| M41698-15Y | r1m20 | 282 | 4.53 | 86.6 | ✓ | 282.9 |
| M41698-16Y | r1m22 | 326 | 4.64 | 86.0 | ✓ | 327.1 |
| M41698-17Y | r1m24 | 276 | 5.76 | 86.2 | ✓ | 277.0 |
| M41698-18Y | r1m25 | 248 | 4.12 | 83.5 | ✓ | 249.1 |
| M41698-19Y | r1m26 | 276 | 3.89 | 80.5 | ✓ | 277.0 |
| M41698-20Y | r1m27 | 232 | 3.36 | 69.2 | ✓ | 233.2 |
| M41698-21Y | r1m30 | 298 | 4.41 | 77.7 | ✓ | 299.1 |
| M41698-22Y | r1m31 | 299 | 3.80 | 78.7 | ✓ | 300.2 |
| M41698-23Y | r1m32 | 308 | 5.60 | 80.3 | ✓ | 309.1 |
| M41698-24Y | r1m33 | 326 | 4.44 | 81.5 | ✓ | 327.0 |
| M41698-25Y | r1m34 | 268 | 4.08 | 61.9 | ✓ | 269.0 |
| M41698-26Y | r1m35 | 326 | 5.20 | 69.1 | ✓ | 327.0 |
| M41698-27Y | r1m36 | 330 | 5.64 | 55.1 | ✓ | 331.0 |
| M41698-28Y | r1m37 | 328 | 4.22 | 58.9 | ✓ | 328.9 |
| M41698-29Y | r1m38 | 250 | 3.38 | 78.5 | ✓ | 251.0 |
| M41698-30Y | r1m39 | 326 | 5.48 | 77.3 | ✓ | 327.0 |
| M41698-31Y | r1m40 | 330 | 5.93 | 84.1 | ✓ | 330.9 |
| M41698-32Y | r1m42 | 300 | — | | | A — |
| M41698-33Y | r1m43 | 220 | 3.25 | 72.5 | ✓ | 221.2 |
| M41698-34Y | r1m44 | 318 | 4.74 | 91.0 | ✓ | 319.0 |
| M41698-35Y | r1m45 | 360 | 5.31 | 89.7 | ✓ | 350.9 |
| M41698-36Y | r1m46 | 350 | 5.46 | 88.0 | ✓ | 351.1 |
| M41698-37Y | r1m48 | 386 | 7.12 | 90.0 | ✓ | 387.2 |
| M41698-38Y | r1m51 | 278 | 4.04 | 82.8 | ✓ | 279.1 |
| M41698-39Y | r1m52 | 314 | 5.33 | 83.8 | ✓ | 315.1 |
| M41698-40Y | r1m53 | 316 | 5.47 | 89.2 | ✓ | 317.0 |
| M41698-41Y | r1m56 | 262 | 4.96 | 84.2 | ✓ | 263.1 |
| M41698-42Y | r1m57 | 262 | 4.37 | 78.6 | ✓ | 263.1 |
| M41698-43Y | r1m58 | 274 | 4.83 | 87.6 | ✓ | 275.1 |
| M41698-44Y | r1m59 | 260 | 4.25 | 86.2 | ✓ | 261.1 |
| M41698-45Y | r1m60 | 288 | 5.65 | 87.6 | ✓ | 289.2 |
| M41698-46Y | r1m61 | 350 | 6.14 | 83.3 | ✓ | 350.9 |
| M41698-47Y | r1m62 | 272 | 3.93 | 85.1 | ✓ | 273.0 |
| M41698-48Y | r1m63 | 297 | 2.89 | ᴮ79.8 | ✓ | 298.2 |
| M41698-49Y | r1m64 | 328 | 4.88 | 30.6 | ✓ | 329.0 |
| M41698-50Y | r1m65 | 277 | 2.63 | ᴮ72.9 | ✓ | 278.0 |

ᴬ No target ion found, m/z 223 observed.
ᴮ Co-elution of m/z 223 with target.

EXAMPLE 4

Synthesis of a Library of Guanidine Acid Compounds (Library M0004)

Library M0004 is a single compound library of 50 guanidine acids, in which there is one point of diversity. The scaffold for this library is shown in formula IV

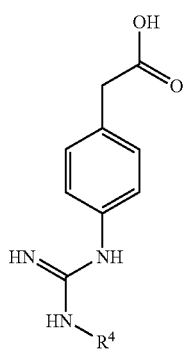

Formula IV

Scaffold for Library M0004 in which $R^4$ is derived from a primary amine. Thus this library represents a subset of compounds of formula I in which A is methylene, $R^1$ is hydroxyl, $R^2$ is hydrogen, G is absent, $R^3$ is H and $R^4$ is derived from a primary amine. The library was synthesised using 50 different primary amines for the $R^4$ substituents. This library was derived from library M0003 by splitting the amide products derived from that library, then hydrolysing one set to the corresponding acids. The purity, as estimated by RP-HPLC at 214 nm, of compounds from Library M0004 averages 74.8%, and ranges from 13% to 90% (s.d.=18%) determined from analysis of all 50 compounds in the library.

Synthesis

The synthesis was based on a literature method (Kearney et al., 1980), and is summarised in Reaction Scheme 4.

Fmoc-protected 4-aminophenylacetic acid was coupled onto PS Rink Lanterns (loading: 36 μmol) using DIC and HOBt. The Fmoc protecting group was then removed with piperidine/DMF. The resultant aniline was then treated with Fmoc-NCS, then Fmoc deprotected.

The thiourea-functionalised Lanterns formed were then S-methylated with iodomethane. Subsequent reaction with 50 different primary amines followed by cleavage from the solid phase using 20% TFA/DCM afforded the 50 primary amide secondary guanidines, which were hydrolysed by treatment with TFA/H$_2$O to the corresponding acids comprising Library M0004.

Reaction Scheme 4

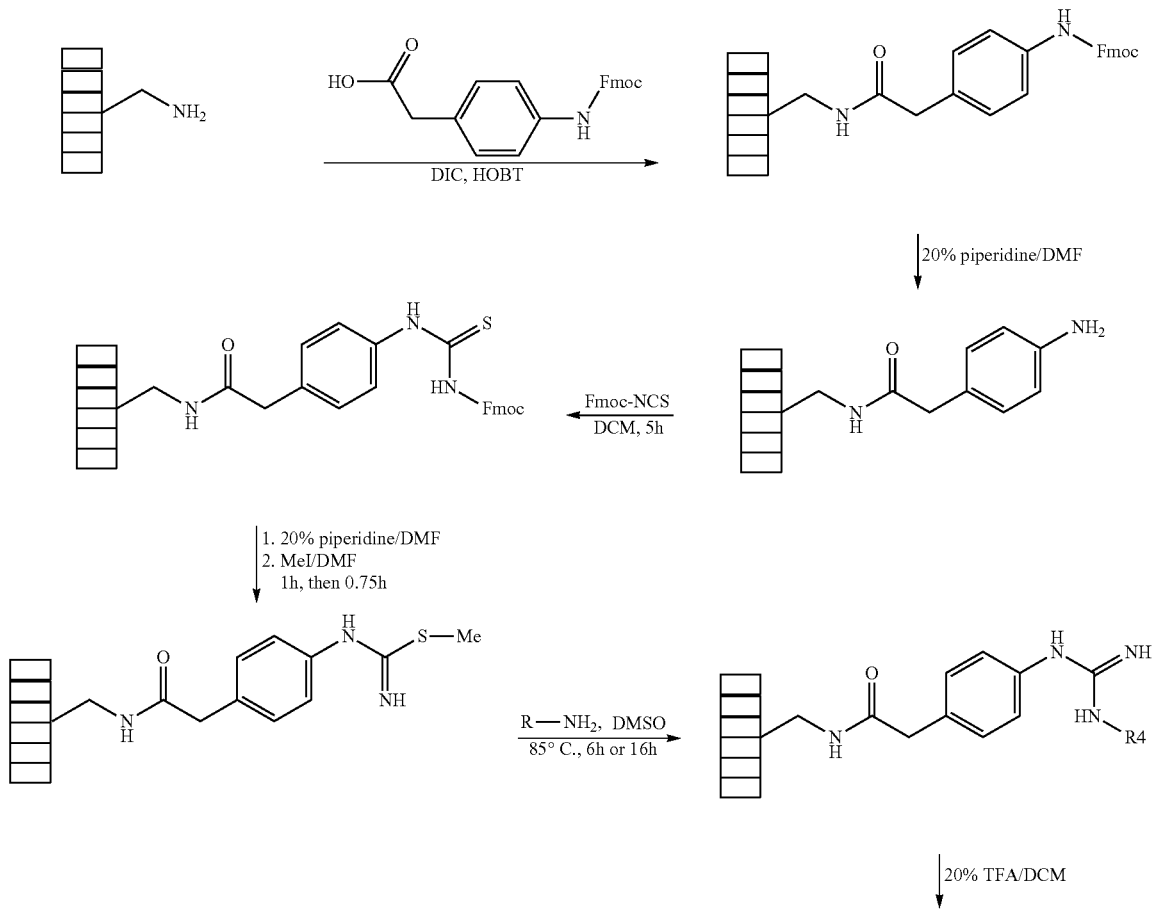

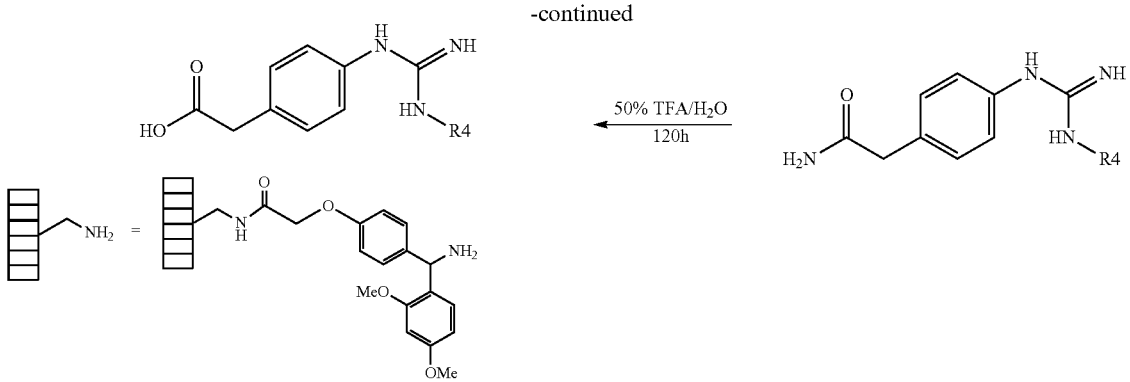

Reaction Scheme for Library M0004
R—NH₂ represents the primary amine coresponding to R₄.

(i) Preparation of the Fmoc-Protected 4-Aminophenylacetic Acid

A solution of 4-aminophenylacetic acid (5.0 g, 33.1 mmol) in warm DMF (35 mL) was prepared under nitrogen. The solution was heated to 75° C., then FmocCl (4.24 g, 16.4 mmol) was added in 4 portions over a 5 min period. The mixture was then stirred at 75° C. for 45 minutes, cooled to room temperature, and a solution of 1M HCl (100 mL) added. The precipitate which formed was collected via vacuum filtration and washed with 3 portions of deionised water (2×50 mL, 1×100 mL). The solid collected was then vacuum dried overnight at 30° C., then for 2 h at 50° C. to yield the title compound 5.39 g (44%) as a beige solid.

(ii) Coupling of the Fmoc-Protected 4-Aminophenylacetic Acid to Fmoc-Protected Rink PS Lanterns 75 PS Rink D-series Lanterns (batch 1531, loading: 36 µmol) were Fmoc deprotected by double treatment with 20% piperidine/DMF for 40 min and 30 min respectively. The second piperidine solution was removed and the Lanterns washed with DMF (3×10 min), 50% DMF/DCM (3×10 min) and DCM (3×10 min).

A solution of Fmoc-4-aminophenylacetic acid (0.098M), HOBt.H₂O (0.12M) and DIC (0.2M) in 20% DMF/DCM was prepared. To this solution was added the Fmoc-deprotected Lanterns. The mixture was then gently agitated at room temperature for 21 h. At the completion of the reaction, the Lanterns were drained and washed with DMF (3×10 min), 50% DMF/DCM (3×10 min) and DCM (3×10 min), then air-dried overnight.

The Fmoc group was removed by treating the Lanterns with a solution of 20% piperidine/DMF at room temperature for 5 hours. Two Lanterns were subjected to a loading evaluation test, the result for which was determined to be 33.9 µmol. The piperidine solution was removed and the Lanterns were washed with DMF (3×10 min), 50% DMF/DCM (3×10 min) and DCM (3×10 min).

(iii) Reaction with Fmoc-NCS and Iodomethane

A solution of Fmoc-NCS (0.2M) in DCM was prepared (50 mL). The 75 Lanterns from step (ii) were added and allowed to stand at room temperature for 5 h. The reaction solution was then drained and the Lanterns were washed with DCM (3×10 min), DMF (3×10 min) and DCM (3×10 min). The Lanterns were vacuum dried overnight at 40° C.

The Lanterns were Fmoc-deprotected with 20% piperidine/DMF for 2.5 h. The piperidine solution was drained and the Lanterns washed with DMF (3×10 min) and DCM (3×10 min). The Lanterns were vacuum dried overnight at 45° C.

A solution of iodomethane (0.2M) in DMF (distilled) was prepared (50 mL). The Fmoc-deprotected Lanterns were added and then the contents were gently agitated at room temperature for 1 hour. A second solution of iodomethane (0.2M) in DMF was prepared. The first iodomethane solution was drained and the second iodomethane solution added immediately to the Lanterns. The Lanterns were then gently agitated at room temperature for a further 45 min. The iodomethane solution was drained and the Lanterns washed with DMF (3×10 min) and DCM (3×10 min). The Lanterns were then vacuum dried overnight at 35° C.

(iv) Guanidine Formation

Fifty solutions of the corresponding primary amines in DMSO (AR Grade) were prepared (50×1.25 mL). The primary amines used are summarised in Table 10.

TABLE 10

Summary of R4-group structures and details for library M0004

| Fragment Tag | R⁴ Group Structure | Reagent Name | Reagent Tag |
|---|---|---|---|
| R1m01 | 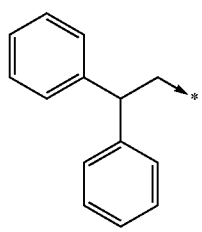 | 2,2-diphenylethylamine | DAC005 |

TABLE 10-continued

Summary of R4-group structures and details for library M0004

| Fragment Tag | R⁴ Group Structure | Reagent Name | Reagent Tag |
|---|---|---|---|
| R1m04 | 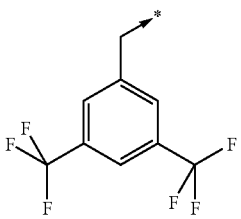 | 3,5-bis(trifluoromethyl)benzylamine | DAD005 |
| R1m05 | 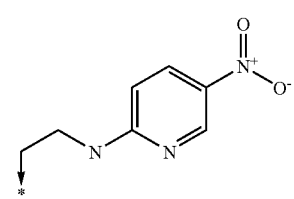 | 2-(2-aminoethylamino)-5-nitropyridine | DAG001 |
| R1m07 | 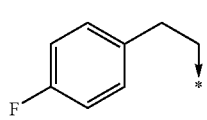 | 4-fluorophenethylamine | DAD023 |
| R1m08 | 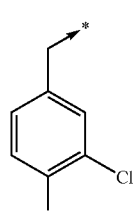 | 3,4-dichlorobenzylamine | DAD024 |
| R1m09 | 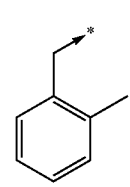 | 2-methylbenzylamine | DAC009 |
| R1m10 | 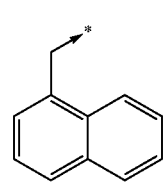 | 1-naphthalenemethylamine | DAC004 |
| R1m11 | 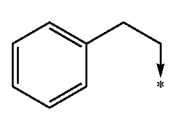 | 2-phenethylamine | DAC006 |
| R1m12 | 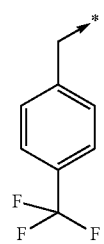 | 4-(trifluoromethyl)benzylamine | DAD006 |

TABLE 10-continued

Summary of R4-group structures and details for library M0004

| Fragment Tag | R⁴ Group Structure | Reagent Name | Reagent Tag |
|---|---|---|---|
| R1m13 | | 1-amino-2-phenylpropane b-phenethylamine | DAC008 |
| R1m14 | | 4-methoxybenzylamine | DAD003 |
| R1m16 | | 2-fluorobenzylamine | DAD004 |
| R1m17 | | 4-methylbenzylamine | DAC007 |
| R1m18 | | 2-methoxybenzylamine | DAD009 |
| R1m20 | | benzylamine | DAC003 |
| R1m22 | | piperonylamine | DAD002 |
| R1m24 | | hexylamine | DAA002 |
| R1m25 | | isobutylamine | DAA010 |

TABLE 10-continued

Summary of R4-group structures and details for library M0004

| Fragment Tag | R⁴ Group Structure | Reagent Name | Reagent Tag |
|---|---|---|---|
| R1m26 | 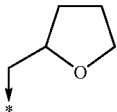 | (+/−)-tetrahydrofurfurylamine | DAB010 |
| R1m27 |  | allylamine | DAA005 |
| R1m30 | 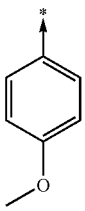 | 4-methoxyaniline | DAF002 |
| R1m31 | 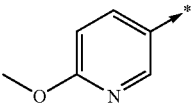 | 5-amino-2-methoxypyridine | DAG009 |
| R1m32 | 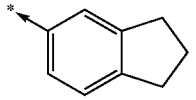 | 5-aminoindan | DAE003 |
| R1m33 | 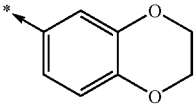 | 1,4-benzodioxan-6-amine | DAE001 |
| R1m34 | 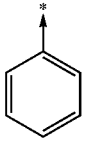 | aniline | DAE004 |
| R1m35 | 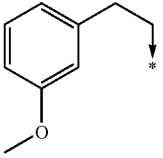 | 3-methoxyphenethylamine | DAD001 |
| R1m36 | 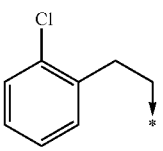 | 2-(2-chlorophenyl)ethylamine | DAD013 |
| R1m37 | 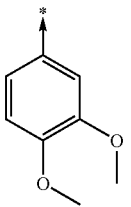 | 3,4-dimethoxyaniline | DAF007 |

TABLE 10-continued

Summary of R4-group structures and details for library M0004

| Fragment Tag | R$^4$ Group Structure | Reagent Name | Reagent Tag |
|---|---|---|---|
| R1m38 | | 2-methoxyethylamine | DAB001 |
| R1m39 | | 2-methoxyphenethylamine | DAD017 |
| R1m40 | | 2-(4-chlorophenyl)ethylamine | DAD008 |
| R1m42 | | 1-(3-aminopropyl)imidazole | DAG006 |
| R1m43 | | ethylamine | DAA012 |
| R1m44 | | 2,5-difluorobenzylamine | DAD027 |
| R1m45 | | 2-bromobenzylamine | DAD028 |
| R1m46 | | 2-(trifluoromethyl)benzylamine | DAD029 |
| R1m48 | | 3,3-diphenylpropylamine | DAC011 |
| R1m51 | | 3-ethoxypropylamine | DAB021 |
| R1m52 | | 3-fluorophenethylamine | DAD033 |

TABLE 10-continued

Summary of R4-group structures and details for library M0004

| Fragment Tag | R⁴ Group Structure | Reagent Name | Reagent Tag |
|---|---|---|---|
| R1m53 | 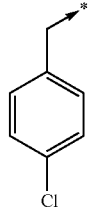 | 4-chlorobenzylamine | DAD034 |
| R1m56 | 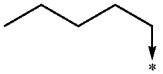 | 1-aminopentane | DAA005 |
| R1m57 | 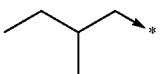 | 3-aminopentane | DAA019 |
| R1m58 | 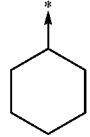 | cyclohexylamine | DAA001 |
| R1m59 | 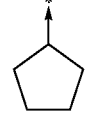 | cyclopentylamine | DAA006 |
| R1m60 | 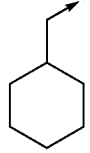 | cyclohexanemethylamine | DAA003 |
| R1m61 | 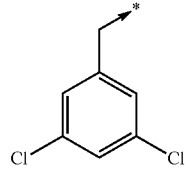 | 3,5-dichlorobenzylamine | DAD036 |
| R1m62 | 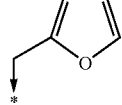 | furfurylamine | DAG005 |
| R1m63 | 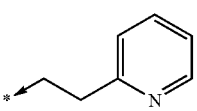 | 2-(aminoethyl)pyridine | DAG002 |
| R1m64 | 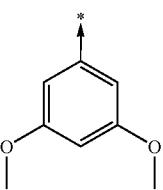 | 3,5-dimethoxyaniline | DAF009 |

TABLE 10-continued

Summary of R4-group structures and details for library M0004

| Fragment Tag | R⁴ Group Structure | Reagent Name | Reagent Tag |
|---|---|---|---|
| R1m65 | (structure) | 3-(dimethylamino)propylamine | DAA016 |

All amines were made up to 2M except amine #61, 3,5-dichlorobenzylamine (1M). Amine #45 (2-bromobenzylamine.HCl) was used with an equivalent of NaOH (to neutralise the hydrochloride salt). A Lantern from step (iii) was then added to each of the 50 amine solutions. The reaction solutions containing amines 31, 32, 33, 34 and 64 were heated to 85° C. for 16 h, whilst the remaining 45 solutions were heated to 85° C. for 6 h. At the completion of the reactions, the Lanterns were drained and washed with DMSO (2×10 min), DMF (3×10 min), 50% DMF/DCM (3×10 min) and DCM (3×10 min). The Lanterns were then air-dried overnight at room temperature.

(v) Cleavage from the Solid Phase

Stems were attached to each Lantern and each Stem/Lantern assembly mounted onto a backing plate for cleavage. The Lanterns were then cleaved using 0.75 mL per Lantern of 10% TFA (distilled)/DCM for 1 h using a 96 well Bio-Rad® tray format. The resulting cleavage solutions were evaporated in vacuo using a centrifugal evaporator (GeneVac). The samples were then dissolved in 90% MeCN/H₂O (0.9 mL) for analysis.

Owing to the low yield of material obtained, the Lanterns were then re-cleaved using 0.75 mL of 20% TFA/DCM for 1 h. The resulting cleavage solutions were evaporated in vacuo using a centrifugal evaporator. The dried samples were then dissolved in 90% MeCN/H₂O for analysis. After it was determined that the sets of compounds cleaved from the Lanterns in the two cleavages were identical, the stocks were combined into a single plate. The solutions were then evaporated in vacuo.

(vi) Amide Hydrolysis

The amide products above were dissolved in 90% MeCN/H₂O and half of the material in each well was dispensed into 50 new BioRad tubes and evaporated in vacuo. A solution of TFA/H₂O 1:1 (900 µL) was dispensed into each well, the tubes were capped and heated to 42° C. for 115 h. The samples were then concentrated, redissolved in 90% MeCN/H₂O and again concentrated then redissolved in 90% MeCN/H₂O and dispensed into a VMG plate.

Analysis

All 50 compounds were analyzed by reverse phase HPLC and electrospray mass spectrometry, as described in Example 1. The results are summarised in Table 11.

TABLE 11

Summary of Analytical Results

| Compound ID | R Group | Monoisotopic FW | Retention Time (min) | Peak Area (%) | Target Found | (MH)+ Observed |
|---|---|---|---|---|---|---|
| M0040101 | r1m01 | 373 | 7.01 | 87.2 | ✓ | 374.4 |
| M0040102 | r1m04 | 419 | 7.25 | 82.8 | ✓ | 420.2 |
| M0040103 | r1m05 | 358 | 5.21 | 86.0 | ✓ | 359.0 |
| M0040104 | r1m07 | 315 | 5.63 | 84.3 | ✓ | 315.9 |
| M0040105 | r1m08 | 351 | 6.41 | 88.0 | ✓ | 352.0 |
| M0040106 | r1m09 | 297 | 5.46 | 87.6 | ✓ | 298.2 |
| M0040107 | r1m10 | 333 | 6.25 | 82.6 | ✓ | 334.2 |
| M0040108 | r1m11 | 297 | 5.52 | 46.6 | ✓ | 298.5 |
| M0040109 | r1m12 | 351 | 6.24 | 87.3 | ✓ | 352.1 |
| M0040110 | r1m13 | 311 | 5.86 | 86.0 | ✓ | 312.1 |
| M0040111 | r1m14 | 313 | 5.31 | 12.9 | ✓ | 314.3 |
| M0040112 | r1m16 | 301 | 5.07 | 87.4 | ✓ | 302.2 |
| M0040113 | r1m17 | 297 | 5.59 | 85.8 | ✓ | 298.3 |
| M0040114 | r1m18 | 313 | 5.45 | 79.4 | ✓ | 313.9 |
| M0040115 | r1m20 | 283 | 4.98 | 86.1 | ✓ | 284.3 |
| M0040116 | r1m22 | 327 | 5.12 | 42.3 | ✓ | 328.1 |
| M0040117 | r1m24 | 277 | 6.14 | 82.8 | ✓ | 278.0 |
| M0040118 | r1m25 | 249 | 4.57 | 83.5 | ✓ | 249.9 |
| M0040119 | r1m26 | 277 | 4.25 | 78.1 | ✓ | 277.9 |
| M0040120 | r1m27 | 233 | 3.75 | 72.5 | ✓ | 233.9 |
| M0040121 | r1m30 | 299 | 4.78 | 72.7 | ✓ | 300.2 |
| M0040122 | r1m31 | 300 | 4.24 | 62.8 | ✓ | 301.2 |
| M0040123 | r1m32 | 309 | 6.03 | 85.0 | ✓ | 309.9 |
| M0040124 | r1m33 | 327 | 4.85 | 86.9 | ✓ | 328.0 |
| M0040125 | r1m34 | 269 | 4.48 | 53.1 | ✓ | 270.3 |
| M0040126 | r1m35 | 327 | 5.65 | 62.4 | ✓ | 328.3 |
| M0040127 | r1m36 | 331 | 6.06 | 51.3 | ✓ | 331.8 |
| M0040128 | r1m37 | 329 | 4.60 | 55.5 | ✓ | 330.0 |

TABLE 11-continued

Summary of Analytical Results

| Compound Identification | | | HPLC and LC/MS Data (214 nm) | | | |
|---|---|---|---|---|---|---|
| Compound ID | R Group | Monoisotopic FW | Retention Time (min) | Peak Area (%) | Target Found | (MH)+ Observed |
| M0040129 | r1m38 | 251 | 3.79 | 80.8 | ✓ | 252.0 |
| M0040130 | r1m39 | 327 | 5.87 | 73.3 | ✓ | 328.2 |
| M0040131 | r1m40 | 331 | 6.26 | 82.8 | ✓ | 332.3 |
| M0040132 | r1m42 | 301 | 2.98 | 89.8 | ✓ | 302.0 |
| M0040133 | r1m43 | 221 | 3.63 | 73.7 | ✓ | 222.4 |
| M0040134 | r1m44 | 319 | 5.15 | 86.2 | ✓ | 320.1 |
| M0040135 | r1m45 | 361 | 5.68 | 89.1 | ✓ | 361.9 |
| M0040136 | r1m46 | 351 | 5.94 | 86.8 | ✓ | 352.0 |
| M0040137 | r1m48 | 387 | 7.52 | 88.4 | ✓ | 388.2 |
| M0040138 | r1m51 | 279 | 4.49 | 81.7 | ✓ | 280.3 |
| M0040139 | r1m52 | 315 | 5.66 | 79.2 | ✓ | 316.0 |
| M0040140 | r1m53 | 317 | 5.80 | 87.0 | ✓ | 318.1 |
| M0040141 | r1m56 | 263 | 5.41 | 82.5 | ✓ | 264.1 |
| M0040142 | r1m57 | 263 | 4.82 | 67.9 | ✓ | 264.4 |
| M0040143 | r1m58 | 275 | 5.20 | 79.1 | ✓ | 276.3 |
| M0040144 | r1m59 | 261 | 4.69 | 81.8 | ✓ | 262.0 |
| M0040145 | r1m60 | 289 | 6.03 | 85.1 | ✓ | 290.1 |
| M0040146 | r1m61 | 351 | 6.42 | 75.4 | ✓ | 352.1 |
| M0040147 | r1m62 | 273 | 4.41 | 14.5 | ✓ | 273.9 |
| M0040148 | r1m63 | 298 | 3.05 | $^A$85.1 | ✓ | 299.4 |
| M0040149 | r1m64 | 329 | 5.30 | 32.1 | ✓ | 330.2 |
| M0040150 | r1m65 | 278 | 2.71 | $^B$79.3 | ✓ | 278.9 |

$^A$Co-elution of m/z 404.2 with target ion.
$^B$Co-elution of m/z 364.3 with target ion.

All compounds displayed the target molecular weight. The LC/MS results indicated that at least two ions were detected under each major peak. These are and $(MH+122)^+$. Additionally, there were ions corresponding to $[MH+(n\times222)]^+$, where n is an integer. An ion of m/z 222 was also detected in the buffer solution of the instrument.

EXAMPLE 5

Synthesis of a Library of Tertiary Guanidine Amide Compounds (Library M0007)

Library M0007 is a single compound library of 21 tertiary guanidine amides. The scaffold for this library is illustrated in formula V, in which both $R^3$ and $R^4$ are derived from primary amines, which may be the same or different.

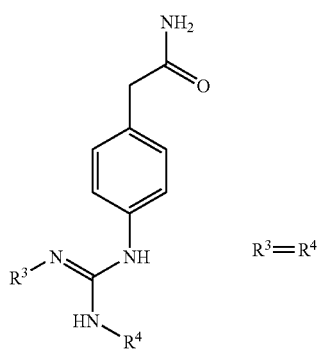

Scaffold for Library M0007

Formula V

Thus this represents a subset of formula I in which A is methylene, $R^1$ is amino, $R^2$ is hydrogen, G is absent, $R^3$ and $R^4$ are derived from a primary amine.

The library was synthesised using 21 different primary amines for the $R^3$ and $R^4$ substituents. The purity, as estimated by RP-HPLC at 214 nm, of compounds from Library M0007 averages 85.6%, and ranges from 73% to 92% (s.d.=5.5%), determined from analysis of all 21 compounds in the library.

The compounds were plated on the basis of 3.8 mg relative to the average mass obtained for the complete set of 21 compounds. The amount of compound per well was 8.8 μmol, based on an average molecular weight of 431 amu.

Synthesis

The synthesis is summarised in Reaction Scheme 5. Fmoc-protected 4-aminophenylacetic acid was coupled onto PS Rink Lanterns (loading: 36 μmol) using DIC and HOBt. The Fmoc protecting group was then removed with piperidine/DMF. The resultant aniline was then treated with Fmoc-NCS, then Fmoc deprotected. The thiourea functionalised Lanterns formed were then S-methylated with iodomethane. Subsequent reaction with 21 different primary amines followed by cleavage from the solid phase using 20% TFA/DCM afforded the 21 tertiary guanidines comprising Library M0007.

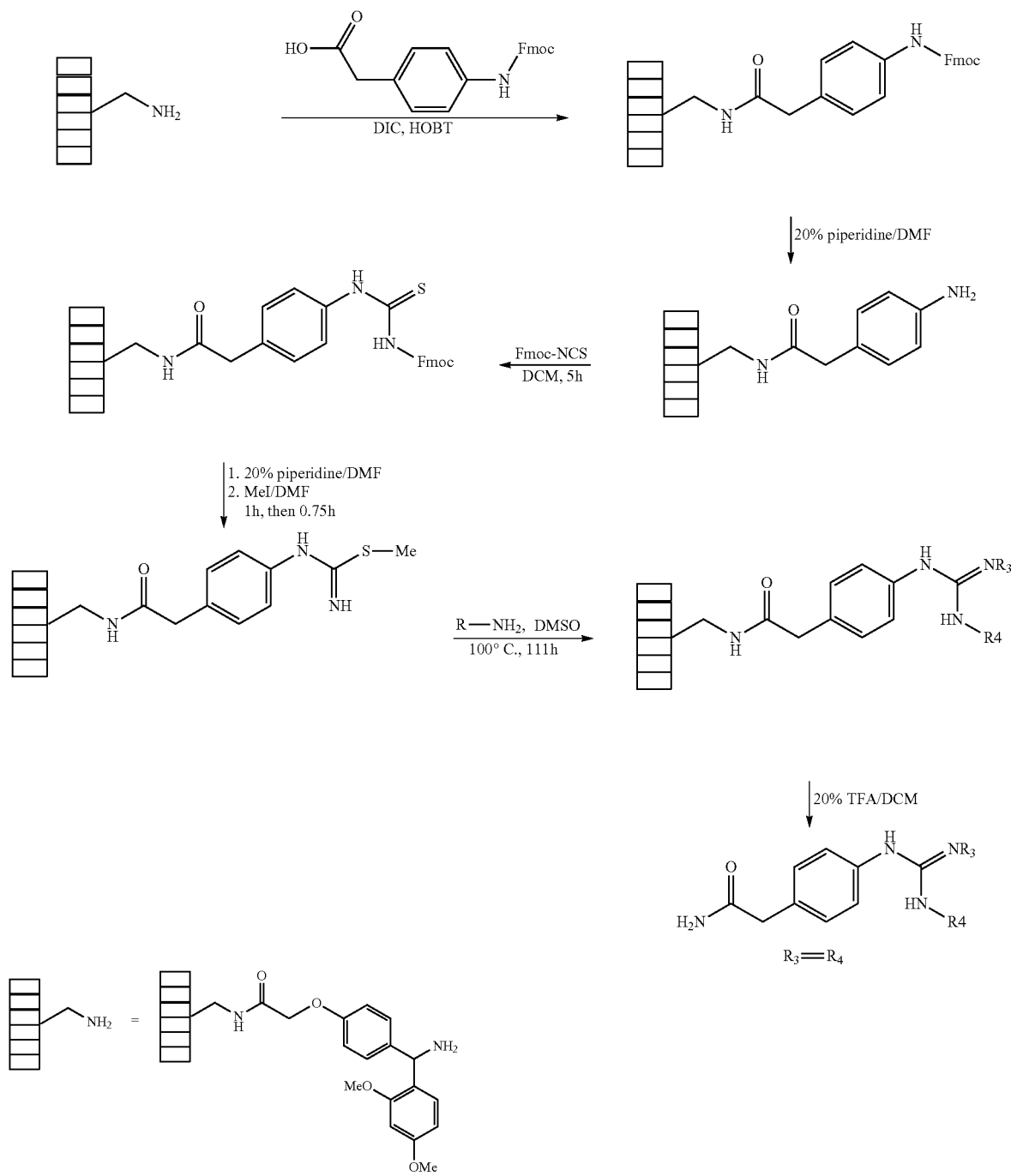

Reaction Scheme for Library M0007

R—NH₂ represents the primary amine coresponding to R₃, R₄.

(i) Preparation of the Fmoc-Protected 4-Aminophenylacetic Acid

A solution of 4-aminophenylacetic acid (5.0 g, 33.1 mmol) in warm DMF (35 mL) was prepared under $N_2$. The solution was then heated to 75° C., and FmocCl (4.24 g, 16.4 mmol) was added in 4 portions over 5 minutes. The resultant mixture was then stirred at 75° C. for 45 minutes. The solution was cooled to room temperature, then a solution of 1M HCl (100 mL) was added. The precipitate which formed was collected via vacuum filtration and washed with 3 portions of deionised water (2×50 mL, 1×100 mL). The solid collected was then vacuum dried overnight at 30° C., then for 2 h at 50° C. to yield Fmoc-4-aminophenylacetic acid (5.39 g; 44%) as a beige solid.

(ii) Coupling of the Fmoc-Protected 4-Aminophenylacetic Acid to Fmoc-Protected Rink PS Lanterns 50 PS Rink D-series Lanterns (batch 1531, loading: 36 μmol) were Fmoc deprotected by double treatment with 20% piperidine/DMF for 40 min and 30 min. The second piperidine solution was removed and the Lanterns were washed with DMF (3×10 min), 50% DMF/DCM (3×10 min) and DCM (3×10 min).

A solution of Fmoc-4-aminophenylacetic acid (0.098M), HOBt.$H_2O$ (0.12M) and DIC (0.2M) in 20% DMF/DCM was prepared. To this solution was added the Fmoc-deprotected Lanterns. The mixture was then gently agitated at room temperature for 21 h. At the completion of the reaction, the coupling solution was removed and the Lanterns washed with DMF (3×10 min), 50% DMF/DCM (3×10 min) and DCM (3×10 min). The Lanterns were air-dried overnight.

The Fmoc group was then removed by treating the Lanterns with a solution of 20% piperidine/DMF at room temperature for 5 hours. Two Lanterns were subjected to a loading determination, result: 33.9 μmmol (average). The piperidine solution was removed and the Lanterns were washed with DMF (3×10 min), 50% DMF/DCM (3×10 min) and DCM (3×10 min).

(iii) Reaction with Fmoc-NCS and Iodomethane

A solution of Fmoc-NCS (0.2M) in DCM was prepared. The Lanterns from step (ii) were added to this solution and allowed to stand at room temperature for 5 h. The reaction solution was then drained and the Lanterns were washed with DCM (3×10 min), DMF (3×10 min) and DCM (3×10 min). The Lanterns were vacuum dried overnight at 40° C.

The Lanterns were again Fmoc-deprotected, with 20% piperidine/DMF for 2.5 h. The piperidine solution was drained and the Lanterns washed with DMF (3×10 min) and DCM (3×10 min). The Lanterns were vacuum dried overnight at 45° C.

A solution of iodomethane (0.2M) in DMF (distilled) was prepared. The Fmoc-deprotected Lanterns were added and then the contents were gently agitated at room temperature for 1 hour. A second solution of iodomethane (0.2M) in DMF was prepared. The first iodomethane solution was drained and the second iodomethane solution added immediately to the Lanterns. The Lanterns were then gently agitated at room temperature for a further 45 min. The iodomethane solution was drained and the Lanterns washed with DMF (3×10 min) and DCM (3×10 min). The Lanterns were then vacuum dried overnight at 35° C.

(iv) Tertiary Guanidine Formation

Solutions (4M) of the primary amines in DMSO (AR Grade) were prepared (1.25 mL). The amines used are summarized in Table 12. One Lantern from step (iii) was then added to each amine solution. The reaction solutions were heated to 100° C. for 111 h. At the completion of the reactions, the amine solutions were removed and the Lanterns washed with DMSO (2×10 min), DMF (3×10 min), 50% DMF/DCM (3×10 min) and DCM (3×10 min). The Lanterns were air-dried overnight at room temperature.

(v) Cleavage from the Solid Phase

Cleavage Stems were manually attached to each Lantern and each Stem/Lantern assembly mounted onto a backing plate for cleavage. The Lanterns were then cleaved using 0.75 mL per Lantern of 10% TFA (distilled)/DCM for 1 h using a 96 well Bio-Rad® tray format. The resulting cleavage solutions were evaporated in vacuo using a centrifugal evaporator (GeneVac). The samples were then dissolved in 90% MeCN/$H_2O$ (0.9 mL) for analysis.

Since the Lanterns had been inadvertently cleaved with 10% TFA/DCM instead of 20% TFA/DCM, the Lanterns were then re-cleaved using 0.75 mL of 20% TFA/DCM for 1 hour. The resulting cleavage solutions were evaporated in vacuo using a centrifugal evaporator. The dried samples were then dissolved in 90% MeCN/$H_2O$ for analysis. After it was determined that the sets of compounds cleaved from the Lanterns in the two cleavages were essentially identical, the stocks were combined into a single plate. The solutions were then evaporated in vacuo. The samples were then re-dissolved in 90% MeCN/$H_2O$, re-analysed and dispensed into a microtitre plate.

Analysis

All 21 compounds were analysed by reverse phase HPLC and electrospray mass spectrometry as described in Example 1. All compounds displayed the target molecular weight. The results are summarised in Table 13.

TABLE 12

Summary of $R^3$ and $R^4$ group structures and details for library M0007

| Fragment Tag | $R^3$ and $R^4$ Group Structure | Reagent Name | Reagent Tag |
| --- | --- | --- | --- |
| r1m01 | 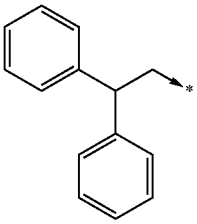 | 2,2-diphenylethylamine | DAC005 |
| r1m04 | 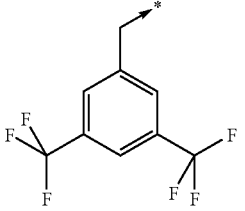 | 3,5-bis(trifluoromethyl)benzylamine | DAD008 |

TABLE 12-continued

Summary of $R^3$ and $R^4$ group structures and details for library M0007

| Fragment Tag | $R^3$ and $R^4$ Group Structure | Reagent Name | Reagent Tag |
|---|---|---|---|
| r1m07 | 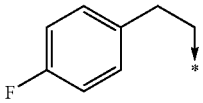 | 4-fluorophenethylamine | DAD023 |
| r1m08 | 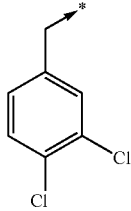 | 3,4-dichlorobenzylamine | DAD024 |
| r1m09 | 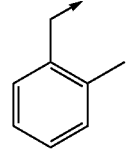 | 2-methylbenzylamine | DAC009 |
| r1m10 | 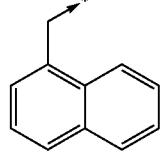 | 1-naphthalenemethylamine | DAC004 |
| r1m11 | 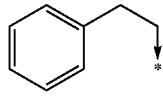 | 2-phenethylamine | DAC006 |
| r1m12 | 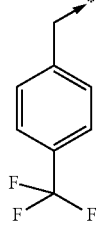 | 4-(trifluoromethyl)benzylamine | DAD006 |
| r1m13 | 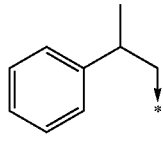 | 1-amino-2-phenylpropane (beta-phenethylamine) | DAC008 |
| r1m14 | 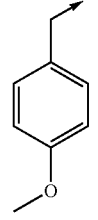 | 4-methoxybenzylamine | DAD003 |

TABLE 12-continued

Summary of $R^3$ and $R^4$ group structures and details for library M0007

| Fragment Tag | $R^3$ and $R^4$ Group Structure | Reagent Name | Reagent Tag |
|---|---|---|---|
| r1m16 | 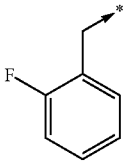 | 2-fluorobenzylamine | DAD004 |
| r1m17 | 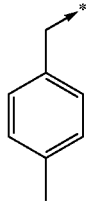 | 4-methylbenzylamine | DAC007 |
| r1m18 | 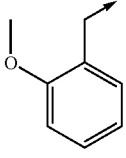 | 2-methoxybenzylamine | DAD009 |
| r1m20 | 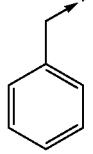 | benzylamine | DAC003 |
| r1m22 | 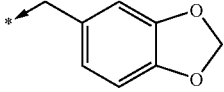 | piperonylamine | DAD002 |
| r1m24 | 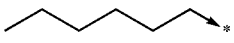 | hexylamine | DAA002 |
| r1m25 | 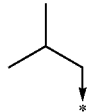 | isobutylamine | DAA010 |
| r1m26 | 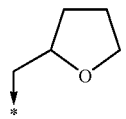 | (+/−)-tetrahydrofurfurylamine | DAB010 |
| r1m27 |  | allylamine | DAA005 |
| r1m40 | 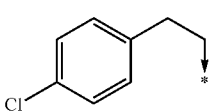 | 2-(4-chlorophenyl)ethylamine | DAD008 |

TABLE 12-continued

Summary of $R^3$ and $R^4$ group structures and details for library M0007

| Fragment Tag | $R^3$ and $R^4$ Group Structure | Reagent Name | Reagent Tag |
|---|---|---|---|
| r1m44 | 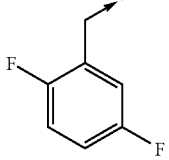 | 2,5-difluorobenzylamine | DAD027 |

TABLE 13

Summary of Analytical Results: Library M0007

| Compound Identification | | | HPLC and LC-MS Data (214 nm) | | | |
|---|---|---|---|---|---|---|
| Compound ID | R Group | Monoisotopic FW | Retention Time (min) | Peak Area (%) | Target Found | (MH)+ Observed |
| M41697-1Z | r1m01-r2m01 | 552 | 9.69 | $^A$92.0 | ✓ | 553.2 |
| M41697-2Z | r1m04-r2m04 | 644 | 9.90 | 83.5 | ✓ | 645.3 |
| M41697-4Z | r1m07-r2m07 | 436 | 7.53 | 91.9 | ✓ | 437.1 |
| M41697-5Z | r1m08-r2m08 | 508 | 8.94 | 83.7 | ✓ | $^B$509.3 |
| M41697-6Z | r1m09-r2m09 | 400 | 7.62 | 89.6 | ✓ | 401.2 |
| M41697-7Z | r1m10-r2m10 | 472 | 8.73 | 86.2 | ✓ | 473.1 |
| M41697-8Z | r1m11-r2m11 | 400 | 7.41 | 73.1 | ✓ | 401.3 |
| M41697-9Z | r1m12-r2m12 | 508 | 8.59 | 83.8 | ✓ | 509.3 |
| M41697-10Z | r1m13-r2m13 | 428 | 8.04 | 90.3 | ✓ | 429.2 |
| M41697-11Z | r1m14-r2m14 | 432 | 6.68 | 86.8 | ✓ | 433.3 |
| M41697-12Z | r1m16-r2m16 | 408 | 6.75 | 83.6 | ✓ | 409.0 |
| M41697-13Z | r1m17-r2m17 | 400 | 7.82 | 89.8 | ✓ | 401.4 |
| M41697-14Z | r1m18-r2m18 | 432 | 7.52 | 89.0 | ✓ | 433.1 |
| M41697-15Z | r1m20-r2m20 | 372 | 6.67 | 89.6 | ✓ | 373.1 |
| M41697-16Z | r1m22-r2m22 | 460 | 6.50 | $^A$86.2 | ✓ | 461.1 |
| M41697-17Z | r1m24-r2m24 | 360 | 9.00 | 89.2 | ✓ | 361.2 |
| M41697-18Z | r1m25-r2m25 | 304 | 5.95 | 90.8 | ✓ | 305.2 |
| M41697-19Z | r1m26-r2m26 | 360 | 5.16 | 85.4 | ✓ | 361.1 |
| M41697-20Z | r1m27-r2m27 | 272 | 4.14 | 72.8 | ✓ | 273.1 |
| M41697-31Z | r1m40-r2m40 | 468 | 8.56 | 86.1 | ✓ | $^B$469.1 |
| M41697-34Z | r1m44-r2m44 | 444 | 6.92 | 78.1 | ✓ | 445.0 |

$^A$Analysis of unpooled second cleavage product; compounds M41697-1X and M41697-16X respectively.
$^B$Correct isotope pattern observed.

EXAMPLE 6

Synthesis of a Second Library of Tertiary Guanidine Acid Compounds (Library M0008)

Library M0008 is a single compound library of 21 tertiary guanidine amides. The scaffold for this library is shown in formula VI Formula VI

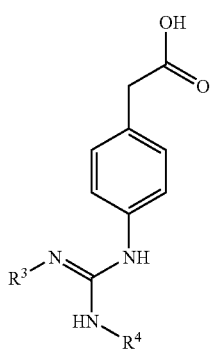

Scaffold for Library M0008 in which $R^3$ is the same as $R^4$, and is derived from a primary amine. Thus these compounds represent a subset of formula I in which A is methylene, $R^1$ is hydroxyl, $R^2$ is hydrogen, G is absent, $R^3$ and $R^4$ are derived from a primary amine.

The library was synthesised using 21 primary amines for the $R^3$ and $R^4$ substituents. This library was derived from library M0007 by splitting the amide products derived from that library, then hydrolysing one set to the corresponding acids. The purity (as estimated by RP-HPLC at 214 nm) of compounds in Library M0008 averages 85.0%, and ranges from 68% to 92% (s.d.=6.2%), determined from analysis of all 21 compounds in the library.

The compounds were plated on the basis of 4.8 mg relative to the average mass obtained for the complete set of 21 compounds. The amount of compound per well was 11 μmol, based on an average molecular weight of 432 amu.

Synthesis

The synthesis is summarized in Reaction Scheme 6. Fmoc-protected 4-aminophenylacetic acid was coupled on to PS Rink Lanterns (loading: 36 μmol) using DIC and HOBt. The Fmoc protecting group was then removed with piperidine/DMF. The resultant aniline was then treated with Fmoc-NCS, then Fmoc deprotected. The thiourea functionalised Lanterns formed were then S-methylated with iodomethane. Subsequent reaction with 21 different primary amines followed by cleavage from the solid phase using 20% TFA/DCM afforded the 21 tertiary guanidines comprising Library M0008.

Reaction Scheme 6

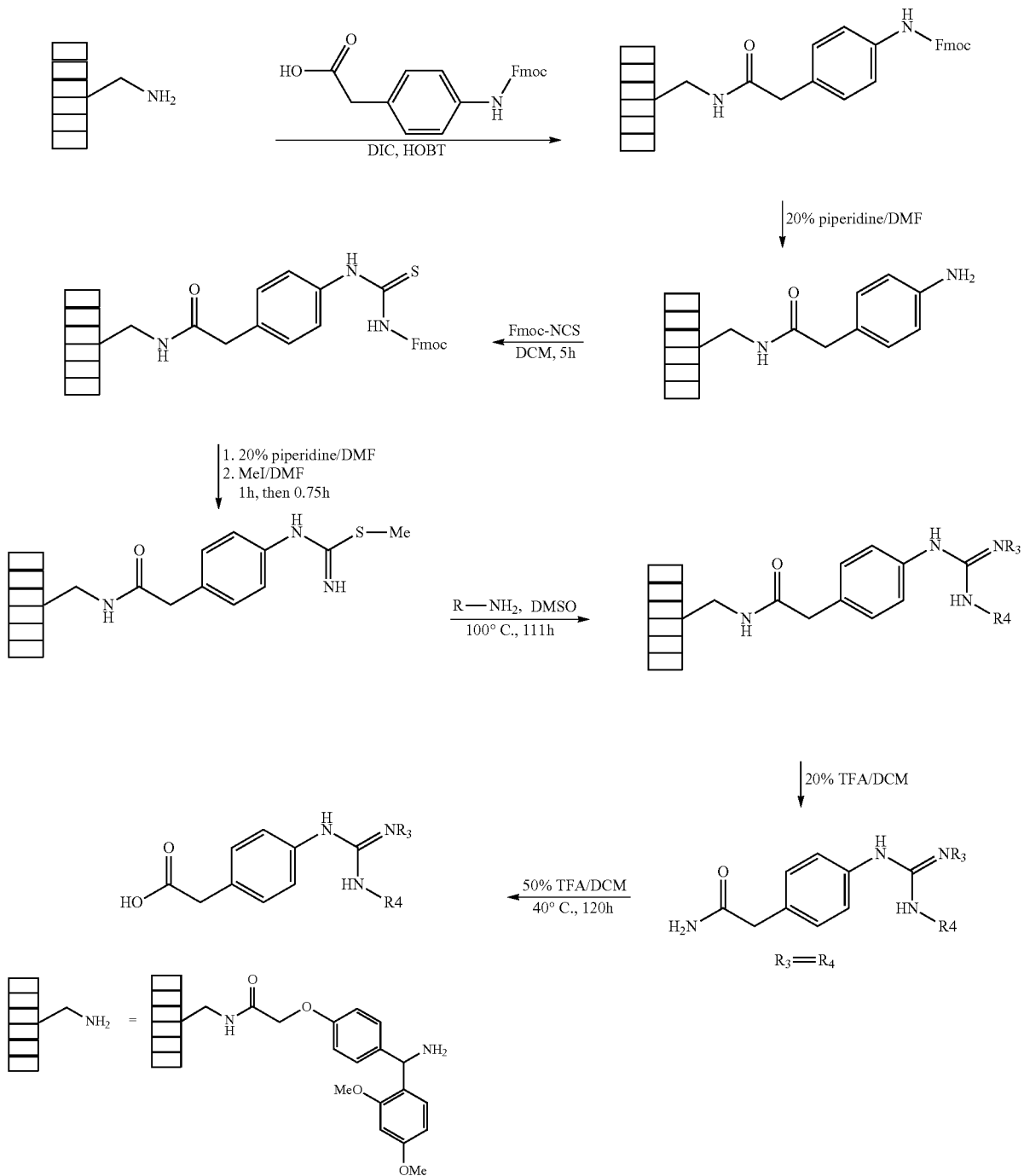

Reaction Scheme for Library M0008
R—NH₂ represents the primary amine coresponding to R₃, R₄.

(i) Preparation of the Fmoc-Protected 4-Aminophenylacetic Acid

A solution of 4-aminophenylacetic acid (5.0 g, 33.1 mmol) in warm DMF (35 mL) was prepared under $N_2$. The solution was then heated to 75° C., and FmocCl (4.24 g, 16.4 mmol) was added in 4 portions over 5 minutes. The resultant mixture was then stirred at 75° C. for 45 minutes. The solution was cooled to room temperature, then a solution of 1M HCl (100 mL) was added. The precipitate which formed was collected via vacuum filtration and washed with 3 portions of deionised water (2×50 mL, 1×100 mL). The solid collected was then vacuum dried overnight at 30° C., then for 2 h at 50° C. to yield Fmoc-4-aminophenylacetic acid (5.39 g; 44%) as a beige solid.

(ii) Coupling of the Fmoc-Protected 4-Aminophenylacetic Acid to Fmoc-Protected Rink PS Lanterns 50 PS Rink D-series Lanterns (batch 1531, loading: 36 µmol) were Fmoc deprotected by double treatment with 20% piperidine/DMF for 40 min and 30 min respectively. The second piperidine solution was removed and the Lanterns washed with DMF (3×10 min), 50% DMF/DCM (3×10 min) and DCM (3×10 min).

A solution of Fmoc-4-aminophenylacetic acid (0.098M), HOBt.$H_2O$ (0.12M) and DIC (0.2M) in 20% DMF/DCM was prepared. To this solution was added the Fmoc-deprotected Lanterns. The mixture was then gently agitated at room temperature for 21 h. At the completion of the reaction, the coupling solution was removed and the Lanterns washed with DMF (3×10 min), 50% DMF/DCM (3×10 min) and DCM (3×10 min). The Lanterns were air-dried overnight.

The Fmoc group was then removed by treating the Lanterns with a solution of 20% piperidine/DMF at room temperature for 5 hours. Two Lanterns were subjected to a loading determination, result: 33.9 µmol (average). The piperidine solution was removed and the Lanterns were washed with DMF (3×10 min), 50% DMF/DCM (3×10 min) and DCM (3×10 min).

(iii) Reaction with Fmoc-NCS and Iodomethane

A solution of Fmoc-NCS (0.2M) in DCM was prepared. The Lanterns from step (ii) were added to this solution and allowed to stand at room temperature for 5 h. The reaction solution was then drained and the Lanterns were washed with DCM (3×10 min), DMF (3×10 min) and DCM (3×10 min). The Lanterns were vacuum dried overnight at 40° C.

The Lanterns were again Fmoc-deprotected, with 20% piperidine/DMF for 2.5 h. The piperidine solution was drained and the Lanterns washed with DMF (3×10 min) and DCM (3×10 min). The Lanterns were vacuum dried overnight at 45° C.

A solution of iodomethane (0.2M) in DMF (distilled) was prepared. The Fmoc-deprotected Lanterns were added and then the contents were gently agitated at room temperature for 1 hour. A second solution of iodomethane (0.2M) in DMF was prepared. The first iodomethane solution was drained and the second iodomethane solution added immediately to the Lanterns. The Lanterns were then gently agitated at room temperature for a further 45 min. The iodomethane solution was drained and the Lanterns washed with DMF (3×10 min) and DCM (3×10 min). The Lanterns were then vacuum dried overnight at 35° C.

(iv) Tertiary Guanidine Formation

Solutions (4M) of the primary amines in DMSO (AR Grade) were prepared (1.25 mL). The primary amines used are summarized in Table 14. One Lantern from step (iii) was then added to each amine solution. The reaction solutions were heated to 100° C. for 111 h. At the completion of the reactions, the amine solutions were removed and the Lanterns washed with DMSO (2×10 min), DMF (3×10 min), 50% DMF/DCM (3×10 min) and DCM (3×10 min). The Lanterns were air-dried overnight at room temperature.

(v) Cleavage from the Solid Phase

Cleavage Stems were manually attached to each Lantern and each Stem/Lantern assembly mounted onto a backing plate for cleavage. The Lanterns were then cleaved using 0.75 mL per Lantern of 10% TFA (distilled)/DCM for 1 h using a 96 well Bio-Rad® tray format. The resulting cleavage solutions were evaporated in vacuo using a centrifugal evaporator (GeneVac). The samples were then dissolved in 90% MeCN/$H_2O$ (0.9 mL) for analysis.

Since the Lanterns had been inadvertently cleaved with 10% TFA/DCM instead of 20% TFA/DCM, the Lanterns were then re-cleaved using 0.75 mL of 20% TFA/DCM for 1 hour. The resulting cleavage solutions were evaporated in vacuo using a centrifugal evaporator. The dried samples were then dissolved in 90% MeCN/$H_2O$ for analysis. After it was determined that the sets of compounds cleaved from the Lanterns in the two cleavages were essentially identical, the stocks were combined into a single plate. The solutions were then evaporated in vacuo. The samples were then re-dissolved in 90% MeCN/$H_2O$ and re-analysed, then concentrated.

(vi) Amide Hydrolysis

The amide products above were dissolved in 90% MeCN/$H_2O$ an half of each solution was dispensed into new Bio-Rad® tubes and evaporated in vacuo. A solution of TFA/$H_2O$ 1:1 (900 µL) was dispensed into each well, the tubes were capped, a heavy metal plate was placed on top of the capped tubes to keep the caps in place, and the tubes were heated to 40° C. for 120 h. The samples were then concentrated, redissolved in 90% MeCN/$H_2O$ and analysed, then concentrated and redissolved in 90% MeCN/$H_2O$, then dispensed into a microtitre plate.

Analysis

All 21 compounds were analysed by reverse phase HPLC and electrospray mass spectrometry as described in Example 1. All compounds displayed the target molecular weight. A minor peak (ca. 3-5%), due to the presence of the corresponding starting amide was observed in most cases, indicating incomplete hydrolysis. The results are summarized in Table 15.

TABLE 14

Summary of $R^3$ and $R^4$ group structures and details for library M0008

| Fragment Tag | $R^3$ and $R^4$ Group Structure | Reagent Name | Reagent Tag |
|---|---|---|---|
| R1m01 | 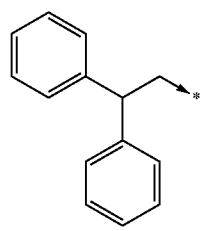 | 2,2-diphenylethylamine | DAC005 |

TABLE 14-continued

Summary of $R^3$ and $R^4$ group structures and details for library M0008

| Fragment Tag | $R^3$ and $R^4$ Group Structure | Reagent Name | Reagent Tag |
|---|---|---|---|
| R1m04 | 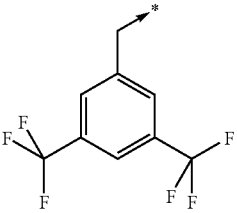 | 3,5-bis(trifluoromethyl)benzylamine | DAD008 |
| R1m07 | 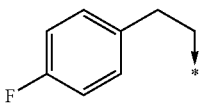 | 4-fluorophenethylamine | DAD023 |
| R1m08 | 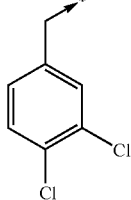 | 3,4-dichlorobenzylamine | DAD024 |
| R1m09 | 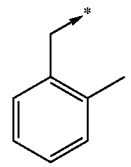 | 2-methylbenzylamine | DAC009 |
| R1m10 | 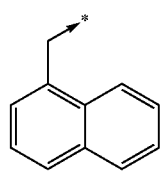 | 1-naphthalenemethylamine | DAC004 |
| R1m11 | 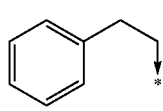 | 2-phenethylamine | DAC006 |
| R1m12 | 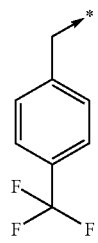 | 4-(trifluoromethyl)benzylamine | DAD006 |
| R1m13 | 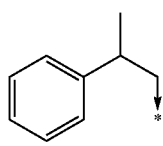 | 1-amino-2-phenylpropane (beta-phenethylamine) | DAC008 |

TABLE 14-continued

Summary of R³ and R⁴ group structures and details for library M0008

| Fragment Tag | R³ and R⁴ Group Structure | Reagent Name | Reagent Tag |
|---|---|---|---|
| R1m14 | 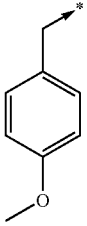 | 4-methoxybenzylamine | DAD003 |
| R1m16 | 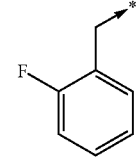 | 2-fluorobenzylamine | DAD004 |
| R1m17 | 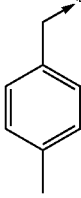 | 4-methylbenzylamine | DAC007 |
| R1m18 | 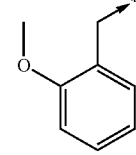 | 2-methoxybenzylamine | DAD009 |
| R1m20 | 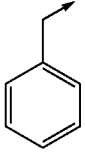 | benzylamine | DAC003 |
| R1m22 | 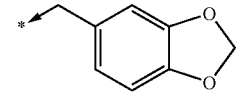 | piperonylamine | DAD002 |
| R1m24 | 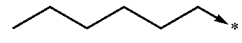 | hexylamine | DAA002 |
| R1m25 | 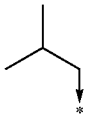 | isobutylamine | DAA010 |
| R1m26 | 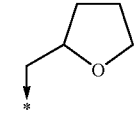 | (+/−)-tetrahydrofurfurylamine | DAB010 |
| R1m27 |  | allylamine | DAA005 |

TABLE 14-continued

Summary of R³ and R⁴ group structures and details for library M0008

| Fragment Tag | R³ and R⁴ Group Structure | Reagent Name | Reagent Tag |
|---|---|---|---|
| R1m40 | 4-chlorophenyl-CH₂CH₂- | 2-(4-chlorophenyl)ethylamine | DAD008 |
| R1m44 | 2,5-difluorobenzyl- | 2,5-difluorobenzylamine | DAD027 |

TABLE 15

Summary of Analytical Results: Library M0008

| | Compound Identification | | HPLC and LC-MS Data (214 nm) | | | |
|---|---|---|---|---|---|---|
| Compound ID | R Group | Monoisotopic FW | Retention Time (min) | Peak Area (%) | Target Found | (MH)+ Observed |
| M4170016-1  | r1m01-r2m01 | 553 | 10.41 | 91.1 | ✓ | 554.4 |
| M4170016-2  | r1m04-r2m04 | 645 | 10.43 | 85.5 | ✓ | 646.4 |
| M4170016-4  | r1m07-r2m07 | 437 | 8.12  | 91.3 | ✓ | 438.1 |
| M4170016-5  | r1m08-r2m08 | 509 | 9.48  | 85.0 | ✓ | ᴬ510.0 |
| M4170016-6  | r1m09-r2m09 | 401 | 8.24  | 89.6 | ✓ | 402.4 |
| M4170016-7  | r1m10-r2m10 | 473 | 9.28  | 88.1 | ✓ | 474.3 |
| M4170016-8  | r1m11-r2m11 | 401 | 8.00  | 67.6 | ✓ | 402.5 |
| M4170016-9  | r1m12-r2m12 | 509 | 9.11  | 85.6 | ✓ | 510.1 |
| M4170016-10 | r1m13-r2m13 | 429 | 8.67  | 86.8 | ✓ | 430.4 |
| M4170016-11 | r1m14-r2m14 | 433 | 7.34  | 73.6 | ✓ | 434.4 |
| M4170016-12 | r1m16-r2m16 | 409 | 7.37  | 82.7 | ✓ | 410.2 |
| M4170016-13 | r1m17-r2m17 | 401 | 8.40  | 87.8 | ✓ | 402.3 |
| M4170016-14 | r1m18-r2m18 | 433 | 8.12  | 87.0 | ✓ | 434.3 |
| M4170016-15 | r1m20-r2m20 | 373 | 7.30  | 86.4 | ✓ | 374.4 |
| M4170016-16 | r1m22-r2m22 | 461 | 7.02  | 82.6 | ✓ | 462.1 |
| M4170016-17 | r1m24-r2m24 | 361 | 9.60  | 92.3 | ✓ | 362.2 |
| M4170016-18 | r1m25-r2m25 | 305 | 6.62  | 88.4 | ✓ | 306.0 |
| M4170016-19 | r1m26-r2m26 | 361 | 5.74  | 90.8 | ✓ | 362.3 |
| M4170016-20 | r1m27-r2m27 | 273 | 4.74  | 76.1 | ✓ | 274.1 |
| M4170016-31 | r1m40-r2m40 | 469 | 9.05  | 86.4 | ✓ | ᴬ470.1 |
| M4170016-34 | r1m44-r2m44 | 445 | 7.52  | 80.7 | ✓ | 446.0 |

ᴬCorrect isotope pattern observed.

EXAMPLE 7

Synthesis of Tertiary Guanidine Amide Compound: 4-[N'-Cyclohexylmethyl-N"-(2-methyl-benzyl)-guanidino]-3-(phenoxym-ethoxy)-benzamide The synthesis is summarised in Reaction Scheme 7.

Reaction Scheme 7

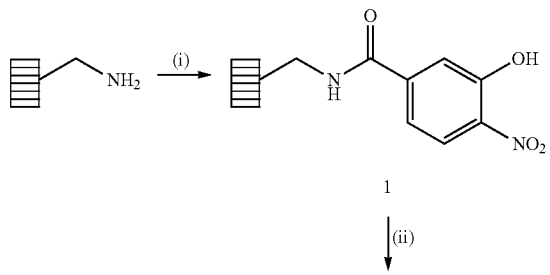

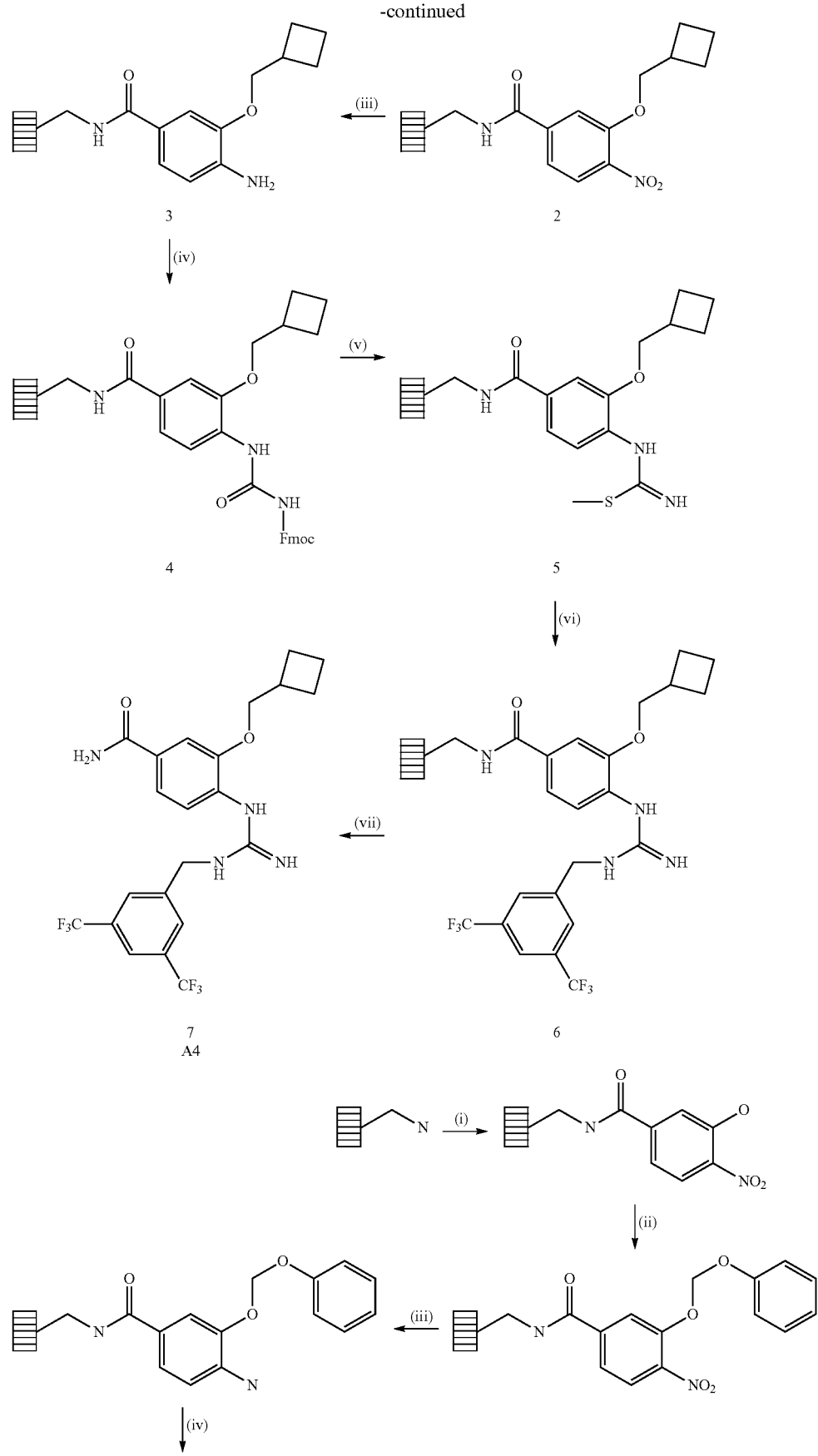

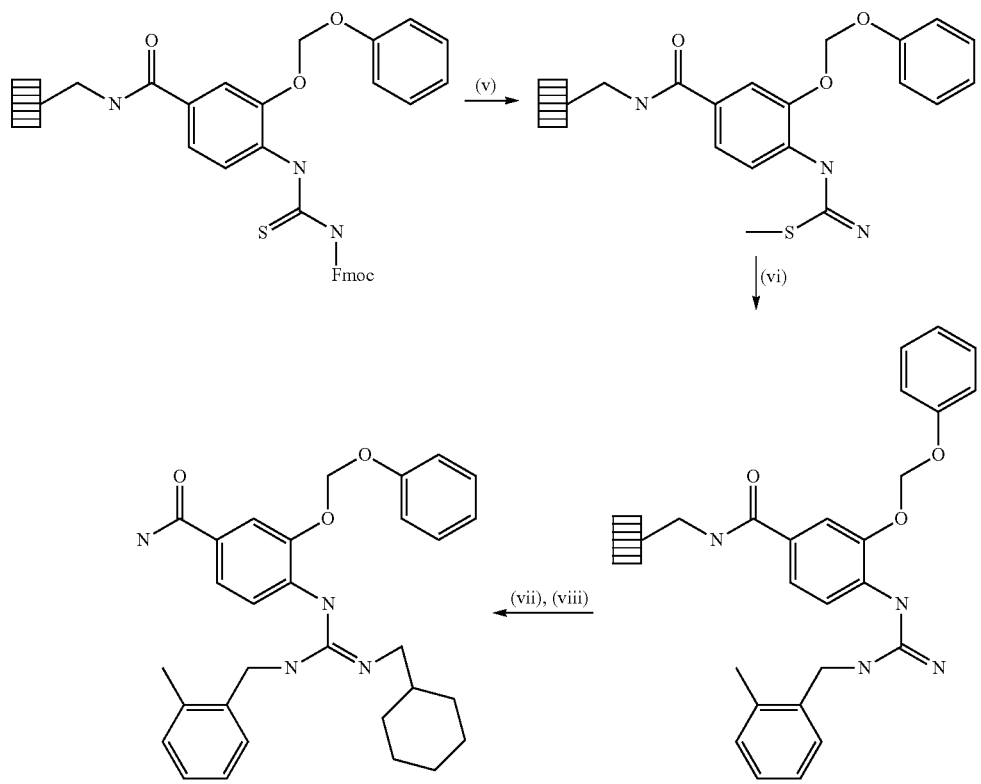
4-[N′-Cyclohexylmethyl-N″-(2-methyl-benzyl)-guanidino]-3-phenoxymethoxy-benzamide
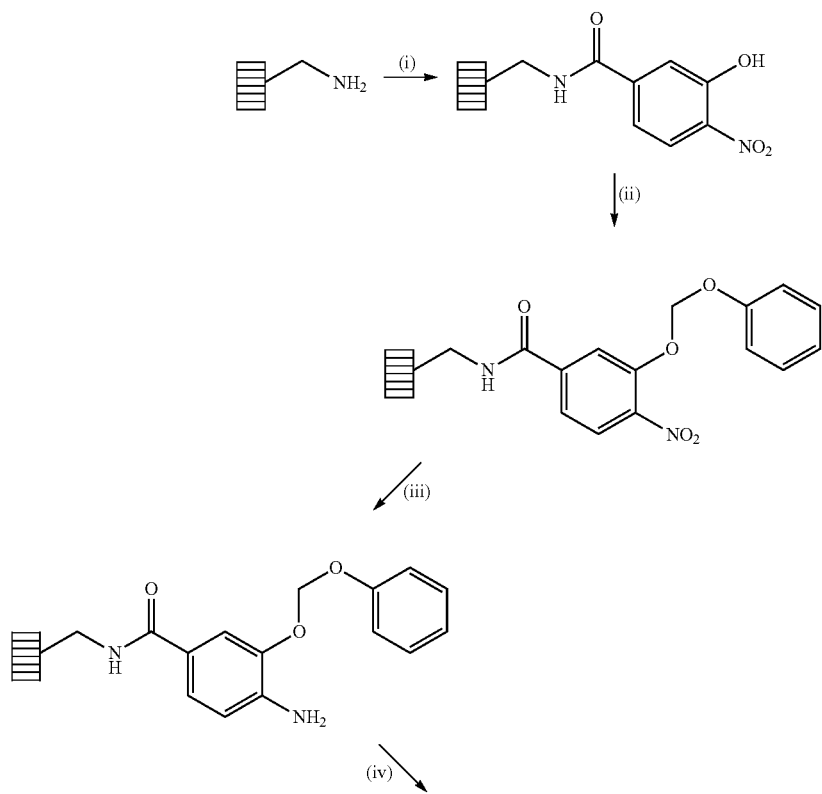

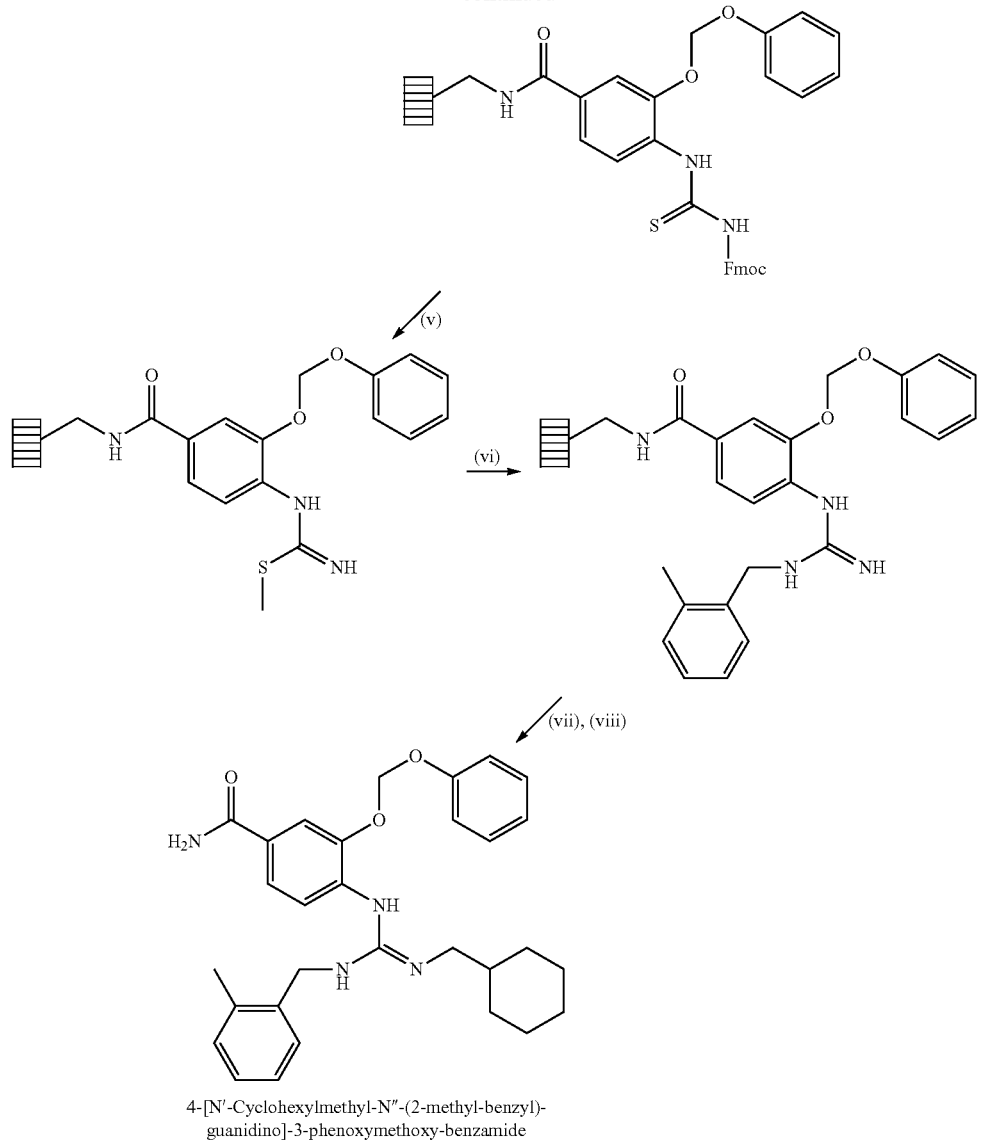

4-[N'-Cyclohexylmethyl-N''-(2-methyl-benzyl)-guanidino]-3-phenoxymethoxy-benzamide In Reaction Scheme 7: (i) DIC, DMAP, CH$_2$Cl$_2$, room temperature, 16 h; (ii) KH, DMF, 100° C., 24 h; (iii) SnCl$_2$.2H$_2$O, DMF, room temperature, 24 h; (iv) FmocNCS, CH$_2$Cl$_2$, room temperature, 7 h; (v) 20% piperidine/DMF, room temperature, 40 min, 1 h 20 min, then CH$_3$I, DMF, 40 min×2; (vi) 2-methylbenzylamine, DMSO, 75-85° C., 9 h; (vii) cyclohexylmethylamine, DMSO, 100° C., 4 days; (viii) 20% TFA/CH$_2$Cl$_2$, room temperature, 1 h.

Synthetic Step (i)

100 PS-D-RAM SynPhase™ Lanterns (batch 1703-13A, loading capacity 35 µmol) with Rink amide linker attached were Fmoc-deprotected using a solution of premixed 20% piperidine/DMF (v/v) (2×40 min). The piperidine solution was filtered off and the Lanterns washed with DMF (5×20 min) and CH$_2$Cl$_2$ (2×10 min).

80 mL of a solution of 3-hydroxy-4-nitrobenzoic acid (0.2M), DIC (0.1M) and DMAP (0.05M) in CH$_2$Cl$_2$ was prepared. The solution was allowed to stand at room temperature for 3 min then was added to the Fmoc-deprotected Lanterns. The Lanterns were stood at room temperature for 16 h. The reaction solution was then drained and the Lanterns washed with CH$_2$Cl$_2$ (4×20 min), DMF (8×20 min). Concomitantly-formed esters were then cleaved using alternate solutions of 10% ethanolamine/DMF (v/v) (15 min) and DMF (10 min) until clear spent washing solutions were obtained—approximately 6 cycles. The Lanterns were then washed with 50% CH$_3$COOH/CH$_2$Cl$_2$ (v/v) (2×10 min) then CH$_2$Cl$_2$ (3×10 min) and vacuum dried at 40° C. for 1 hour.

Synthetic Step (ii)

The Lanterns from step (i), 56 in total were subjected to treatments with a slurry of excess potassium hydride (freshly extracted with petroleum ether from mineral oil) in anhydrous DMF for 30 min and 5 min respectively.

40 mL of a solution of 2-phenoxyethyl bromide (1.0M) and Cs$_2$CO$_3$ (0.3M) in anhydrous DMF was prepared. The KH-treated Lanterns were then added to this reaction solution and left to stand at 100° C. for 24 h. The reaction solution was drained and the Lanterns transferred to a clean vessel. The Lanterns were washed with DMF (3×10 min), 50% DMF/H$_2$O (v/v) (2×30 min), DMF (2×10 min) and CH$_2$Cl$_2$ (4×10 min) then vacuum dried at 40° C. for 1 hour.

Synthetic Step (iii)

34 mL of a solution of tin(II)chloride dihydrate (1M) in DMF (distilled grade) was prepared. This solution was then added to the Lanterns from step (ii) and stood at room temperature for 24 h. The reaction solution was drained and the Lanterns washed with DMF (2×5 min), 20% H$_2$O/THF (2×30 min, 1×15 min), THF (1×15 min) and CH$_2$Cl$_2$ (4×15 min) then air dried overnight.

Synthetic Step (iv)

34 mL of a solution of FmocNCS (0.2M) in CH$_2$Cl$_2$ was prepared. The reaction solution was added to 50 Lanterns from step (iii) and the Lanterns stood at room temperature for 6.5 h, then heated to 40° C. for the final 0.5 h (total of 7 h reaction time). At the conclusion of the reaction, the Fmoc-NCS solution was drained and the Lanterns washed with CH$_2$Cl$_2$ (4×10 min), DMF (2×10 min). These Lanterns were taken immediately to step (v).

Synthetic Step (v)

The Lanterns were firstly treated with 20% piperidine/DMF (v/v) at room temperature (2 treatments of 40 min and 1 h 20 min respectively; there were no washes in between treatments). The second piperidine solution was drained and the Lanterns washed with DMF (4×10 min). The lanterns were further reacted immediately.

A solution of iodomethane (0.2M) in DMF was prepared and added to the Fmoc-deprotected Lanterns. The Lanterns were allowed to stand at room temperature for 40 min. The iodomethane solution was then removed and the Lanterns subjected to a second solution of iodomethane (0.2M) in DMF for 40 min; there were no washes in between treatments. After the 40 min was complete, the reaction solution was drained and the Lanterns washed with DMF (5×10 min) and DMSO (1×10 min). The Lanterns were taken immediately to step (vi).

Synthetic Step (vi)

Four Lanterns from step (v) were added to a solution of 2-methylbenzylamine (2.0M) in DMSO then placed in an oven set to 85° C. for 6 h. At the completion of the reaction, the amine solution was drained and the Lanterns washed with hot (85° C.) DMSO (2×10 min, 2×30 min), DMF (3×10 min) and CH$_2$Cl$_2$ (3×20 min). The Lanterns were then air dried overnight.

Synthetic Step (vii)

Two Lanterns were then added to a solution of cyclohexylmethylamine (1.0M) in DMSO then placed in an oven set to 100° C. for 4 days. At the completion of the reaction, the amine solution was drained and the Lanterns washed with hot (85° C.) DMSO (2×10 min, 2×30 min), DMF (3×10 min) and CH$_2$Cl$_2$ (3×20 min). The Lanterns were then air dried overnight.

Synthetic Step (viii)

The Lanterns were cleaved using a solution of 20% TFA/CH$_2$Cl$_2$ (v/v). The Lanterns were stood at room temperature for 1 h. The solution was evaporated under reduced pressure to give an oil. The oil was dissolved in 90% MeCN/H$_2$O. The required tertiary guanidine was identified by analytical LCMS (purity=14%).

EXAMPLE 8

Synthesis of Tertiary Guanidine Amide Compound: 3-Benzyloxy-4-[N'-cyclohexylmethyl-N"-(2-methyl-benzyl)-quanidino]-benzamide The synthesis is summarised in Reaction Scheme 8.

Reaction Scheme 8

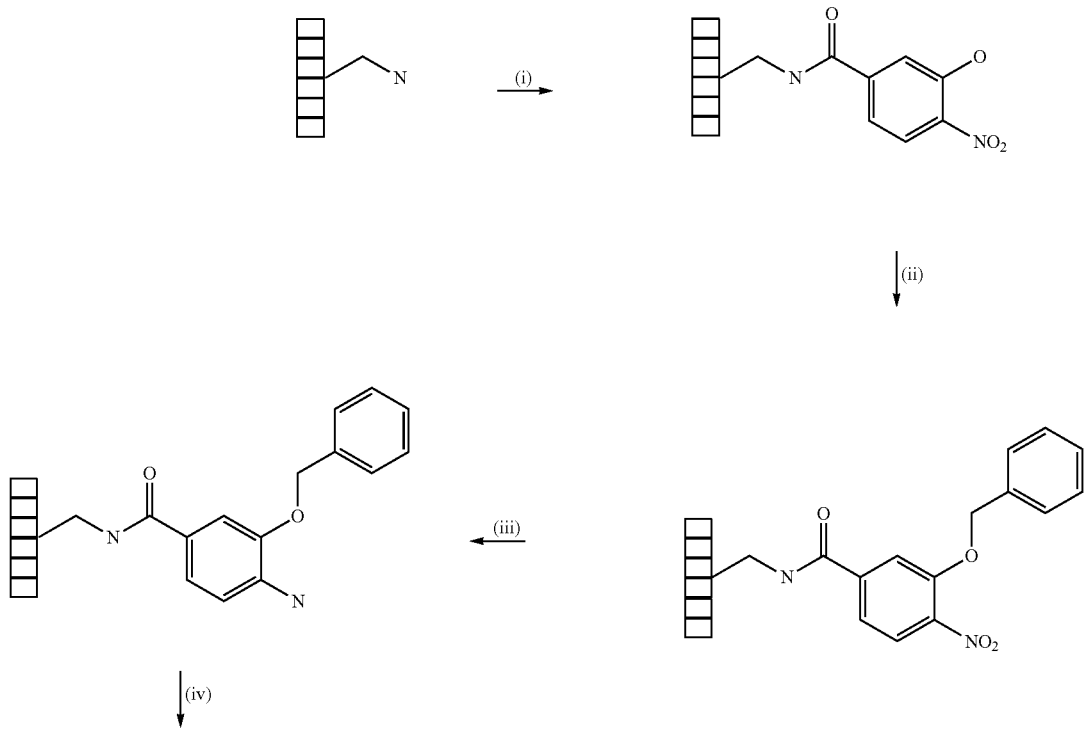

105
-continued
106
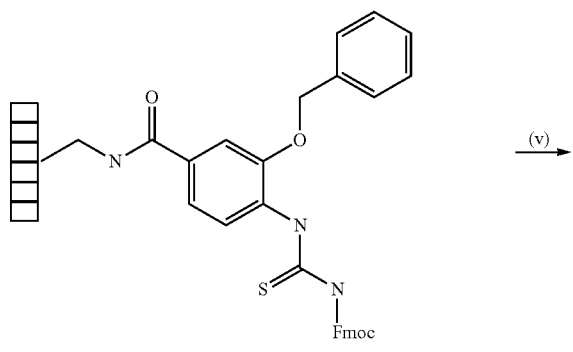
(v)
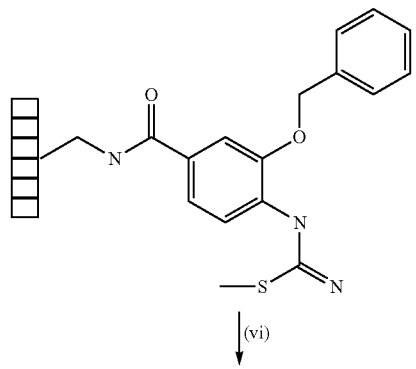
(vi)
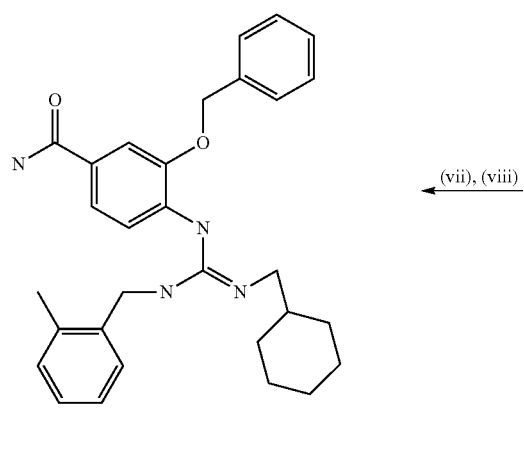
←── (vii), (viii) ──
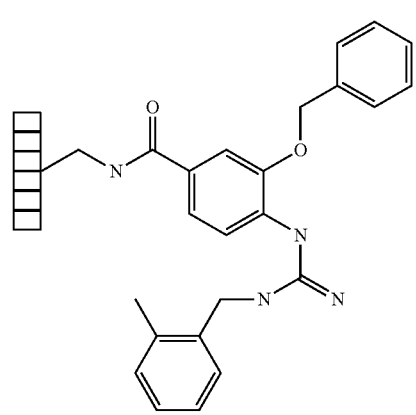
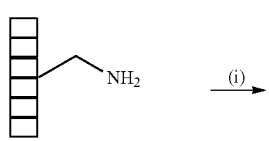
(i) →
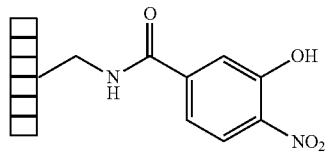
(ii)
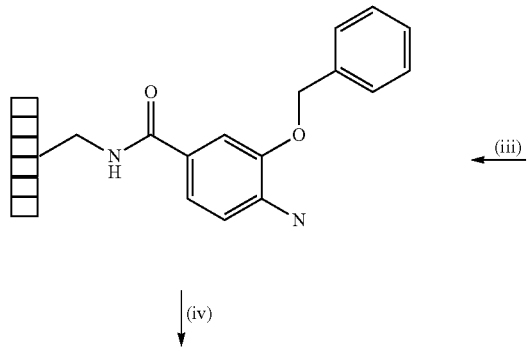
←── (iii) ──
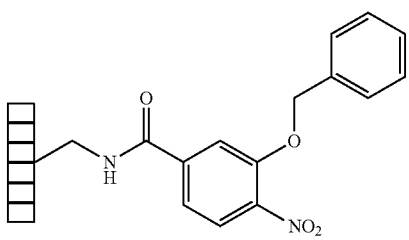
(iv)

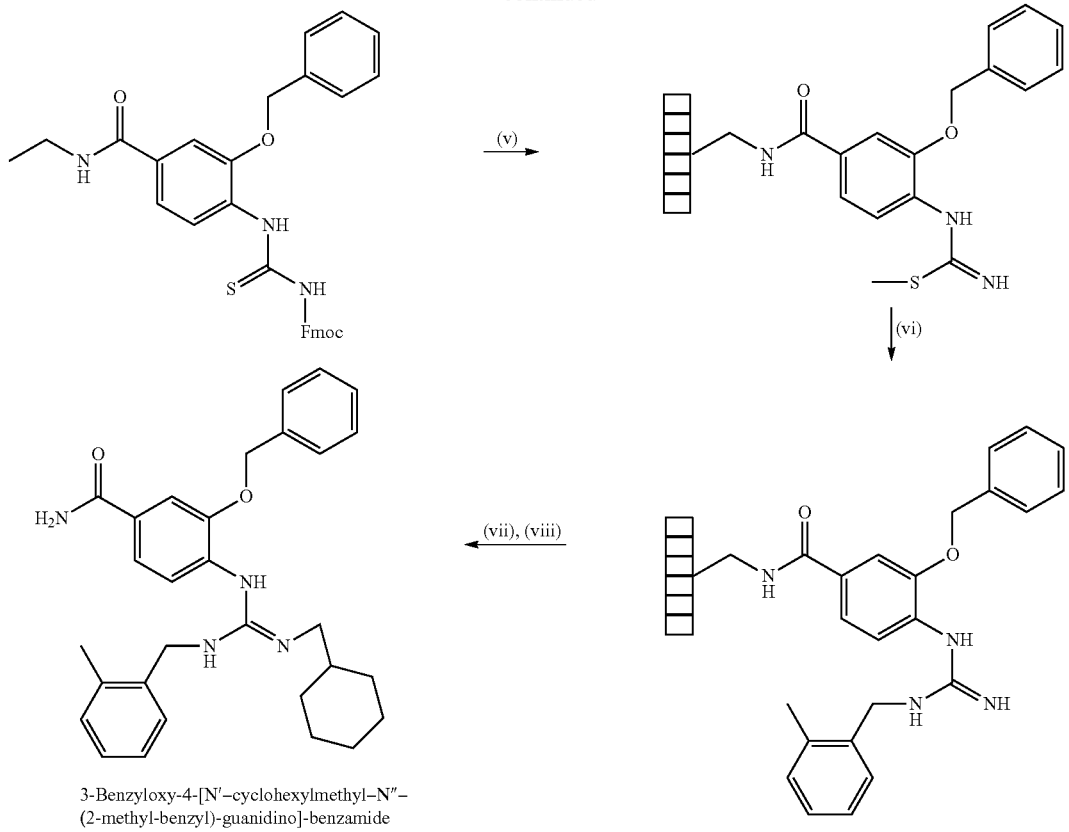

3-Benzyloxy-4-[N'-cyclohexylmethyl-N"-(2-methyl-benzyl)-guanidino]-benzamide

In Reaction Scheme 8: (i) DIC, DMAP, $CH_2Cl_2$, room temperature, 16 h; (ii) benzylbromide, KH, DMF, 40° C., 24 h; (iii) $SnCl_2.2H_2O$, DMF, room temperature, 24 h; (iv) FmocNCS, $CH_2Cl_2$, room temperature, 7 h; (v) 20% piperidine/DMF, room temperature, 40 min, 1 h 20 min, then $CH_3I$, DMF, 40 min×2; (vi) 2-methylbenzylamine, DMSO, 75-85° C., 9 h; (vii) cyclohexylmethylamine, DMSO, 100° C., 4 days; (viii) 20% TFA/CH2Cl2, room temperature, 1 h.

Synthetic Step (i)

100 PS-D-RAM SynPhase™ Lanterns (batch 1703-13A, loading capacity 35 µmol) with Rink amide linker attached were Fmoc-deprotected using a solution of premixed 20% piperidine/DMF (v/v) (2×40 min). The piperidine solution was filtered off and the Lanterns washed with DMF (5×20 min) and $CH_2Cl_2$ (2×10 min).

80 mL of a solution of 3-hydroxy-4-nitrobenzoic acid (0.2M), DIC (0.1M) and DMAP (0.05M) in $CH_2Cl_2$ was prepared. The solution was allowed to stand at room temperature for 3 min then was added to the Fmoc-deprotected Lanterns. The Lanterns were stood at room temperature for 16 h. The reaction solution was then drained and the Lanterns washed with $CH_2Cl_2$ (4×20 min), DMF (8×20 min). Concomitantly-formed esters were then cleaved using alternate solutions of 10% ethanolamine/DMF (v/v) (15 min) and DMF (10 min) until clear spent washing solutions were obtained—approximately 6 cycles. The Lanterns were then washed with 50% $CH_3COOH/CH_2Cl_2$ (v/v) (2×10 min) then $CH_2Cl_2$ (3×10 min) and vacuum dried at 40° C. for 1 hour.

Synthetic Step (ii)

The Lanterns from step (i), 56 in total were subjected to treatments with a slurry of excess potassium hydride (freshly extracted with petroleum ether from mineral oil) in anhydrous DMF for 30 min and 5 min respectively.

40 mL of a solution of benzyl bromide (1.0M) and $Cs_2CO_3$ (0.3M) in anhydrous DMF was prepared. The KH-treated Lanterns were then added to this reaction solution and left to stand at 40° C. for 24 h. The reaction solution was drained and the Lanterns transferred to a clean vessel. The Lanterns were washed with DMF (3×10 min), 50% DMF/$H_2O$ (v/v) (2×30 min), DMF (2×10 min) and $CH_2Cl_2$ (4×10 min) then vacuum dried at 40° C. for 1 hour.

Synthetic Step (iii)

34 mL of a solution of tin(II)chloride dihydrate (1M) in DMF (distilled grade) was prepared. This solution was then added to the Lanterns from step (ii) and stood at room temperature for 24 h. The reaction solution was drained and the Lanterns washed with DMF (2×5 min), 20% $H_2O$/THF (2×30 min, 1×15 min), THF (1×15 min) and $CH_2Cl_2$ (4×15 min) then air dried overnight.

Synthetic Step (iv)

34 mL of a solution of FmocNCS (0.2M) in $CH_2Cl_2$ was prepared. The reaction solution was added to 50 Lanterns from step (iii) and the Lanterns stood at room temperature for 6.5 h, then heated to 40° C. for the final 0.5 h (total of 7 h reaction time). At the conclusion of the reaction, the Fmoc-NCS solution was drained and the Lanterns washed with $CH_2Cl_2$ (4×10 min), DMF (2×10 min). These Lanterns were taken immediately to step (v).

Synthetic Step (v)

The Lanterns were firstly treated with 20% piperidine/DMF (v/v) at room temperature (2 treatments of 40 min and 1 h 20 min respectively; there were no washes in between treatments). The second piperidine solution was drained and the Lanterns washed with DMF (4×10 min). The lanterns were further reacted immediately.

A solution of iodomethane (0.2M) in DMF was prepared and added to the Fmoc-deprotected Lanterns. The Lanterns were allowed to stand at room temperature for 40 min. The iodomethane solution was then removed and the Lanterns subjected to a second solution of iodomethane (0.2M) in DMF for 40 min; there were no washes in between treatments. After the 40 min was complete, the reaction solution was drained and the Lanterns washed with DMF (5×10 min) and DMSO (1×10 min). The Lanterns were taken immediately to step (vi).

Synthetic Step (vi)

Four Lanterns from step (v) were added to a solution of 2-methylbenzylamine (2.0M) in DMSO then placed in an oven set to 85° C. for 6 h. At the completion of the reaction, the amine solution was drained and the Lanterns washed with hot (85° C.) DMSO (2×10 min, 2×30 min), DMF (3×10 min) and CH$_2$Cl$_2$ (3×20 min). The Lanterns were then air dried overnight.

Synthetic Step (vii)

Two Lanterns were then added to a solution of cyclohexylmethylamine (1.0M) in DMSO then placed in an oven set to 100° C. for 4 days. At the completion of the reaction, the amine solution was drained and the Lanterns washed with hot (85° C.) DMSO (2×10 min, 2×30 min), DMF (3×10 min) and CH$_2$Cl$_2$ (3×20 min). The Lanterns were then air dried overnight.

Synthetic Step (viii)

The Lanterns were cleaved using a solution of 20% TFA/CH$_2$Cl$_2$ (v/v). The Lanterns were stood at room temperature for 1 h. The solution was evaporated under reduced pressure to give an oil. The oil was dissolved in 90% MeCN/H$_2$O. The required tertiary guanidine was identified by analytical LCMS (purity=32%).

EXAMPLE 9

Effect of Arginine Analogues on Arginine Transport Across the Cell Membrane

A consolidated chemical library of all the compounds synthesised in Examples 1 to 6 was evaluated for their effect on NOS activity and L-arginine transport at high concentration. A total of 280 compounds was assayed.

The activity of the inducible isoform of NOS was tested by evaluating the ability of the compounds to interfere with NO production in J774 cells which had been exposed to an inflammatory cytokine cocktail. In brief, J774 cells were exposed to an inflammatory cytokine cocktail containing bacterial lipopolysaccharide (1 µg/ml) and interferon gamma (10 U/ml) for 24 hours, in the presence or absence of the test compound at 100 µM. The concentration of nitrite in the culture media was determined as an index of the amount of nitric oxide generated during the incubation period (Simmons et al, 1996.) A large number of inhibitory compounds was identified in this assay.

In parallel with this assay, the capacity for these compounds to alter arginine entry into cells was assessed. Initial studies were conducted in HeLa cells. Arginine entry was determined by the rate of entry of radiolabelled L-arginine into the cells, using the method of Kaye et al., (2000). Of the total library, four compounds were identified which had inhibitory activity at a Ki of 100 µM. These compounds were as follows:

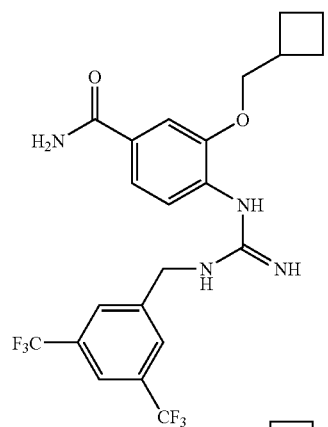

A4

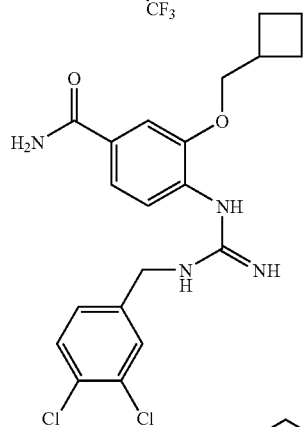

A7

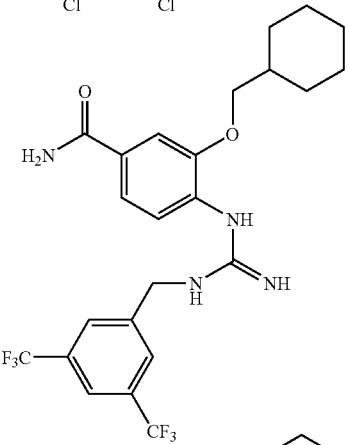

G10

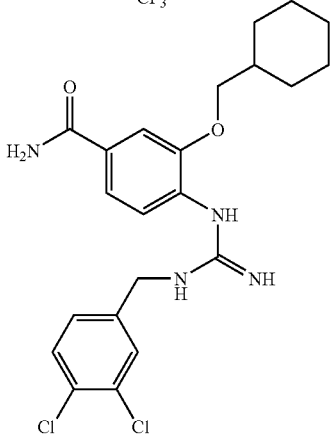

H4

Figure 2:
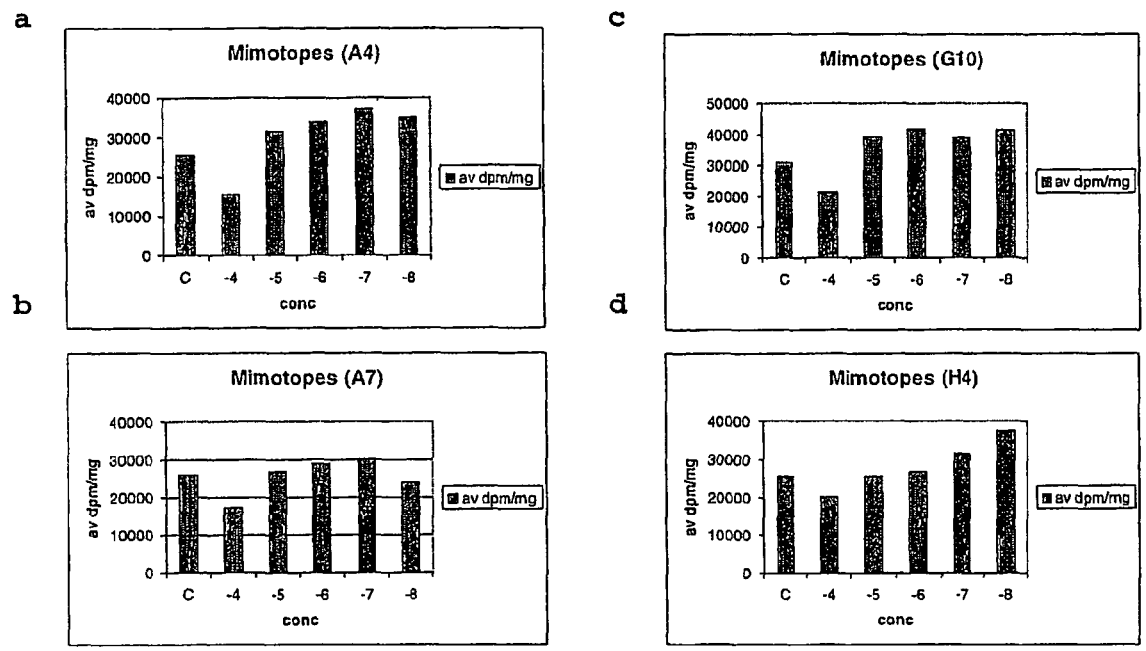
FIG. 2 shows the results of experiments on the effect of four different compounds according to the invention on the uptake of radioactive-labelled L-arginine into HeLa cells. C: Control performed in the absence of test compound. The vertical axis shows average disintegrations per minute/mg (dpm/mg) test compound, and the horizontal axis shows the concentration of test compound, expressed as $log_{10}$ (drug concentration). Panel A: Compound A4; Panel B: Compound A7; Panel C: G10; Panel D: Compound H4.

However, when full concentration-response curves were prepared, it was found that, in contrast to the initial finding, four molecules exerted a stimulatory effect on L-arginine transport at low concentration ($10^{-7}$ and $10^{-8}$ M), as shown in FIG. 2. To our knowledge these are the first data to demonstrate that a synthetic compound is able to stimulate arginine transport. In the light of the foregoing discussion, we propose that this effect may be associated with therapeutic benefit.

Further studies have been performed to characterize the effects of compounds from library M0006 on arginine transport in endothelial cells. Studies performed in the endothelial cell line EA.hy.926 (Harrison-Shostak et al, 1997) have identified a number of compounds which exert a stimulatory effect on L-arginine transport. This cell line is considered to be more physiologically relevant than HeLa cells to the target conditions, and in fact was more sensitive. The results are summarised in FIG. 4. Table 16 summarises results for the compounds so far identified which have the highest activity in the arginine transport assay.

TABLE 16

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 01 A04 | | 3-Cyclobutylmethoxy-4-[N'-(3,5-trifluoromethyl-benzyl)-guanidino]-benzamide | 103% 108% |
| Plate 2 M0006 01 A07 | | 3-Cyclobutylmethoxy-4-[N'-(3,4-dichloro-benzyl)-guanidino]-benzamide | 87% 66% |

TABLE 16-continued

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 01 A11 | 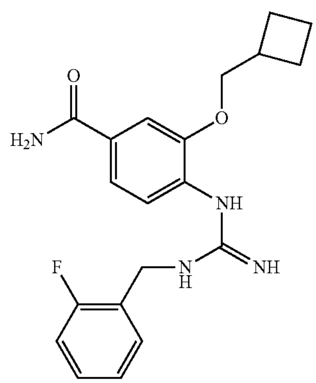 | 3-Cyclobutylmethoxy-4-[N'-(2-fluoro-benzyl)-guanidino]-benzamide | 159% 128% |
| M0006 01 A12 | 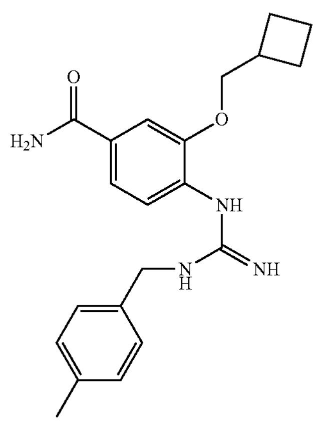 | 3-Cyclobutylmethoxy-4-[N'-(4-methyl-benzyl)-guanidino]-benzamide | 179% 160% |
| M0006 01 B04 | 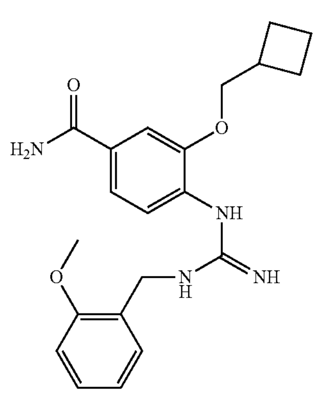 | 3-Cyclobutylmethoxy-4-[N'-(2-methoxy-benzyl)-guanidino]-benzamide | 130% 122% |

TABLE 16-continued

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 01 B12 | | 3-Cyclobutylmethoxy-4-(N'-cyclohexyl-guanidino)-benzamide | 161% 134% |
| M0006 01 C12 | | 3-Cyclopropylmethoxy-4-[N'-(2-phenyl-propyl)-guanidino]-benzamide | 116% 133% |
| M0006 01 F05 | | 4-[N'-(2-Phenyl-propyl)-guanidino)-3-(tetrahydro-pyran-2-ylmethoxy)-benzamide | 135% 130% |
| M0006 01 F09 | | 4-(N'-Benzyl-guanidino)-3-(tetrahydro-pyran-2-ylmethoxy)-benzamide | 140% 110% |

TABLE 16-continued

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 01 F10 | | 4-(N'-Benzo[1,3]dioxol-5-ylmethyl-guanidino)-3-(tetrahydro-pyran-2-ylmethoxy)-benzamide | 119% 131% |
| M0006 01 F12 | | 4-(N'-Isobutyl-guanidino)-3-(tetrahydro-pyran-2-ylmethoxy)-benzamide | 103% 146% |
| M0006 01 G10 | | 3-Cyclohexylmethoxy-4-[N'-(3,5-trifluoromethyl-benzyl)-guanidino]-benzamide | 125% 188% |

TABLE 16-continued

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 01 H04 | 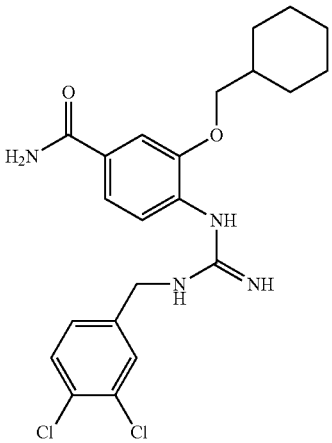 | 3-Cyclohexylmethoxy-4-[N'-(3,4-dichloro-benzyl)-guanidino]-benzamide | 99% 92% |
| M0006 01 H10 | 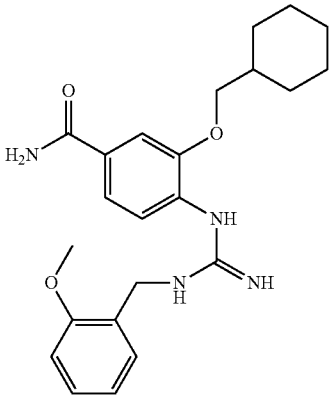 | 3-Cyclohexylmethoxy-4-[N'-(2-methoxy-benzyl)-guanidino]-benzamide | 153% 146% |
| M0006 01 H11 | 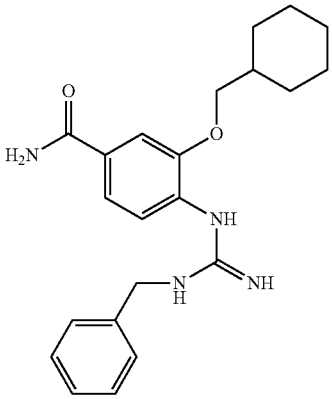 | 4-(N'-Benzyl-guanidino)-3-cyclohexylmethoxy-benzamide | 131% 190% |

TABLE 16-continued

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 02 A10 | | 3-Cyclohexylmethoxy-4-(N'-cyclohexylmethyl-guanidino)-benzamide | 123% 127% |
| M0006 02 D06 | | 3-Benzyloxy-4-{N'-[(5-nitro-pyridin-2-ylamino)-methyl]-guanidino}-benzamide | 176% 138% |
| M0006 02 E06 | | 4-(N'-Benzyl-guanidino)-3-benzyloxy-benzamide | 167% 160% |

TABLE 16-continued

Summary of active structures (arginine uptake, at two concentrations $10^{-8}$ M (top) and $10^{-7}$ M (bottom))

| Plate position compound ID from Example 1 Library (Plate) (Position) | Structure | Structure Name | Arg uptake (% control) from FIG. 4 |
|---|---|---|---|
| M0006 02 F06 | 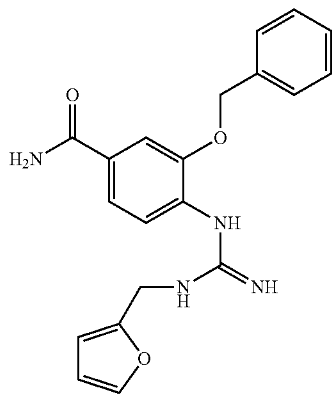 | 3-Benzyloxy-4-(N'-furan-2-ylmethyl-guanidino)-benzamide | 158% 126% |
| M0006 02 H08 | 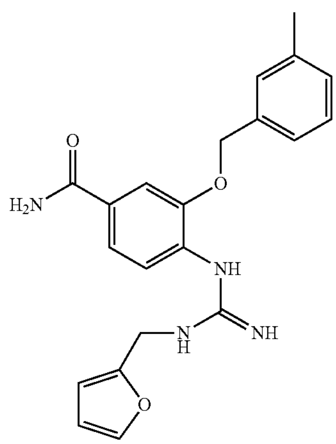 | 4-(N'-Furan-2-ylmethyl-guanidino)-3-(3-methyl-benzyloxy)-benzamide | 108% 182% |

EXAMPLE 10

Effect of L-Arginine Analogues on Vascular Tone

Figure 3:
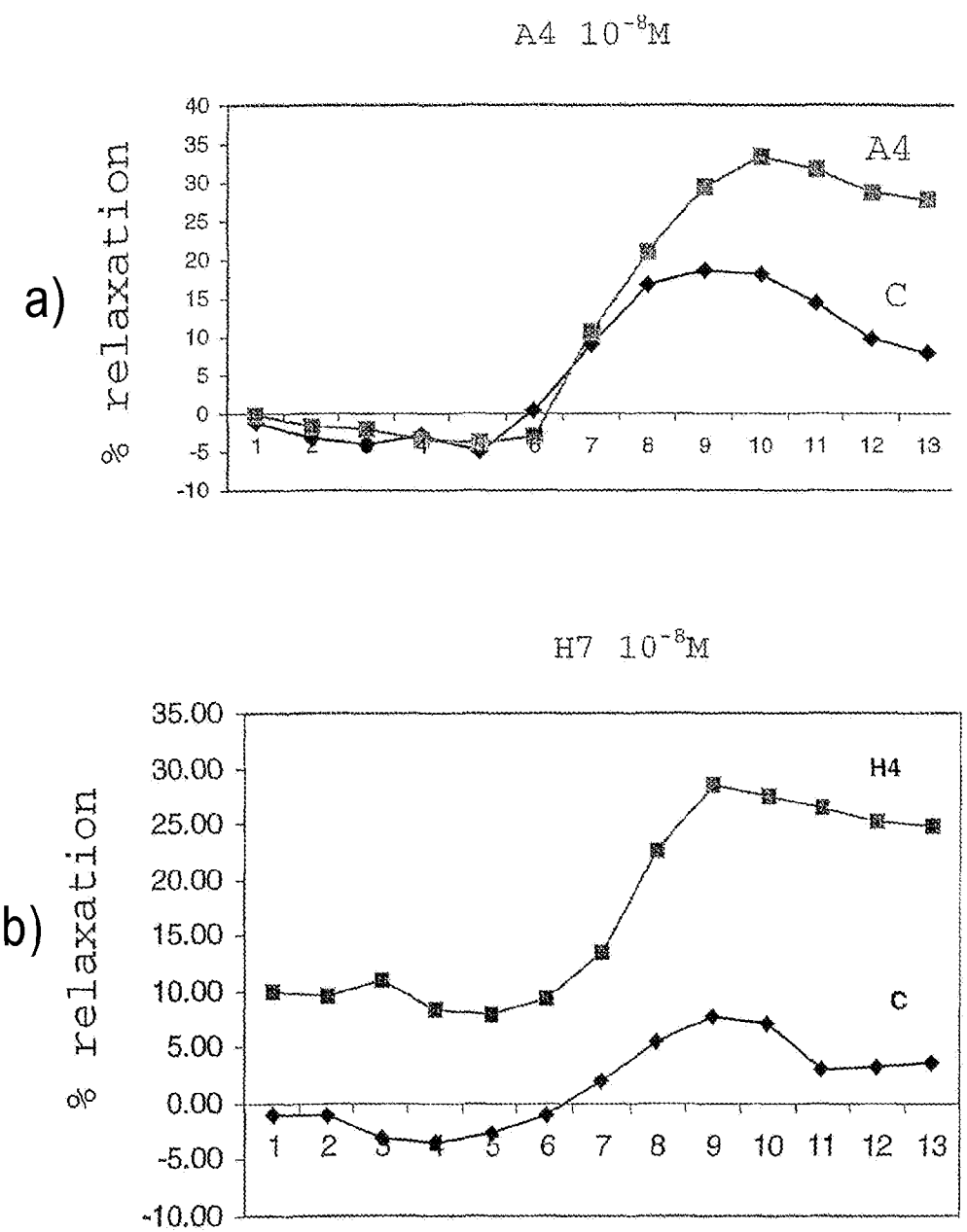
FIG. 3 illustrates the augmentation of vascular relaxation produced by increasing concentrations of acetyl choline in the absence of and presence of test compounds. C indicates control.

Initially four compounds were tested for their effect on vascular tone, using an isolated aortic ring assay. In this assay, sections of rat aorta are mounted in an organ bath, and tension is determined continuously using a strain gauge, as described by Furchgott & Zawadski (1980). The effect of test compounds on the vasorelaxant effect of the endothelial-dependent vasodilator acetyl choline (ACh) was examined. Compounds A4 and H4, each at a concentration of $10^{-8}$M, were found to induce a significant augmentation of acetyl choline-induced vascular relaxation. These results are summarised in FIG. 3. It will be appreciated that similar experiments may be performed using sections of human aorta, coronary artery or peripheral artery obtained at surgery.

EXAMPLE 11

Additional Characterization of L-Arginine Analogues

Additional characterization of the compounds is also performed in primary cultures of isolated bovine aortic endothelial cells, using the methods described in Example 9. Aortic endothelial cells are isolated from bovine aorta using standard cell culture methods (see for example Cocks et al, 1985). Similar methods may also be used to isolate human aortic, coronary artery or peripheral artery endothelial cells from surgical material so that the compounds can be tested in a human system.

EXAMPLE 12

Effect of L-Arginine Analogues on Arginase Activity

The observed facilitatory action of the arginine analogues may possibly be explained by an inhibitory action upon the enzyme arginase. Such an effect would be expected to augment L-arginine transport and thereby to increase nitric oxide synthesis, in the absence of any inhibitory action upon nitric oxide synthase itself. The effect of the compounds on arginase enzymatic activity is determined by measuring the rate of production of urea by arginase in the presence of its substrate, L-arginine, and the compound of interest. These assays are performed in EA.hy.926 cells or in primary cultures of endothelial cells, obtained as described in Example 9. Alternatively they may be performed using aortic or other arterial rings, obtained as described in Example 10.

EXAMPLE 13

In Vivo Effects of L-Arginine Analogues

Compounds found to be active in the in vitro studies are tested for their effects in vivo in experimental animals, and ultimately in humans.

In animal studies, the effect of the compound on blood pressure is tested following intravenous infusion into rats and rabbits. The effect of the compounds on regional vascular tone is tested by intra-arterial hindlimb infusions in rabbits, according to the method of Kaye et al., (1994). The effect of the compounds on coronary vascular resistance is tested by direct intracoronary infusion into sheep, using the method of Quyyumi et al., (1997).

Other suitable methods for in vivo assessment of efficacy, bioavailability and safety of the compounds of the invention will be known to those skilled in the art.

Once the pharmacological action of the compounds of the invention is established in animal studies, and their safety is assessed, further investigations are carried out on humans in vivo. For example, the effect of the compounds on forearm vascular tone is assessed by direct intra-arterial infusion, using the method of Kaye et al., (2000), and the effect of the compounds on blood pressure is evaluated.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Carey, F. A. and R. J. Sundberg. 1983. Advanced Organic Chemistry Part A: Structure and Mechanisms. New York, Plenum.

Carey, F. A. and R. J. Sundberg. 1983. Advanced Organic Chemistry Part B: Reactions and Synthesis. New York, Plenum.

Cocks T M, Angus J A, Campbell J H, and Campbell G R. Release and properties of endothelium-derived relaxing factor (EDRF) from endothelial cells in culture J Cell Physiol 1985; 123:310-320.

Creager M A, Gallagher S J, Girerd X J, Coleman S M, Dzau V J, Cooke J P. L-arginine improves endothelium-dependent vasodilation in hypercholesterolemic humans. *J Clin Invest.* 1992; 90:1248-1253.

Ellman, J. A., Thompson, L. A., *Chem. Rev.,* 1996, 96, 555-600.

Furchgott R F, Zawadski J V. The obligatory role of endothelial cells in the relaxation of arterial smooth muscle by acetylcholine. *Nature.* 1980; 288:373-376.

Girerd X J, Hirsch A T, Cooke J P, Dzau V J, Creager M A. L-arginine augments endothelium-dependent vasodilation in cholesterol-fed rabbits. *Circ Res.* 1990; 67:1301-1308.

Greene, T. W. and P. G. M. Wuts. 1991. *Protective Groups in Organic Synthesis.* New York, John Wiley & Sons, Inc.

Harrison-Shostak D. C. Lemasters, J. J. Edgell C. J. and Herman B. Role of ICE-like proteases in endotheleial cell hypoxic and reperfusion injury. *Biochem. Biophys. Res. Comm.* 1997:24:844-847

Hirooka Y, Imaizumi T, Tagawa T, Shiramoto M, Endo T, Ando S-I, Takeshita A. Effects of L-arginine on impaired acetylcholine-induced and ishemic vasodilation of the forearm in patients with heart failure. *Circulation.* 1994; 90:658-668.

Kaye D M, Jennings G, Angus J A. Evidence for impaired endothelium dependent vasodilation in experimental left ventricular dysfunction. *Clin Exp Pharmacol and Physiol.* 1994; 21:709-719.

Kaye D M, Ahlers B A, Autelitano D J et al. In vivo and in vitro evidence for impaired arginine transport in human heart failure. *Circulation* 2000, 102:2707-12.

Kearney, P. C., Fernandez, M., and Flygare, J. A., *Tetrahedron Lett.,* 1998 39, 2663.

Lerman A, Burnett J C, Jr., Higano S T, McKinley L J, Holmes D R, Jr. Long-term L-arginine supplementation improves small-vessel coronary endothelial function in humans. *Circulation.* 1998; 97:2123-2128.

Maeji, N. J., Valerio, R. M., Bray, A. M., Campbell, R. A. and Geysen, H. M. Grafted supports used with the multipin method of peptide synthesis. *Reactive Polymers* 1994, 22; 203.

March, J. 1992. Advanced Organic Chemistry: Reactions, Mechanisms, and Structure. New York, Wiley Interscience.

Macor J E and Kowala M C, Discovery Chemistry and Metabolic and Cardiovascular Drug Discovery Pharmaceutical Research Institute, *Annual Reports in Medicinal Chemistry,* 2000 35:63-70.

Maeji, N. J., Valerio, R. M., Bray, A. M., Campbell, R. A., Geysen, H. M., *Reactive Polymers* 1994, 22, 203-212.

Quyyumi A A, Dakak N, Diodati J G, et al. Effect of L-arginine on human coronary endothelium-dependent and physiologic vasodilation. *J Am Coll Cardiol.* 1997; 30:1220-7.

Rector T S, Bank A J, Mullen K A, Tschumperlin L K, Sih R, Pillai K, Kubo S H. Randomized, double-blind, placebo-controlled study of supplemental oral L-arginine in patients with heart failure. *Circulation.* 1996; 93:2135-2141.

Sirmnons W W, Closs E I, Cunningham J M et al *J. Biol. Chem.* 1996; 271:11694-11702

The invention claimed is:

1. A compound of formula I:

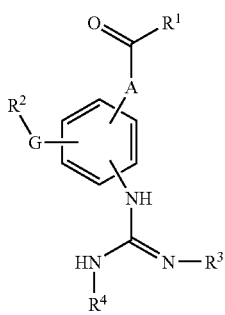

Formula I where
A is a methylene group or is absent;
G is O;
R¹ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl)alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and R² is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R³ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R⁴ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

2. A compound according to claim 1, in which A is absent, R¹ is amino or hydroxy and R² is optionally substituted alkyl or optionally substituted cycloalkyl.

3. A compound according to claim 1, of formula II:

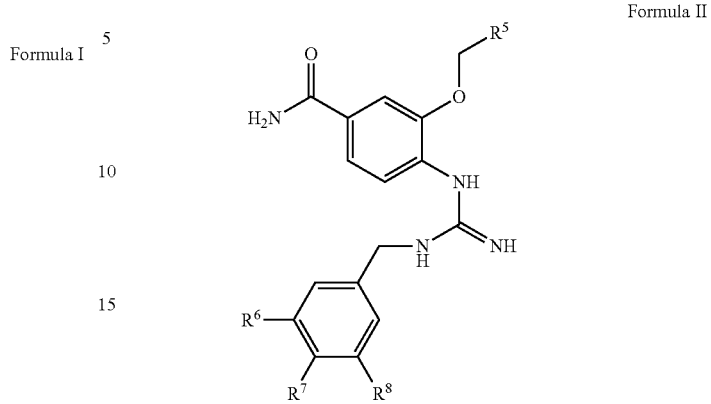

Formula II in which
R⁵ is cycloalkyl of 4-6 carbons;
R⁶ is trihaloalkyl of 1-3 carbon atoms, or halogen, or is absent;
R⁷ is a halogen or is absent; and
R⁸ is a halogen, or is trihaloalkyl of 1 to 3 carbon atoms.

4. A compound according to claim 3, in which
R⁵ is cyclobutyl or cyclohexyl;
R⁶ is chlorine or absent; and
R⁸ is chlorine or trifluoromethyl.

5. A compound according to claim 3, in which both R⁶ and R⁸ are trifluoromethyl and R⁷ is absent, or both R⁷ and R⁸ are chlorine and R⁶ is absent.

6. A compound according to claim 1 selected from the group consisting of:
3-Cyclobutylmethoxy-4-[N'-(3,5-trifluoromethyl-benzyl)-guanidino]-benzamide;
3-Cyclobutylmethoxy-4-[N'-(3,4-dichloro-benzyl)-guanidino]-benzamide;
3-Cyclobutylmethoxy-4-[N'-(2-fluoro-benzyl)-guanidino]-benzamide;
3-Cyclobutylmethoxy-4-[N'-(4-methyl-benzyl)-guanidino]-benzamide;
3-Cyclobutylmethoxy-4-[N'-(2-methoxy-benzyl)-guanidino]-benzamide;
3-Cyclobutylmethoxy-4-(N'-cyclohexyl-guanidino)-benzamide;
3-Cyclopropylmethoxy-4-[N'-(2-phenyl-propyl)-guanidino]-benzamide;
4-[N'-(2-Phenyl-propyl)-guanidino]-3-(tetrahydro-pyran-2-ylmethoxy)-benzamide;
4-(N'-Benzyl-guanidino)-3-(tetrahydro-pyran-2-ylmethoxy)-benzamide;
4-(N'-Benzo[1,3]dioxol-5-ylmethyl-guanidino)-3-(tetrahydro-pyran-2-ylmethoxy)-benzamide;
4-(N'-Isobutyl-guanidino)-3-(tetrahydro-pyran-2-ylmethoxy)-benzamide;
3-Cyclohexylmethoxy-4-[N'-(3,5-trifluoromethyl-benzyl)-guanidino]-benzamide;
3-Cyclohexylmethoxy-4-[N'-(3,4-dichloro-benzyl)-guanidino]-benzamide;
3-Cyclohexylmethoxy-4-[N'-(2-methoxy-benzyl)-guanidino]-benzamide;
4-(N'-Benzyl-guanidino)-3-cyclohexylmethoxy-benzamide;
3-Cyclohexylmethoxy-4-(N'-cyclohexylmethyl-guanidino)-benzamide;

3-Benzyloxy-4-{N'-[(5-nitro-pyridin-2-ylamino)-methyl]-guanidino}-benzamide;

4-(N'-Benzyl-guanidino)-3-benzyloxy-benzamide;

3-Benzyloxy-4-(N'-furan-2-ylmethyl-guanidino)-benzamide; and 4-(N'-Furan-2-ylmethyl-guanidino)-3-(3-methyl-benzyloxy)-benzamide.

7. A combinatorial library of compounds of formula I:

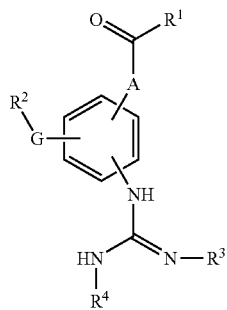

Formula I where

A is a methylene group or is absent;

G is O;

$R^1$ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl)alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and $R^2$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^3$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^4$ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

8. A composition comprising a compound according to claim 1, together with a pharmaceutically acceptable carrier.

9. A compound for modulating L-arginine transport into cells, in which the compound is of formula I:

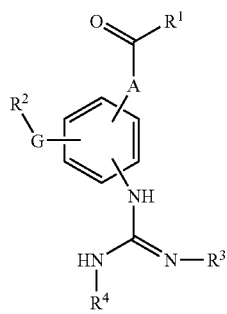

Formula I where

A is a methylene group or is absent;

G is O;

$R^1$ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl)alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and $R^2$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^3$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^4$ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

10. A compound of formula I:

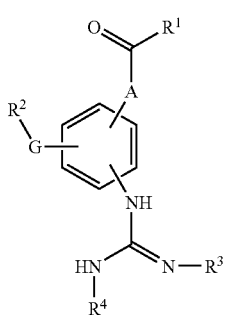

Formula I where

A is a methylene group or is absent;

G is O;

$R^1$ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl)alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and $R^2$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^3$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^4$ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

11. A compound of formula I:

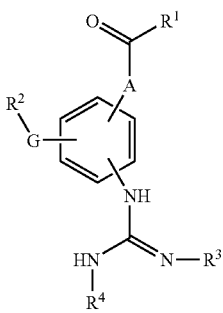

Formula I where

A is a methylene group or is absent;

G is O;

$R^1$ is selected from the group consisting of hydrogen, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl) alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl) alkyl, and (cycloheteroalkyl)oximinoalkyl; and $R^2$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^3$ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and $R^4$ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

12. A combinatorial library of compounds of formula I:

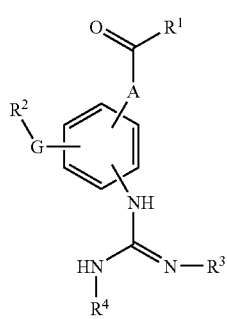

Formula I where

A is a methylene group or is absent;

G is O;

R¹ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl) alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and R² is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R³ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R⁴ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

13. A combinatorial library of compounds of formula I:

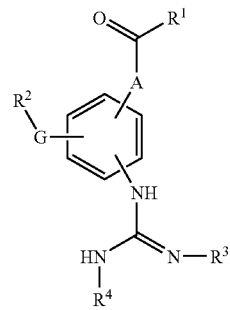

Formula I where

A is a methylene group or is absent;

G is O;

R¹ is selected from the group consisting of hydrogen, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl) alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl) alkyl, and (cycloheteroalkyl)oximinoalkyl; and R² is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R³ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R⁴ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

14. A compound for modulating L-arginine transport into cells, in which the compound is of formula I:

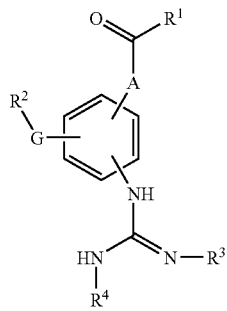

Formula I where

A is a methylene group or is absent;

G is O;

R¹ is selected from the group consisting of hydrogen, hydroxyl, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl) alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and R² is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R³ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R⁴ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

15. A compound for modulating L-arginine transport into cells, in which the compound is of formula I:

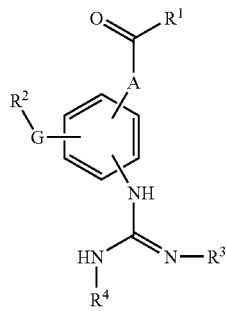

Formula I where

A is a methylene group or is absent;

G is O;

R¹ is selected from the group consisting of hydrogen, thio, amino, optionally substituted lower alkyl, lower alkylamino, arylamino, aralkylamino, heteroarylamino, heteroaralkylamino, lower alkyloxy, aryloxy, heteroaryloxy, cycloalkyloxy, cycloheteroalkyloxy, aralkyloxy, heteroaralkyloxy, (cycloalkyl) alkyloxy, (cycloheteroalkyl) alkyloxy, lower alkylthio, arylthio, heteroarylthio, cycloalkylthio, cycloheteroalkylthio, aralkylthio, heteroaralkylthio, (cycloalkyl)alkylthio, (cycloheteroalkyl)alkylthio, imino lower alkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl; and R² is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R³ is selected from the group consisting of hydrogen, optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl; and R⁴ is selected from the group consisting of optionally substituted lower alkyl, optionally substituted aryl, optionally substituted aralkyl, optionally substituted heteroaryl, optionally substituted heteroaralkyl, optionally substituted cycloalkyl, and optionally substituted cycloheteroalkyl.

16. A composition comprising a compound according to claim 10, together with a pharmaceutically acceptable carrier.

17. A composition comprising a compound according to claim 11, together with a pharmaceutically acceptable carrier.

18. A compound according to claim 10, in which A is absent, R¹ is amino or hydroxy and R² is optionally substituted alkyl or optionally substituted cycloalkyl.

19. A compound according to claim 18, in which A is absent, R¹ is amino and R² is optionally substituted alkyl or optionally substituted cycloalkyl.

20. A compound according to claim 11, in which A is absent, R¹ is amino and R² is optionally substituted alkyl or optionally substituted cycloalkyl.

21. A compound according to claim 1, wherein $R_4$ is optionally substituted (cycloalkyl)alkyl.

22. A compound according to claim 9, wherein $R_4$ is optionally substituted (cycloalkyl)alkyl.

23. A compound according to claim 10, wherein $R_4$ is optionally substituted (cycloalkyl)alkyl.

24. A compound according to claim 11, wherein $R_4$ is optionally substituted (cycloalkyl)alkyl.

25. A compound according to claim 14, wherein $R_4$ is optionally substituted (cycloalkyl)alkyl.

26. A compound according to claim 15, wherein $R_4$ is optionally substituted (cycloalkyl)alkyl.

27. A combinatorial library according to claim 7, wherein $R_4$ is optionally substituted (cycloalkyl)alkyl.

28. A combinatorial library according to claim 12, wherein $R_4$ is optionally substituted (cycloalkyl)alkyl.

29. A combinatorial library according to claim 13, wherein $R_4$ is optionally substituted (cycloalkyl)alkyl.

* * * * *